(12) United States Patent
Tamura et al.

(10) Patent No.: US 8,597,619 B2
(45) Date of Patent: Dec. 3, 2013

(54) THICKENER OR GELLANT FOR OIL MATERIALS, GEL COMPOSITION COMPRISING SAME, AND METHOD OF PRODUCING COSMETIC MATERIAL OR TOPICAL AGENT

(75) Inventors: Seiki Tamura, Ichihara (JP); Tomohiro Iimura, Sodegaura (JP); Tatsuo Souda, Ichihara (JP); Akito Hayashi, Ichihara (JP); Haruhiko Furukawa, Chiba (JP)

(73) Assignee: Dow Corning Toray., Ltd., Chiyoda-ku, Tokyo (JP)

( * ) Notice: Subject to any disclaimer, the term of this patent is extended or adjusted under 35 U.S.C. 154(b) by 0 days.

(21) Appl. No.: 13/517,055

(22) PCT Filed: Dec. 21, 2010

(86) PCT No.: PCT/JP2010/073668
§ 371 (c)(1),
(2), (4) Date: Aug. 10, 2012

(87) PCT Pub. No.: WO2011/078395
PCT Pub. Date: Jun. 30, 2011

(65) Prior Publication Data
US 2012/0328539 A1 Dec. 27, 2012

(30) Foreign Application Priority Data
Dec. 21, 2009 (JP) ................................. 2009-289867

(51) Int. Cl.
*A61P 31/04* (2006.01)
*A61P 17/02* (2006.01)
*A61K 38/43* (2006.01)
*A61Q 19/08* (2006.01)
*A61Q 1/02* (2006.01)
*A61K 47/34* (2006.01)
*A61K 8/89* (2006.01)

(52) U.S. Cl.
USPC .......... 424/59; 424/63; 424/70.12; 424/70.9; 424/94.1; 514/772.3; 528/25

(58) Field of Classification Search
None
See application file for complete search history.

(56) References Cited

U.S. PATENT DOCUMENTS

| | | | |
|---|---|---|---|
| 4,431,789 A | 2/1984 | Okazaki et al. | |
| 5,260,402 A * | 11/1993 | Weitemeyer et al. | ........... 528/29 |
| 5,306,838 A | 4/1994 | Shioya et al. | |
| 5,609,167 A | 3/1997 | Hensen et al. | |
| 5,656,200 A | 8/1997 | Boettcher et al. | |
| 5,874,069 A | 2/1999 | Mendolia et al. | |
| 5,889,108 A | 3/1999 | Zhang | |
| 5,919,441 A | 7/1999 | Mendolia et al. | |
| 5,929,163 A | 7/1999 | Harashima | |
| 5,981,680 A | 11/1999 | Petroff et al. | |
| 6,043,203 A | 3/2000 | Urfer et al. | |
| 6,150,311 A * | 11/2000 | Decoster et al. | ............... 510/122 |
| 6,168,782 B1 | 1/2001 | Lin et al. | |
| 6,280,748 B1 | 8/2001 | Morita et al. | |
| 6,534,072 B2 | 3/2003 | Mondet et al. | |
| 7,001,971 B2 | 2/2006 | Nakanishi | |
| 7,482,419 B2 | 1/2009 | Caprasse et al. | |
| 7,655,744 B2 | 2/2010 | Miyanaga | |
| 7,771,709 B2 | 8/2010 | Nakanishi et al. | |
| 7,994,250 B2 | 8/2011 | Origuchi et al. | |
| 2004/0091439 A1* | 5/2004 | Kamei et al. | ............... 424/70.12 |
| 2009/0326151 A1 | 12/2009 | Shimizu et al. | |

FOREIGN PATENT DOCUMENTS

| | | |
|---|---|---|
| EP | 2103301 A1 | 9/2009 |
| JP | 62-034039 A | 7/1987 |
| JP | 05-311076 A | 11/1993 |
| JP | 06-157236 A | 6/1994 |
| JP | 06-089147 B | 11/1994 |
| JP | 06-305933 A | 11/1994 |
| JP | 07-025728 A | 1/1995 |
| JP | 07-033622 A | 2/1995 |
| JP | 07-100358 A | 4/1995 |
| JP | 08-217626 A | 8/1996 |
| JP | 08-268831 A | 10/1996 |
| JP | 08-268832 A | 10/1996 |
| JP | 09-071504 A | 3/1997 |
| JP | 09-194323 A | 7/1997 |
| JP | 10-245317 A | 9/1998 |
| JP | 11-049957 A | 2/1999 |

(Continued)

OTHER PUBLICATIONS

English language abstract for JP 05-311076 extracted from the espacenet.com database on Aug. 27, 2012, 14 pages.
English language abstract for JP 06-089147 extracted from the espacenet.com database on Aug. 27, 2012, 16 pages.
English language abstract and translation for JP 06-157236 extracted from the PAJ database on Aug. 27, 2012, 26 pages.
English language abstract and translation for JP 06-305933 extracted from the PAJ database on Aug. 27, 2012, 36 pages.
English language abstract and translation for JP 07-025728 extracted from the PAJ database on Aug. 27, 2012, 39 pages.
English language abstract and translation for JP 07-033622 extracted from the PAJ database on Aug. 27, 2012, 40 pages.

(Continued)

*Primary Examiner* — Robert A Wax
*Assistant Examiner* — Randeep Singh
(74) *Attorney, Agent, or Firm* — Howard & Howard Attorneys PLLC

(57) ABSTRACT

This inventive thickener or gellant for oil materials is characterized by comprising (A) an high molecular weight organopolysiloxane that has a polyglycerol structure-containing hydrophilic group Q and that is represented by the following structural formula (1): $R_{3-q}(R^{11})_q Si\text{—}O\text{—}(SiR^{11}{}_2\text{—}O)_{n1}\text{—}(SiR^{11}Q\text{-}O)_{n2}\text{—}(SiR^{11}L\text{-}O)_{n3}\text{—}Si(R)^{11}{}_q R_{3-q}$ wherein $R^{11}$ is a monovalent hydrocarbyl group or a hydrogen atom; L is a chain organosiloxane group, n1, n2, and n3 are numbers in the ranges $200 \leq n1 \leq 1000$, $0 \leq n2 \leq 20$, and $0 \leq n3 \leq 50$; R is a group selected from L and Q; q is an integer in the range from 0 to 3; wherein when n2=0, q is an integer in the range from 1 to 3 and at least one R is Q. The thickener or gellant exhibits an excellent compatibility with a variety of oil systems.

26 Claims, No Drawings

(56) References Cited

FOREIGN PATENT DOCUMENTS

| | | |
|---|---|---|
| JP | 2000-063225 A | 2/2000 |
| JP | 2000-128740 A | 5/2000 |
| JP | 2000-143458 A | 5/2000 |
| JP | 2001-011281 A | 1/2001 |
| JP | 2002-179798 A | 6/2002 |
| JP | 2004-182680 A | 7/2004 |
| JP | 2004-231608 A | 8/2004 |
| JP | 2004-339244 A | 12/2004 |
| JP | 2005-042097 A | 2/2005 |
| JP | 2005-089494 A | 4/2005 |
| JP | 2005-194523 A | 7/2005 |
| JP | 2007-532754 A | 11/2007 |
| WO | WO 93/10748 A1 | 6/1993 |
| WO | WO 94-06899 | 3/1994 |
| WO | WO 94/16677 A1 | 8/1994 |
| WO | WO 03/041664 A1 | 5/2003 |
| WO | WO 03/075864 A1 | 9/2003 |
| WO | WO 2005/054341 A1 | 6/2005 |
| WO | WO 2008/004502 A1 | 1/2008 |

OTHER PUBLICATIONS

English language abstract and translation for JP 07-100358 extracted from the PAJ database on Aug. 28, 2012, 35 pages.
English language abstract and translation for JP 08-217626 extracted from the PAJ database on Aug. 28, 2012, 53 pages.
English language abstract and translation for JP 08-268831 extracted from the PAJ database on Aug. 28, 2012, 36 pages.
English language abstract and translation for JP 08-268832 extracted from the PAJ database on Aug. 28, 2012, 47 pages.
English language abstract and translation for JP 09-071504 extracted from the PAJ database on Aug. 27, 2012, 29 pages.
English language abstract and translation for JP 09-194323 extracted from the PAJ database on Aug. 28, 2012, 31 pages.
English language abstract and translation for JP 10-245317 extracted from the PAJ database on Aug. 28, 2012, 39 pages.
English language abstract for JP 11-049957 extracted from the espacenet.com database on Aug. 28, 2012, 9 pages.
English language abstract for JP 62-034039 extracted from the espacenet.com database on Nov. 28, 2012, 14 pages.
English language abstract for JP 2000-063225 extracted from the espacenet.com database on Aug. 28, 2012, 17 pages.
English language abstract and translation for JP 2000-128740 extracted from the PAJ database on Aug. 28, 2012, 29 pages.
English language abstract and translation for JP 2000-143458 extracted from the PAJ database on Aug. 28, 2012, 29 pages.
English language abstract for JP 2001-011281 extracted from the espacenet.com database on Aug. 28, 2012, 14 pages.
English language abstract for JP 2002-179798 extracted from the espacenet.com database on Aug. 27, 2012, 27 pages.
English language abstract and translation for JP 2004-182680 extracted from the PAJ database on Aug. 27, 2012, 96 pages.
English language abstract and translation for JP 2004-231608 extracted from the PAJ database on Aug. 27, 2012, 75 pages.
English language abstract for JP 2004-339244 extracted from the espacenet.com database on Aug. 28, 2012, 45 pages.
English language abstract for JP 2005-042097 extracted from the espacenet.com database on Aug. 27, 2012, 59 pages.
English language abstract and translation for JP 2005-089494 extracted from the PAJ database on Aug. 27, 2012, 47 pages.
English language abstract and translation for JP 2005-194523 extracted from the espacenet.com database on Aug. 27, 2012, 53 pages.
English language abstract not available for JP 2007-532754; however, see English language equivalent US 7,482,419. Original Document extracted from the espacenet.com database on Aug. 28, 2012, 39 pages.
English language abstract for WO 03/041664 extracted from the espacenet.com database on Aug. 27, 2012, 71 pages.
English language abstract for WO 03/075864 extracted from the espacenet.com database on Aug. 27, 2012, 38 pages.
English language abstract not available for WO 93/10748; however, see English language equivalent US 5,609,167. Original Document extracted from the espacenet.com database on Aug. 28, 2012, 22 pages.
English language abstract for WO 94/16677 extracted from the espacenet.com database on Aug. 28, 2012, 29 pages.
English language abstract for WO 2005/054341 extracted from the espacenet.com database on Aug. 28, 2012, 168 pages.
English language abstract for WO 2008/004502 extracted from the espacenet.com database on Aug. 28, 2012, 92 pages.
International Search Report for Application No. PCT/JP2010/073668 dated Jun. 22, 2011, 4 pages.
English language abstract for WO 94-06899 extracted from the espacenet.com database on Nov. 28, 2012, 29 pages.

* cited by examiner

US 8,597,619 B2

THICKENER OR GELLANT FOR OIL MATERIALS, GEL COMPOSITION COMPRISING SAME, AND METHOD OF PRODUCING COSMETIC MATERIAL OR TOPICAL AGENT

RELATED APPLICATIONS

This application claims priority to and all the advantages of International Patent Application No. PCT/JP2010/073668, filed on Dec. 21, 2010, which claims priority to Japanese Patent Application No. JP2009-289867, filed on Dec. 21, 2009.

TECHNICAL FIELD

The present invention relates to a thickener or gellant for oil materials, wherein the thickener or gellant contains a high molecular weight organopolysiloxane that has a polyglycerol structure-containing hydrophilic group and a degree of polymerization for its organopolysiloxane chain of more than 200, to a gel composition, and to a gel-form cosmetic material and topical gel that comprise this gel composition. The present invention more particularly relates to a thickener or gellant for a oil material, wherein the thickener or gellant contains a high molecular weight hydrophilic organopolysiloxane that has a tetraglycerol structure-containing hydrophilic group and a degree of polymerization for its organopolysiloxane chain of more than 300, to a gel composition, and to a gel-form cosmetic material and topical gel that comprise this gel composition.

The organopolysiloxane according to the present invention—because it is modified with a hydrophilic functional group in the form of a polyglycerol structure-containing hydrophilic group and because the organopolysiloxane chain constituting its main chain has a relatively high degree of polymerization—exhibits the functionality of being able to form a stable gel that incorporates an oil. Moreover, this organopolysiloxane that additionally has a siloxane chain and/or a long-chain hydrocarbyl group in side chain position exhibits an excellent compatibility with a variety of oils, e.g., silicone oils, hydrocarbon oils, ester oils, and so forth, that is achieved through adjustment of the quantity of introduction of these side chain modifying groups, and upon its incorporation in a cosmetic material can therefore provide a cosmetic material that has a suppressed oily feel and that, after application, exhibits an excellent moisturizing sensation and provides a natural skin sensation without feeling discomfort.

In particular, the high molecular weight organopolysiloxane having a tetraglycerol structure as its hydrophilic functional group and additionally having a siloxane chain and long-chain hydrocarbyl group in side chain position exhibits an excellent compatibility with a variety of oil-based systems and functions as an excellent oil thickener that based on its quantity of addition can provide free-ranging control of, for example, the form and viscosity of an oil or cosmetic material. It also functions as an excellent dispersing immobilizing agent that can uniformly and stably disperse immobilize a powder or colorant in an oil material-based cosmetic material and that, after the application thereof to the skin, is also able to maintain an excellent cosmetic effect and a discomfort-free natural skin sensation for approximately a day.

Furthermore, its combination with specific quantities of an oil material, organic alcohol compound, and water produces a stable gel composition that can maintain a wide range of silicone/organic mixed oils in a gel form that has a viscoelasticity in the intermediate range between liquid and solid. A stable gel composition can be obtained simply by the incorporation of a powder in this composition and also by the incorporation of, for example, an ultraviolet absorber, film-forming agent, or a salt in the indicated composition. In addition, the dilution of these gel compositions by the further incorporation of water thereinto can provide a lower viscosity cosmetic material in a freely selectable form, e.g., a paste, cream, or liquid emulsion. The further incorporation of water and a physiologically active material into these gel compositions can also provide a topical agent in a freely selectable form as above.

BACKGROUND ART

When one examines the background art from the standpoint of oil thickening or gelation, the oil-based systems used as cosmetic materials are found to frequently contain a silicone oil, and a problem in such cases has been the poor effects exercised by organic thickeners or gellants. The oil thickening/gelling art is an art that can provide the cosmetic producer with the freedom to freely control the form of a cosmetic formulation, for example, from a liquid form to a cream, paste, gel, or solid, and thus is an extremely important art. As a consequence, much effort has been directed to the development of modified silicone-based thickeners or gellants that are also advantageous with regard to tactile feel and to the application of these modified silicone-based thickeners or gellants to cosmetic materials.

The art of solidifying an oil using an alkyl-modified silicone wax has long been known, but the problems generally associated with this have been, inter alia, a substantial oily feel, a heavy spreadability and tactile feel, a somewhat reduced freedom to control the form and viscosity of the cosmetic material, and a propensity for solidification to occur regardless of the quantity of addition.

Art has also been developed with regard to gel-form silicone compositions, in which a silicone oil is gelled by using a polyether-modified silicone and water (Patent Document 7); however, a problem with this art has been its inadequate thickening•gelling effect when the oil system contains an organic oil. Another problem with respect to the tactile feel has been a slimy and uncomfortable sensation.

On the other hand, the art of oil gelation by, for example, an amino acid derivative-modified silicone or a straight-chain polyamide-modified silicone, and its application to cosmetic materials have also been reported (Patent Documents 8 to 11). While these gellants are excellent in terms of tactile feel, solidification is prone to occur regardless of the quantity of addition, which makes it difficult to freely control the form and viscosity of the cosmetic material. Moreover, due to an excessive solidification and hardening, once the gel surface has been scratched or damaged, recovery to a smooth surface cannot occur and the damage remains intact, which has the disadvantage of an impaired appearance.

Thus, the silicone-type oil gellants provided by the existing art are almost all of a type that ends up causing solidification of the oil, and an excellent oil thickener that makes possible free ranging control of, e.g., the form and viscosity of an oil or cosmetic material based on the quantity of thickener addition is unknown. Also unknown are a material and art that can stably thicken a wide variety of oil systems comprising a silicone oil+organic oil combination.

When one considers the existing art from the perspective of the involvement of (poly)glycerol-modified silicones with the oil thickening•gelation art, the following, for example, have been proposed: cosmetic materials comprising the combination of an organomodified-clay mineral or fructooligosaccharide fatty acid ester known as an oil thickener•gellant, with a silicone- and branched polyhydric alcohol-modified silicone, for example, an alkyl/branched linear siloxane/polyglycerol-co-modified silicone (Patent Documents 12 and 13) and a make-up cosmetic material that contains, in specific proportions, a silicic anhydride known as an oil thickener•gellant and an alkyl glyceryl ether-modified silicone with a specific structure (Patent Document 14).

The (poly)glycerol-modified silicones used in this art in all instances have a low molecular weight and, due to their poor oil thickening•gelation capacity, have had to be used in combination with a separate material that can effectively thicken•gel an oil and have also had an unsatisfactory effect with regard to controlling a cosmetic material to a required viscosity and state. In addition, in some cases the organo-modified-clay mineral or silicic anhydride undergoes aggregation due to the influence of the oil species or water fraction and the proposed cosmetic materials have thus had stability problems. The fructooligosaccharide fatty acid esters have an unsatisfactory capacity to thicken•gel silicone oils other than cyclic siloxanes and thus have provided little flexibility with regard to cosmetic material formulation.

A novel organopolysiloxane-glycerol derivative alternating copolymer has quite recently been proposed in Patent Document 15; here, a high molecular weight polyglycerol-modified silicone is obtained free of the problem of the turbidity induced by unreacted starting material. However, as may be understood from its chemical structure, this compound incorporates a hydrophilic group moiety in its main chain. As a consequence, its properties are completely different from those of the hydrophilic silicones heretofore in general use, such as polyether-modified silicones, and a corresponding art has thus been required for its stable incorporation into such fragile and nuanced formulations as cosmetic products and its field of use has therefore been limited. In addition, while this compound has a good compatibility with oils that are solely a silicone system, with mixed oil systems with an organic oil, phase separation has been prone to occur and this compound has thus been unable to manifest satisfactory effects.

The essential cause of these problems is intimately related to problems with the technology for producing the existing polyhydric alcohol-modified silicones. Thus, there is little freedom in the structural design of silicones modified by a polyhydric alcohol such as (poly)glycerol and production in stable qualities has been problematic. These polyhydric alcohol-modified silicones are typically produced by the addition to an organohydrogensiloxane of a polyhydric alcohol derivative that bears a reactive unsaturated group, but the residual polyhydric alcohol derivative is frequently poorly compatible with the copolymer reaction product. Separation into two phases then occurs a short time after production, which has been a major impediment to commercialization.

Moreover, due to the inherently poor compatibility between these polyhydric alcohol derivatives and organohydrogensiloxanes, the addition reaction frequently does not go to completion, even when a solvent is used, when the design molecular weight of the copolymer exceeds approximately 5000, thus making production of the target material highly problematic. Even at about 3000, unreacted material gradually separates•precipitates, which has required a process for its removal and has also been a major impediment from the standpoint of the production efficiency (Patent Documents 16 to 18).

Even when a hydroxyl-protected compound is employed as the polyhydric alcohol derivative, this necessitates deprotection after the completion of the reaction and as a consequence cannot avoid the previously noted problem of separation into two phases. In addition, severe conditions are required for the acid treatment for deprotection in this method, which causes cleavage of the silicone main chain; the desired product cannot then be obtained in good reproducibilities due to, e.g., the reduction in molecular weight (Patent Document 19).

A method of producing a branched polyglycerol-modified silicone is proposed in Patent Document 20, wherein the branched polyglycerol-modified silicone is obtained by the addition/graft polymerization of 2,3-epoxy-1-propanol in the presence of an acid or base catalyst to/on a silicone that has at least one functional group selected from the group consisting of the hydroxy group, carboxy group, amino group, imino group, mercapto group, and epoxy group. However, the siloxane main chain undergoes cleavage during graft polymerization in this method, which promotes the production of two or more components having different properties as the copolymer; this has frequently caused problems with regard to quality and the purification process.

For these reasons, the conventional polyhydric alcohol-modified silicones include few practical species, and, given the constraints on the production technology, most applied investigations have involved low molecular weight polyhydric alcohol-modified silicones. Excluding Patent Document 15, which is a block copolymer, no examples can be found of investigations of the application to cosmetic materials of high molecular weight polyglycerol-modified silicones with molecular weights above 15000. In particular, there have been no reports of the application to cosmetic materials of a high molecular weight silicone in which the side chain and/or terminal position—as opposed to the polysiloxane main chain—has been modified by a polyglycerol derivative.

On the other hand, white pigments as typified by titanium oxide and zinc oxide, colored pigments as typified by iron oxide red, and particulates such as mica and sericite are widely used in, for example, the field of cosmetic materials and most prominently basic cosmetics but also lipsticks, sunscreens, nail colors, nail coatings, foundations, mascaras, eye liners, and so forth. These powders are incorporated in cosmetic materials for the purpose, for example, of adjusting the color and covering power and/or adjusting the tactile feel, and examples of their use in oil-based cosmetic materials in combination with a conventional polyhydric alcohol-modified silicone have also been reported (Patent Documents 1 to 6 and 12 to 14).

However, particulate aggregation and sedimentation readily occurs with this art, and it has not been possible to provide the user with a fully satisfactory experience upon application to the skin due, for example, to uneven coating, an inadequate covering power, an unnatural color, and so forth. Moreover, since the polyhydric alcohol-modified silicones in use have a low molecular weight and exercise a poor oil thickening capacity, the effect with regard to cosmetic durability has also been unsatisfactory.

Among powders, silicone-type powders such as spherical organopolysiloxane elastomer powder, polymethylsilsesquioxane powder, silicone resin powder, and silicone rubber powder and organic resin powders such as silk powder, nylon powder, polymethyl methacrylate powder, and polyethylene powder exhibit an excellent oil-absorptive capacity for oils and as a consequence mitigate the strongly oily feel of oil-based cosmetics and have the effect of bringing the skin sensation after application closer to a natural impression. However, they are also difficult to uniformly disperse in a formulation, and another problem has been a conspicuous powdery sensation at increased levels of incorporation.

Accordingly, a requirement has existed for a material and/or a cosmetic material that makes possible the uniform and stable dispersion•immobilization of a powder or colorant in an oil-based cosmetic material and that makes possible the retention of an excellent cosmetic effect and a discomfort-free natural skin sensation for about 1 day after application to the skin.

Finally, the existing art related to silicone-containing gel-form cosmetic materials will be considered. Gel-form cosmetic materials evoke interest with regard to special features and effects that are based on their physical structure, and various investigations into gel-form cosmetic materials have been carried out to date. While also involving the oil thickening or gelation technology, cosmetic materials that assume a completely solidified state or that take the form of a low-viscosity liquid are frequently problematic with regard to ease of use, which may cause some limitations on their application. As a consequence, within the sphere of gel-form cosmetic materials, there have been requirements for cosmetic materials that have a viscosity and elasticity in the intermediate region between liquid and solid and for materials and technical developments that make possible the adjustment of cosmetic materials into such a state.

Accordingly, within the extensive oil thickening/gelation art, the art related to the gelatinous silicone composition of Patent Document 7, because it can bring about gelation or thickening over a broad range of silicone oils, which are oils that are quite frequently incorporated in cosmetic materials, and because of a superior composition stability over that provided by the use of a powder-based gellant, is widely utilized as a base for gel-form cosmetic materials or as a base for emulsified compositions and emulsified cosmetic materials (Patent Documents 21 to 26).

However, the polyether-modified silicone used by Patent Document 7 as a thickener•gellant requires water for gelation and the potential formulations are therefore limited. In addition, stickiness and a slimy and uncomfortable sensation are concerns depending on the particular quantity of incorporation. Another problem has been the poor thickening•gelling effect when an organic oil is present in the oil system.

Various oils other than silicone oils are used for cosmetic materials, e.g., hydrocarbon oils and ester oils, and combinations with these oils are frequently used in cosmetic material formulations in order, e.g., with regard to tactile feel, to exploit the respective advantages and compensate for respective shortcomings. Accordingly, there is demand for a gel-form cosmetic material that can maintain various oil systems comprising a silicone oil+organic oil combination in a gel state that has a viscoelasticity in the intermediate range between that of a liquid and solid. There is also demand for a gel-form cosmetic material that enables free-ranging control of the state and viscosity of the gel-form cosmetic material to be exercised based on the amount of thickener or gellant addition.

[Patent Document 1] JP 3,389,271 B (JP 06-157236 A)
[Patent Document 2] JP 3,513,682 B (JP 09-071504 A)
[Patent Document 3] JP 3,625,471 B (WO 2003/075864)
[Patent Document 4] JP 06-305933 A (JP 3,477,222 B)
[Patent Document 5] JP 07-025728 A (JP 3,160,427 B)
[Patent Document 6] JP 07-033622 A (JP 3,200,247 B)
[Patent Document 7] JP 3,333,782 B (JP 05-311076 A)
[Patent Document 8] JP 2004-182680 A
[Patent Document 9] U.S. Pat. No. 5,874,069
[Patent Document 10] U.S. Pat. No. 5,919,441
[Patent Document 11] U.S. Pat. No. 6,534,072
[Patent Document 12] JP 3,678,420 B (WO 2003/041664)
[Patent Document 13] JP 2004-231608 A
[Patent Document 14] JP 2005-194523 A
[Patent Document 15] JP 2005-042097 A
[Patent Document 16] JP 62-034039 B
[Patent Document 17] JP 3,976,226 B (JP 2002-179798 A)
[Patent Document 18] JP 2005-089494 A
[Patent Document 19] JP 06-089147 B (JP 1,956,013 B)
[Patent Document 20] JP 2004-339244 A
[Patent Document 21] JP 3,639,315 B (JP 07-100358 A)
[Patent Document 22] JP 3,407,770 B (JP 08-217626 A)
[Patent Document 23] JP 3,719,540 B (JP 09-194323 A)
[Patent Document 24] JP 3,580,384 B (JP 08-268831 A)
[Patent Document 25] JP 3,580,385 B (JP 08-268832 A)
[Patent Document 26] JP 3,313,043 B (JP 10-245317 A)

SUMMARY OF INVENTION

Technical Problems to be Solved

The present invention seeks to solve the problems identified above by providing an excellent thickener or gellant that exhibits an excellent compatibility for a variety of oil systems and that based on its quantity of addition can provide free-ranging control of the state and viscosity of oil material or a cosmetic material.

A second problem for the present invention is to provide an excellent dispersant and immobilizing agent that can uniformly and stably disperse and immobilize a powder or colorant in a oil material-based cosmetic material and that makes possible the persistence of an excellent cosmetic effect and a discomfort-free, natural skin sensation for approximately 1 day after application to the skin.

A third problem for the present invention is to provide a gel composition that constitutes a base for the stable and facile production of cosmetic materials having various viscoelasticities and states, e.g., a gel, a paste, a cream, an emulsified liquid, and so forth, and that can maintain various oils in a gel state that has a viscoelasticity in the intermediate range between a liquid and solid. This also includes the introduction of a stable gel composition that can exhibit various functionalities and that can be readily obtained by the admixture into the aforementioned composition of a powder or a component as ordinarily used in cosmetic materials, e.g., an ultraviolet absorber, a film-forming agent, a salt, and so forth.

A fourth problem for the present invention is to provide a method that, through the dilution of the aforementioned composition by mixing water thereinto, can readily yield a cosmetic material in a freely selectable form that exhibits a lower viscosity, e.g., a paste, cream, or liquid emulsion. This includes the introduction of a method that provides a topical agent in a freely selectable form by the incorporation in the aforementioned composition of water and a physiologically active substance.

Solution to Problems

The present inventors achieved the present invention as a result of intensive investigations directed to achieving the objects described above. That is, the objects of the present invention are achieved by a thickener or gellant for oil materials, wherein the thickener or gellant contains a high molecular weight organopolysiloxane that has a polyglycerol structure-containing hydrophilic group and that has a degree of polymerization for its organopolysiloxane chain of more than 200. The objects of the present invention are also achieved by a topical agent and a cosmetic material that contain this thickener or gellant. The objects of the present invention are also achieved by a method of producing a topical agent or cosmetic material using the indicated thickener or gellant for a oil material or using a gel composition.

The objects are more preferably achieved by a thickener or gellant for oil materials and by a gel-form cosmetic material wherein the thickener, gellant, or gel-form cosmetic material contains a hydrophilic high molecular weight organopolysiloxane that has a tetraglycerol structure-containing hydrophilic group, that additionally has a siloxane chain and long-chain hydrocarbyl group in side chain position, and that has a degree of polymerization for its organopolysiloxane chain of more than 300.

The objects are also preferably achieved by a thickener or gellant that contains (B) a powder or a colorant and (C) at least one selection from the group consisting of silicone-type surfactants excluding those that correspond to component (A), crosslinked organopolysiloxanes, silicone resins, acrylic silicone resins, acrylic silicone dendrimer copolymers, polyamide-modified silicones, alkyl-modified silicone resin waxes, and organic surfactants.

More specifically, the first object of the present invention is achieved by a thickener or gellant for a oil material, wherein the thickener or gellant contains an organopolysiloxane that has a polyglycerol structure-containing hydrophilic group Q and that is represented by the following structural formula (1):

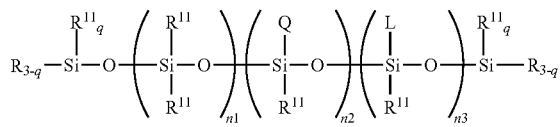

(1)

and is also achieved by a topical agent and particularly a cosmetic material that contain this thickener or gellant.

In structural formula (1), $R^{11}$ is a substituted or unsubstituted $C_{1-30}$ monovalent hydrocarbyl group or is the hydrogen atom, and L is a chain organosiloxane group represented by the following structural formula (2-1) or (2-2).

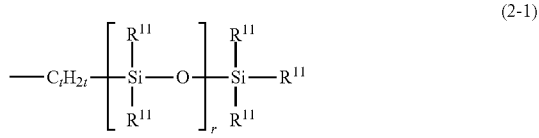

(2-1)

wherein $R^{11}$ is a group as defined above, t is a number in the range from 2 to 10, and r is a number in the range from 1 to 100

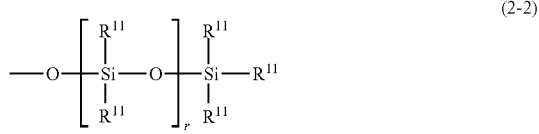

(2-2)

wherein $R^{11}$ is a group as defined above and r is a number in the range from 1 to 100

Q in structural formula (1) is a polyglycerol structure-containing hydrophilic group that is bonded to the silicon atom across at least divalent linker group and that contains at least one type of hydrophilic unit selected from hydrophilic units represented by the following structural formulas (3-1) to (3-3).

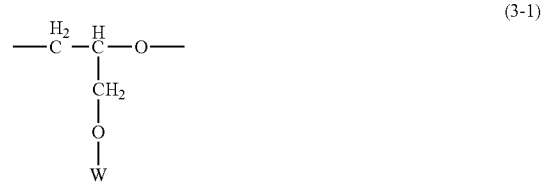

(3-1)

wherein W is the hydrogen atom or a $C_{1-20}$ alkyl group

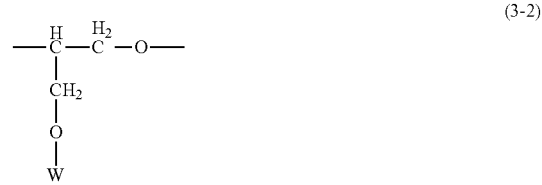

(3-2)

wherein W is the same group as defined above

(3-3)

In structural formula (1), R is a group selected from L and Q; n1, n2, and n3 are numbers in the ranges $200 \leq n1 \leq 1000$, $0 \leq n2 \leq 20$, and $0 \leq n3 \leq 50$; and q is an integer in the range from 0 to 3. However, when n2=0, q is an integer in the range from 1 to 3 and at least one R is Q.

The previously indicated objects are more preferably achieved by a thickener or gellant and a gel-form cosmetic material that contain a high molecular weight hydrophilic organopolysiloxane that is represented by the following structural formula (1-1), that has as a hydrophilic group ($Q^1$) therein a hydrophilic group derived from polyglycerol and particularly preferably a tetraglycerol structure-containing group, and that has values for n1', n2', and n3', which are the degrees of polymerization of the below-indicated organosiloxane units, in the ranges given below.

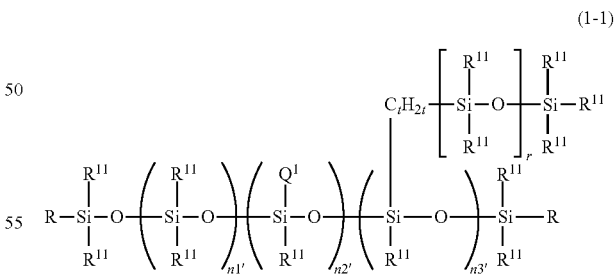

(1-1)

In structural formula (1-1), $R^{11}$ is a group as defined above; t and r are the same numbers as defined above; R is $R^{11}$ or $Q^1$; and $Q^1$ is a hydrophilic group derived from a polyglycerol and given by the following structural formula (4-1-1)

$R^{3'}$—O—$X^1{}_m$—$R^4$   (4-1-1)

wherein $R^{3'}$ is a divalent organic group; each $X^1$ is independently at least one type of hydrophilic unit selected from the hydrophilic units given by the following structural formulas (3-1-1) to (3-3-1); m is a number in the range from 3 to 5; and $R^4$ is a group selected from the group consisting of the hydrogen atom, $C_{1-20}$ alkyl, acyl groups, and the glycidyl group.

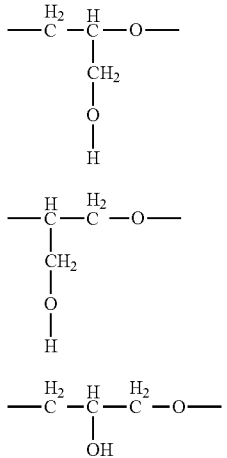

(3-1-1)

(3-2-1)

(3-3-1)

$n1'$, $n2'$, and $n3'$ are numbers in the ranges $300 \leq n1' \leq 1000$, $1 \leq n2' \leq 20$, and $1 \leq n3' \leq 20$.

Considered in greater detail, the previously indicated objects are achieved by the invention of a thickener or gellant for a oil material, wherein the thickener or gellant contains an organopolysiloxane that has a polyglycerol structure-containing group (Q), and are thus achieved by "[1] A thickener or gellant for oil materials, wherein the thickener or gellant comprising (A) an organopolysiloxane that has a polyglycerol structure-containing hydrophilic group Q and that is represented by the previously indicated structural formula (1).

[2] The thickener or gellant according to [1], wherein each Q in structural formula (1) is independently a polyglycerol structure-containing hydrophilic group that is bonded to the silicon atom across an at least divalent linker group and in which at least one type of hydrophilic unit selected from the hydrophilic units represented by the preceding structural formulas (3-1) to (3-3) is connected in straight-chain form, or a polyglycerol structure-containing hydrophilic group that is bonded to the silicon atom across an at least divalent linker group, that contains at least two of the at least one type of hydrophilic unit selected from the hydrophilic units represented by the preceding structural formulas (3-1) to (3-3), and that has a branching unit selected from groups represented by the following structural formulas (3-5) to (3-7).

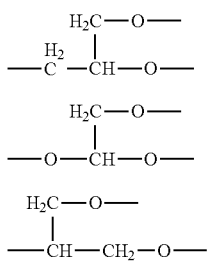

(3-5)

(3-6)

(3-7)

[3] The thickener or gellant according to [1] or [2], characterized in that the hydrophilic group Q is a polyglycerol structure-containing hydrophilic group represented by the following structural formula (4-1), (4-2), (4-3), or (4-4)

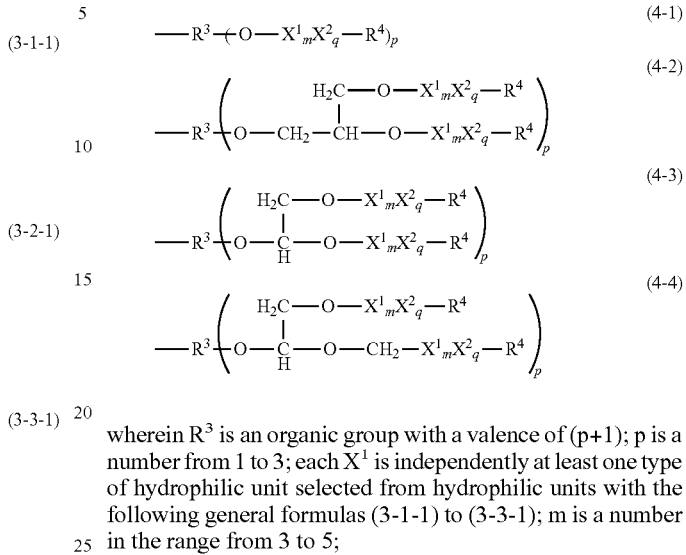

wherein $R^3$ is an organic group with a valence of $(p+1)$; p is a number from 1 to 3; each $X^1$ is independently at least one type of hydrophilic unit selected from hydrophilic units with the following general formulas (3-1-1) to (3-3-1); m is a number in the range from 3 to 5;

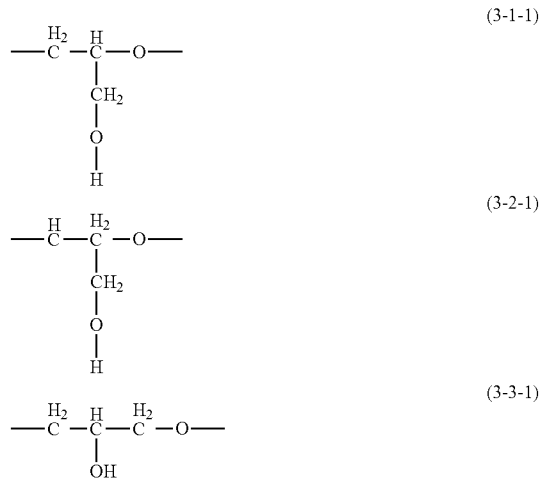

(3-1-1)

(3-2-1)

(3-3-1)

$X^2$ is a hydrophilic unit represented by the following structural formula (3-4-1); q is a number in the range from 0 to 50; the bonding configuration for each of $X^1$ and $X^2$ is independently a block configuration or a random configuration;

—$C_rH_{2r}$—O—   (3-4-1)

wherein r is a number in the range from 1 to 6 and $R^4$ is a group selected from the group consisting of the hydrogen atom, $C_{1-20}$ alkyl, acyl groups, and the glycidyl group.

[4] The thickener or gellant for oil materials according to any of [1] to [3], characterized in that each hydrophilic group Q is independently a hydrophilic group derived from a polyglycerol and given by the following structural formula (4-1-1)

$R^{3'}$—O—$X^1{}_m$—$R^4$   (4-1-1)

wherein $R^{3'}$ is a divalent organic group; each $X^1$ is independently at least one type of hydrophilic unit selected from hydrophilic units with the previously described general formulas (3-1-1) to (3-3-1); m is a number in the range from 3 to 5; and $R^4$ is a group selected from the group consisting of the hydrogen atom, $C_{1-20}$ alkyl, acyl groups, and the glycidyl group.

[5] The thickener or gellant according to any of [1] to [4], characterized in that the hydrophilic group Q is a hydrophilic group derived from tetraglycerol.

[6] The thickener or gellant according to any of [1] to [5], that is characteristically given by the following structural formula (1-1):

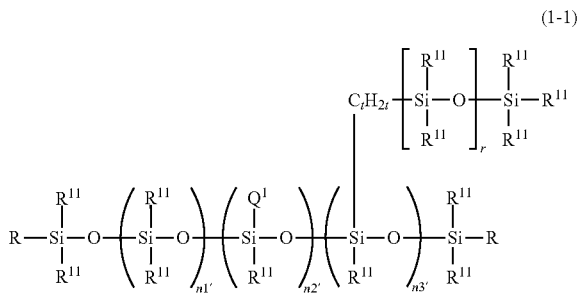

wherein $R^{11}$ is a group as defined above; t and r are the same numbers as defined above; $Q^1$ is a hydrophilic group derived from a polyglycerol and given by the preceding structural formula (4-1-1); n1', n2', and n3' are numbers in the ranges $300 \le n1' \le 1000$, $1 \le n2' \le 20$, and $1 \le n3' \le 20$; and R is $R^{11}$ or $Q^1$.

[7] The thickener or gellant according to [6], characterized in that the hydrophilic group $Q^1$ in structural formula (1-1) is a hydrophilic group derived from tetraglycerol.

[8] The thickener or gellant according to any of [1] to [7], that further comprise (B) a powder or a colorant.

The thickener or gellant according to any of [1] to [8], that further comprise (C) at least one selected from the group consisting of silicone-type surfactants excluding those that correspond to component (A), crosslinked organopolysiloxanes, silicone resins, acrylic silicone resins, acrylic silicone dendrimer copolymers, polyamide-modified silicones, alkyl-modified silicone resin waxes, and organic surfactants.

[10] The thickener or gellant according to any of [1] to [9], wherein the oil material is (D1) at least one oil selected from solid oils, paste oils, silicone oils, hydrocarbon oils, and ester oils.

[11] The thickener or gellant according to [8], wherein component (B) is (B1) at least one powder or colorant selected from the group consisting of silicone resin powders, silicone rubber powders, organic resin powders excluding silicone resin powders, organomodified clay minerals, titanium oxide, zinc oxide, titanium mica, metal soaps, inorganic pigments, and inorganic colored pigments.".

The objects of the present invention are also achieved by the invention of a gel composition comprising the organopolysiloxane described above and are thus achieved by "[12] A gel composition comprising 30 to 80 mass % of (D) oil material, 10 to 70 mass % of the thickener or gellant according to any of claims 1 to 11, 0 to 20 mass % of (E) at least one compound selected from the group consisting of lower monohydric alcohols and organic polyhydric alcohol compounds, and 0 to 20 mass % of (F) water.

[13] The gel composition according to [12], that further comprises (G) an ultraviolet absorber.

[14] The gel composition according to [12] or [13], that further comprises (H) at least one compound selected from sucrose fatty acid esters and polyglycerol fatty acid esters.

[15] The gel composition according to any of [12] to [14], that further comprises (I) an organic film-forming agent.

[16] The gel composition according to any of [12] to [15], that further comprises (J) at least one compound selected from the group consisting of amino acids and/or their salts, inorganic salts, organic acids and/or their salts, and water-soluble polymers.".

The objects of the present invention are suitably achieved by the invention of a cosmetic material that characteristically comprises the previously described thickener or gellant or the previously described gel composition, the invention of a topical agent that characteristically comprises the previously described thickener or gellant or the previously described gel composition and that further comprises a physiologically active substance, and the invention of methods of producing this cosmetic material and topical agent, and are thus achieved by "[17] A method of producing a cosmetic material, comprising:
By mixing 100 mass parts of the gel composition according to any of [12] to [16] with 0.1 to 4,000 mass parts of (F) water.

[18] A cosmetic material obtained by mixing 100 mass parts of the gel composition according to any of [12] to [16] with 0.1 to 4,000 mass parts of (F) water.

[19] A gel-form cosmetic material comprising 30 to 80 mass % of (D) oil material, to 60 mass % of the thickener or gellant according to claim 8 or 11, and 0 to 20 mass % of (F) water.

[20] A method of producing a topical agent, comprising:
By mixing 100 mass parts of the gel composition according to any of [12] to [16], 0.1 to 4,000 mass parts of (F) water, and 0.001 to 1.0 mass part of (L) a physiologically active substance.

[21] A topical agent obtained by mixing 100 mass parts of the gel composition according to any of [12] to [16], 0.1 to 4,000 mass parts of (F) water, and 0.001 to 1.0 mass part of (L) a physiologically active substance.

[22] A topical gel comprising 30 to 80 mass % of (D) oil material, 20 to 60 mass % of the thickener or gellant according to [8] or [11], 0 to 20 mass % of (E) at least one compound selected from the group consisting of lower monohydric alcohols and organic polyhydric alcohol compounds, 0 to 20 mass % of (F) water, and 0.001 to 1.0 mass % of (L) a physiologically active substance

[23] The topical agent according to [21] or [22], wherein (L) the physiologically active substance is at least one physiologically active substance selected from the group consisting of antiinflammatories, ageing inhibitors, whiteners, hair-restoring agents, hair-growth agents, circulation promoters, antibacterials, antiseptics, vitamins, wound-healing promoters, anti-irritants, analgesics, cell activators, and enzymes.".

In addition, the objects of the present invention are suitably achieved by the invention of a hair cosmetic and a hair-setting agent composition that comprises the thickener or gellant as described above and are also suitably achieved by the free-ranging selection of the form or state, e.g., liquid and so forth, for the cosmetic and topical agent and particularly for the hair cosmetic and the hair-setting agent composition. That is, the objects of the present invention are achieved by "[24] A hair cosmetic that characteristically comprises the thickener or gellant according to any of [1] to [11] and (N) a cationic surfactant.

[25] A hair-setting agent composition that characteristically comprises the thickener or gellant according to any of [1] to [11] and (P) an organic film-forming polymer.

[26] The cosmetic material according to [18] or [19], wherein the product form is a liquid, a liquid emulsion, a cream, a solid, a paste, a gel, a powder, a multilayer form, a mousse, or a spray.
[26-1] The cosmetic material according to [26], that characteristically is a hair cosmetic.
[26-2] The cosmetic material according to [26], that characteristically is a hair-setting agent composition.
[27] The topical agent according to any of [21] to [23], wherein the product form is a liquid, a liquid emulsion, a cream, a solid, a paste, a gel, a powder, a multilayer form, a mousse, or a spray.
[28] The hair cosmetic according to [24], wherein the product form is a liquid, a liquid emulsion, a cream, a solid, a paste, a gel, a powder, a multilayer form, a mousse, or a spray.
[29] The hair-setting agent composition according to [25], wherein the product form is a liquid, a liquid emulsion, a cream, a solid, a paste, a gel, a powder, a multilayer form, a mousse, or a spray.".

The objects of the present invention are also suitably achieved by a method of producing the previously described thickener or gellant by a hydrosilylation reaction between an organopolysiloxane having silicon-bonded hydrogen atom and another starting material. This production method is specifically described by
"[30] A method of producing the thickener or gellant according to any of [1] to [7], characterized by addition reacting at least
(A') an organohydrogenpolysiloxane that contains silicon-bonded hydrogen and that has a degree of polymerization of more than 200 and
(K) a polyglycerol structure-containing hydrophilic compound that has one alkenyl group wherein the alkenyl group resides in terminal position on the molecular chain and that contains at least one type of hydrophilic unit selected from the hydrophilic units given by the previously described structural formulas (3-1) to (3-3) in the presence of
(M) a hydrosilylation reaction catalyst.
[31] A method of producing the thickener or gellant according to [6] or [7], characterized by addition reacting at least
(A') an organohydrogenpolysiloxane that contains silicon-bonded hydrogen and that has a degree of polymerization of more than 300,
a chain organopolysiloxane given by general formula (2') below, that has one carbon-carbon double bond wherein the carbon-carbon double bond resides in terminal position on the molecular chain, and
(K1) a polyglycerol structure-containing hydrophilic compound that has one alkenyl group wherein the alkenyl group resides in terminal position on the molecular chain and that contains within the molecule at least one type of hydrophilic unit selected from the hydrophilic units given by structural formulas (3-1-1) to (3-3-1)
in the presence of
(M) a hydrosilylation reaction catalyst

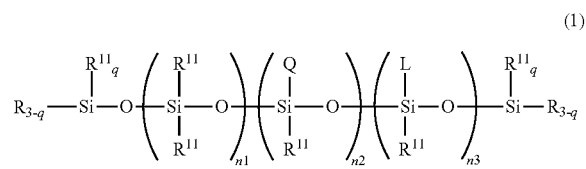

wherein $R^{11}$ is the same as described above, s is a number in the range from 0 to 8, and r is a number in the range from 1 to 100.".

Advantageous Effects of Invention

With respect to the problems described in "Problems to Be Solved by the Invention", the first problem for an oil thickener, which relates to the freedom provided to control the form of the oil material, the second problem, which relates to the dispersion and immobilization of a powder or colorant, the third problem, which relates to a gel composition, and the fourth problem, which relates to methods of producing a cosmetic material and a topical agent, all are suitably solved by the present invention.

BEST MODE FOR CARRYING OUT THE INVENTION

The material thickener or gellant according to the present invention characteristically contains a high molecular weight organopolysiloxane that has a polyglycerol structure-containing hydrophilic group and a degree of polymerization of more than 200 for its organopolysiloxane chain. In addition, the thickener or gellant according to the present invention preferably contains a high molecular weight organopolysiloxane that has as the aforementioned hydrophilic group a tetraglycerol structure-containing hydrophilic group, that has an organosiloxane chain in side chain position, and that has a degree of polymerization of more than 300 for its organopolysiloxane chain.

This organopolysiloxane is specifically an organopolysiloxane that has at least one polyglycerol structure-containing hydrophilic group Q in its molecule, that is represented by the following structural formula (1), $$R_{3-q}-\underset{\underset{R^{11}}{|}}{\overset{R^{11}_q}{|}}Si-O\left(\underset{\underset{R^{11}}{|}}{\overset{R^{11}}{|}}Si-O\right)_{n1}\left(\underset{\underset{R^{11}}{|}}{\overset{Q}{|}}Si-O\right)_{n2}\left(\underset{\underset{R^{11}}{|}}{\overset{L}{|}}Si-O\right)_{n3}\underset{\underset{R^{11}}{|}}{\overset{R^{11}_q}{|}}Si-R_{3-q} \quad (1)$$

and that has a degree of polymerization of more than 200 for the polysiloxane constituting its main chain.

$R^{11}$, L, Q, and n1, n2, and n3 in general formula (1) will be specifically described first.

$R^{11}$ in structural formula (1) is a substituted or unsubstituted $C_{1-30}$ monovalent hydrocarbyl group or is the hydrogen atom. These substituted and unsubstituted monovalent hydrocarbyl groups can be specifically exemplified by saturated aliphatic hydrocarbyl groups such as methyl, ethyl, propyl, butyl, pentyl, hexyl, heptyl, octyl, decyl, dodecyl, tetradecyl, hexadecyl, and octadecyl; saturated alicyclic hydrocarbyl groups such as cyclopentyl and cyclohexyl; aromatic hydrocarbyl groups such as phenyl, tolyl, xylyl, and naphthyl; and groups provided by replacing at least a portion of the carbon-bonded hydrogen in the preceding groups with, for example, a halogen atom such as fluorine or with an organic group containing, for example, the epoxy group, acyl group, carboxyl group, amino group, methacrylic group, mercapto group, or an ester group.

With the intention of imparting additional functionality to the organopolysiloxane according to the present invention, a modifying group other than the chain organosiloxane group (-L) and the polyglycerol structure-containing hydrophilic group (-Q) can be introduced or designed for $R^{11}$. Thus, when $R^{11}$ is a substituted monovalent hydrocarbyl group, an organic group as exemplified above can be selected as appropriate for this substituent in conformity with the characteristics to be imparted and the application. For example, when use for a cosmetic ingredient is contemplated, a monovalent hydrocarbyl group substituted by, e.g., an amino group, aminoethylaminopropyl group, carboxyl group, and so forth, can be selected with the goal of, for example, improving the use sensation, tactile feel, and/or persistence. Similarly, when the goal is the tactile feel on the skin and use sensation exhibited by so-called medium-chain alkyl groups or long-chain alkyl groups or when the goal is to improve the affinity with other components, $C_{8-20}$ alkyl can be selected for a portion of $R^{11}$ in addition to $C_{1-4}$ alkyl such as methyl and ethyl.

$R^{11}$ is particularly preferably a $C_{1-20}$ monovalent hydrocarbyl group or monovalent fluorinated hydrocarbyl group. The aliphatically unsaturated bond-free monovalent hydrocarbyl groups encompassed by $R^{11}$ can be exemplified by alkyl groups such as methyl, ethyl, propyl, butyl, pentyl, and hexyl; aryl groups such as phenyl, tolyl, and xylyl; and aralkyl groups such as benzyl. The monovalent fluorinated hydrocarbyl groups encompassed by $R^{11}$ can be exemplified by perfluoroalkyl groups such as trifluoropropyl and pentafluoroethyl. Viewed from an industrial perspective, $R^{11}$ is preferably methyl, ethyl, or phenyl and in particular from 90 to 100 mol % of the total $R^{11}$ is preferably a group selected from methyl, ethyl, and phenyl.

The group represented by L in structural formula (1) is a chain organosiloxane group as represented by the following structural formula (2-1) or (2-2), and it is a functional group that is optionally present in the organopolysiloxane according to the present invention. However, this chain organosiloxane group is a functional group that provides water repellency, and, due to the good balance of the combination with the hydrophilic group -Q, this chain organosiloxane group can further improve the thickening effect and gelation performance exercised by the organopolysiloxane according to the present application on oil components. Moreover, this chain organosiloxane group is a chemically stable functional group and as a consequence offers the advantage of being able to provide the desirable characteristic of making possible use in combination with a broad range of cosmetic components.

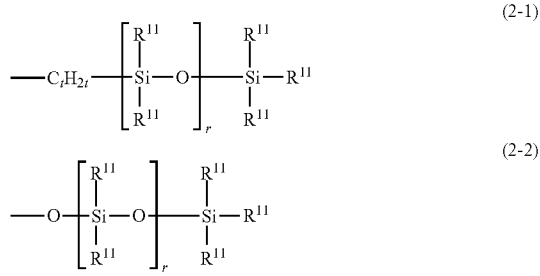

$R^{11}$ in structural formulas (2-1) and (2-2) is a group as defined above and is preferably a $C_{1-6}$ alkyl group or the phenyl group. This $C_{1-6}$ alkyl group can be exemplified by straight-chain, branched-chain, and cyclic alkyl groups such as methyl, ethyl, n-propyl, i-propyl, n-butyl, i-butyl, s-butyl, pentyl, neopentyl, cyclopentyl, and hexyl, wherein methyl and phenyl are particularly preferred for $R^{11}$.

r in structural formulas (2-1) and (2-2) is a number in the range from 1 to 100 and is preferably a number in the range from 2 to 50 and more preferably in the range from 3 to 20.

t in structural formula (2-1) is a number in the range from 2 to 10, and the group given by $C_tH_{2t}$ is a $C_{2-10}$ alkylene group. This alkylene group can be exemplified by straight-chain alkylene groups such as ethylene, propylene, butylene, and hexylene, and by branched alkylene groups such as methylmethylene, methylethylene, 1-methylpentylene, and 1,4-dimethylbutylene, wherein this alkylene group is preferably a group selected from ethylene, propylene, methylethylene, and hexylene.

The group represented by L in structural formula (1) is particularly preferably a chain organosiloxane group given by

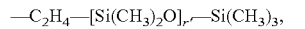

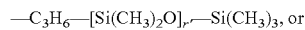

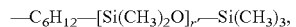

and the organopolysiloxane according to the present invention preferably contains at least one group L. r' in the formulas is a group in the range from 3 to 20.

Q in general formula (1) is a polyglycerol structure-containing hydrophilic group and is defined as a hydrophilic group that is bonded to the silicon atom through an at least divalent linker group and that contains at least one type of hydrophilic unit selected from the hydrophilic units given by the following structural formulas (3-1) to (3-3). This hydrophilic group Q is the moiety that imparts hydrophilicity to the organopolysiloxane according to the present application and as a general matter is a functional group derived from a polyglycerol compound that has an unsaturated group. A preferred example of the thusly defined Q is a functional group derived from a polyglycerol compound wherein the molecular chain terminals of the polyglycerol compound may be partially capped by hydrocarbon. Viewed from the perspective of the thickening and gelling effects on oils, a tetraglycerol structure-containing hydrophilic group is particularly preferred for Q in the invention of the present application.

This Q is specifically a polyglycerol structure-containing hydrophilic group that is bonded to the silicon atom across an at least divalent linker group and that contains at least one type of hydrophilic unit selected from the hydrophilic units represented by the following structural formulas (3-1) to (3-3).

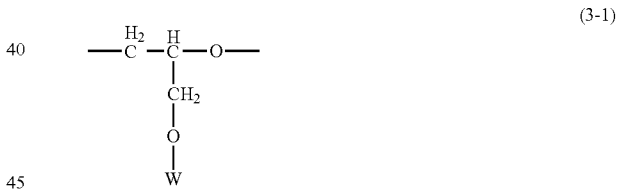

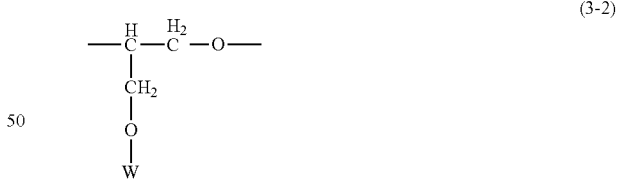

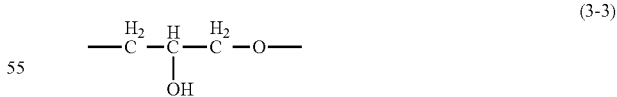

In formulas (3-1) to (3-3), W is the hydrogen atom or a $C_{1-20}$ alkyl group and is preferably the hydrogen atom. When, in particular, W is the hydrogen atom, this accrues the advantage of being very environmentally friendly due to resistance to oxidation in air, which results in a resistance to the production with elapsed time in storage of allergenic compounds such as aldehydes, e.g., formaldehyde, and formate esters.

Each of these hydrophilic units with structural formulas (3-1) to (3-3) is a hydrophilic unit in a hydrophilic group derived from a hydrophilic compound selected mainly from polyhydric alcohols including glycerol, polyglycerols, polyglycidyl ethers, and compounds provided by the partial capping of the terminal hydroxyl in the preceding with a hydrocarbyl group.

Q in structural formula (1) can be exemplified by a polyglycidyl ether group or polyglycerol group that has a straight-chain structure or a partially branched structure and that may contain a polyoxyalkylene group.

More specifically, Q is a polyglycerol structure-containing hydrophilic segment that is bonded to the silicon atom by an at least divalent linker group and that has at least one type of hydrophilic unit selected from the hydrophilic units with structural formulas (3-1) to (3-3) bonded in a straight-chain configuration. Similarly, Q may be a polyglycerol structure-containing hydrophilic segment that is bonded to the silicon atom by an at least divalent linker group, that has at least one of the at least one type of hydrophilic unit selected from the hydrophilic units with structural formulae (3-1) to (3-3), and that has a branching unit selected from the groups represented by the following structural formulae (3-5) to (3-7).

$$H_2C-O- \atop -C^{H_2}-CH-O- \qquad (3\text{-}5)$$

$$H_2C-O- \atop -O-CH-O- \qquad (3\text{-}6)$$

$$H_2C-O- \atop -CH-CH_2-O- \qquad (3\text{-}7)$$

In these structural formulae (3-5) to (3-7), there is bonded to each of the two oxygen atoms, considered independently, at least one type of hydrophilic unit selected from the hydrophilic units given by the previously indicated general formulas (3-1) to (3-3). This hydrophilic unit may be further bonded to a branching unit selected from the groups given by structural formulas (3-5) to (3-7) to form a dendritic polyglycerol structure in which the hydrophilic unit is branched into a plurality of generations. As an example, the structure of a dendritically branched hydrophilic group Q is provided below, in which one branching unit with structural formula (3-5) and two branching units with structural formula (3-7) are present; however, the dendritic polyglycerol structure is not limited to this.

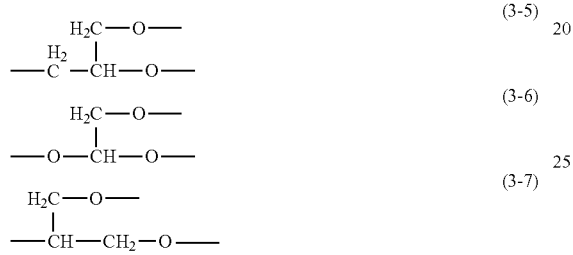

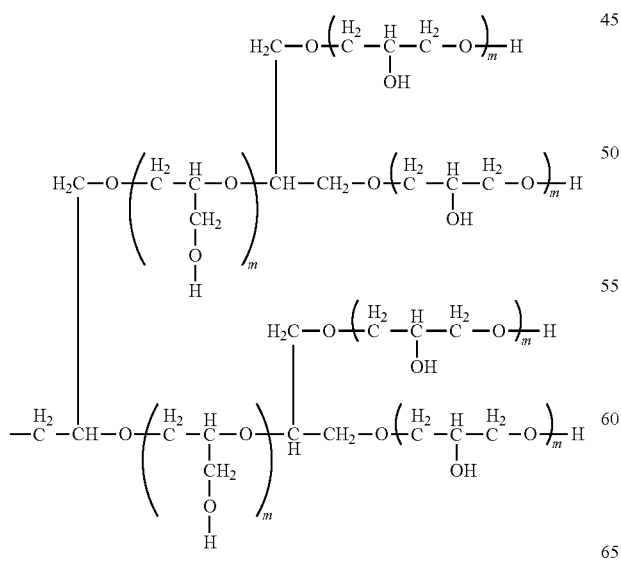

wherein m is a number in the range from 1 to 50

The at least divalent linker group is the moiety of the hydrophilic group Q that bonds to the silicon atom, and its structure is not particularly limited. It can be exemplified by alkylene groups such as ethylene, propylene, butylene, and hexylene; alkylenephenylene groups such as ethylenephenylene and propylenephenylene; alkylenearalkylene groups such as ethylenebenzylene; alkyleneoxyphenylene groups such as ethyleneoxyphenylene and propyleneoxyphenylene; alkyleneoxybenzylene groups such as methyleneoxybenzylene, ethyleneoxybenzylene, and propyleneoxybenzylene; and the groups given below. There may be from 0 to 3 ether linkages in the at least divalent linker group, and there is more preferably 0 or 1.

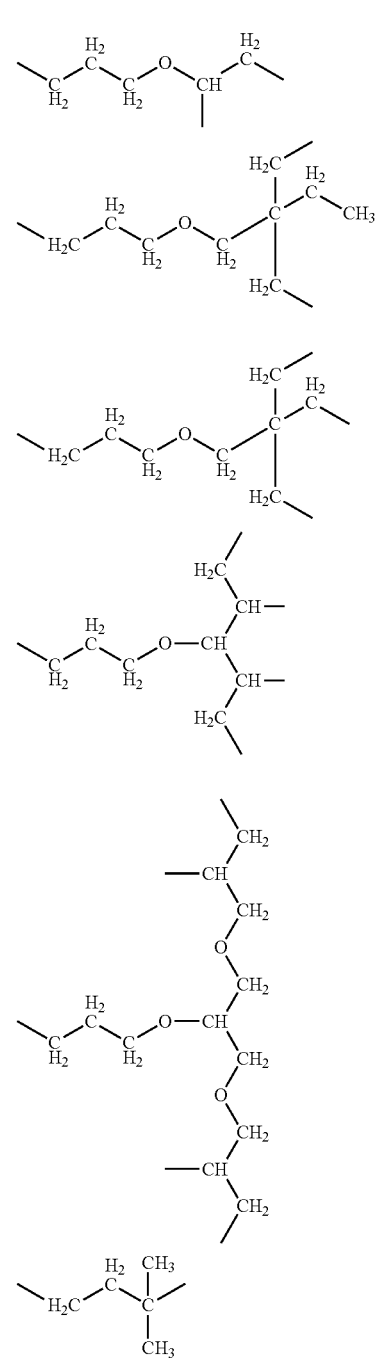

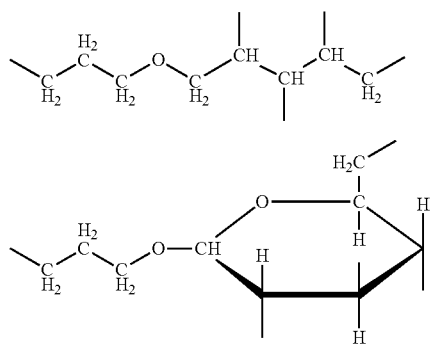

Q is more preferably a hydrophilic group as given by the following structural formulas (4-1) to (4-4), which are hydrophilic groups derived from polyglycerol-type compounds.

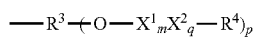 (4-1)

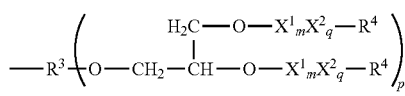 (4-2)

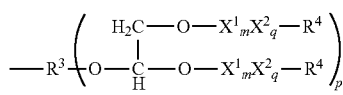 (4-3)

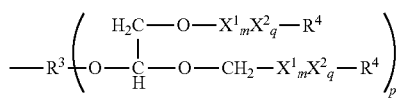 (4-4)

$R^3$ in formulas (4-1) to (4-4) is a (p+1)-valent organic group and p is a number greater than or equal to 1 and less than or equal to 3. This $R^3$ can be exemplified by the same groups as for the previously described at least divalent linker group.

p is particularly preferably 1, and a group selected from the divalent organic groups given by the following general formulas is a preferred example of $R^3$

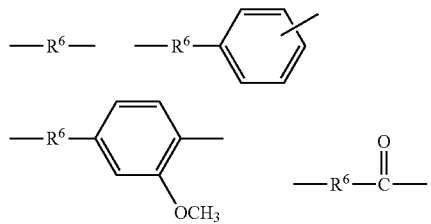

wherein each $R^6$ is independently a possibly substituted $C_{2-22}$ straight-chain or branched-chain alkylene group, an alkenylene group, or a $C_{6-22}$ arylene group.

Each $X^1$ is independently at least one type of hydrophilic unit selected from the hydrophilic units with the following general formulas (3-1-1) to (3-3-1), and m is a number in the range from 3 to 5 and particularly preferably is 4.

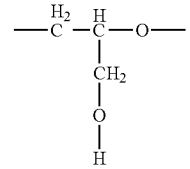 (3-1-1)

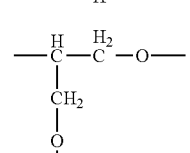 (3-2-1)

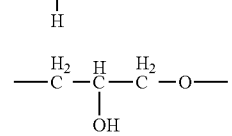 (3-3-1)

$X^2$ is an oxyalkylene unit represented by the following structural formulae (3-4-1)

$$—C_rH_{2r}—O—$$ (3-4-1)

wherein r is a number in the range from 1 to 6, and q is a number in the range from 0 to 50, wherein $X^2$ is preferably the oxyethylene unit or oxypropylene unit. When $X^2$'s are bonded consecutively, they may then also be present in Q as at least one polyoxyalkylene unit with formula (3-4-2).

$$—(C_2H_4O)_{t1}(C_3H_6O)_{t2}—$$ (3-4-2)

t1 and t2 in this formula are each independently a number greater than or equal to 0, wherein (t1+t2) is a number in the range from 0 to 80 and preferably is a number in the range from 0 to 50.

The bonding configuration for $X^1$ and $X^2$ may be block or random. Thus, the hydrophilic group Q may be a hydrophilic group in which a hydrophilic segment comprising a polyoxyalkylene unit is bonded with a hydrophilic segment in which a hydrophilic unit with the previously described general formula (3-1-1) to (3-3-1) is bonded in a block configuration, or may be a hydrophilic group in which the units constituting the preceding are randomly bonded. An example is the $—X^1—(X^2)_{m1}—X^1—(X^2)_{m2}—$ bonding scheme.

$R^4$ is a group selected from the group consisting of the hydrogen atom, $C_{1-20}$ alkyl, acyl groups, and the glycidyl group.

Viewed from the perspective of the thickening effect and gelation performance exercised by the organopolysiloxane according to the present invention for oil components, a hydrophilic group derived from a polyglycerol and represented by the following structural formula (4-1-1) is a particularly preferred hydrophilic group Q.

$$—R^{3'}—O—X^1_m—R^4$$ (4-1-1)

$R^{3'}$ in the preceding formula is a divalent organic group and can be exemplified by the same groups as described above. $X^1$ and $R^4$ are the same groups as described above, and m is a number in the range from 3 to 5. In a particularly preferred embodiment, m is 4 and a tetraglycerol structure is present.

Viewed from the perspective of the thickening effect and gelation performance exercised by the organopolysiloxane according to the present invention for oil components, the aforementioned hydrophilic group Q is most preferably a hydrophilic group derived from a polyglycerol-type compound and in particular is a hydrophilic group derived from tetraglycerol. A specific example is a hydrophilic group derived from a tetraglycerol structure-containing polyglycerol-type compound that is a polyglycerol monoallyl ether or polyglyceryl eugenol.

The organopolysiloxane according to the invention of the present application has a degree of polymerization for its organosiloxane unit characteristically of more than 200 and more preferably of more than 300. More specifically, n1, n2, and n3 in structural formula (1) are numbers in the ranges $200 \leq n1 \leq 1000$, $0 \leq n2 \leq 20$, and $0 \leq n3 \leq 50$ and q is an integer in the range from 0 to 3. R is a group selected from L and Q. However, when n2=0, q is an integer in the range from 1 to 3 and at least one R is Q.

Viewed from the perspective of the thickening effect and gelation performance for oil components exercised by the organopolysiloxane according to the present invention, n1 is preferably a number in the range $250 \leq n1 \leq 1000$ and more preferably is a number in the range $300 \leq n1 \leq 1000$. Similarly, because the organopolysiloxane according to the invention of the present application preferably has at least one hydrophilic group -Q and at least one chain organosiloxane group -L in side chain position, n2 and n3 are numbers in the ranges, respectively, preferably of $1 \leq n2 \leq 20$ and $1 \leq n3 \leq 20$ and more preferably of $3 \leq n2 \leq 20$ and $3 \leq n3 \leq 20$. The molecular weight of the organopolysiloxane is established as a matter of principle by its structural formula, but considered in particular from the standpoint of the gelation performance an organopolysiloxane with a molecular weight exceeding 15,000 is preferred and a high molecular weight organopolysiloxane with a molecular weight in the range from 20,000 to 75,000 is particularly preferred.

Viewed from the perspective of the thickening effect and gelation performance for oil components exercised by the organopolysiloxane according to the present invention, an organopolysiloxane with the following structural formula (1-1) is a particularly suitable example of the organopolysiloxane with structural formula (1).

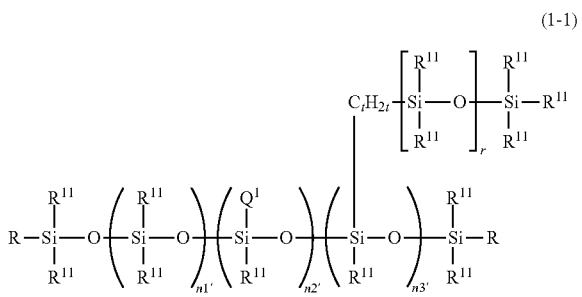

(1-1)

$R^{11}$ in the preceding formula is the same group as defined above. t and r are the same numbers as defined above. $Q^1$ is a hydrophilic group derived from a polyglycerol and represented by the preceding structural formula (4-1-1) and in particular is preferably a tetraglycerol structure-containing hydrophilic group. n1', n2', and n3' are numbers in the ranges $300 \leq n1' \leq 1000$, $1 \leq n2' \leq 20$, and $1 \leq n3' \leq 20$. 90 to 100 mol % of the total $R^{11}$ is preferably a group selected from methyl, ethyl, and phenyl; however, with the goal of designing a co-modified organopolysiloxane that exhibits even greater functionality, a long-chain alkyl group or a monovalent hydrocarbyl group in which a portion of the carbon-bonded hydrogen has been replaced by a halogen atom such as fluorine or by another organic group can be and preferably is selected for a portion of $R^{11}$. In addition, hydrogen (—H) bonded to the Si atom may be present for a portion of $R^{11}$. R is a group selected from $R^{11}$ and $Q^1$.

The hereinabove-described organopolysiloxane according to the present application can be obtained by addition reacting an organohydrogenpolysiloxane that contains silicon-bonded hydrogen with a polyglycerol structure-containing hydrophilic compound that has one carbon-carbon double bond wherein the carbon-carbon double bond resides at one terminal on the molecular chain. There are no particular limitations on the type of the addition reaction, but an addition reaction in the presence of a hydrosilylation reaction catalyst is preferred from the standpoint of the yield, purity, and control of the reaction.

In specific terms, the thickener or gellant comprising the hereinabove-described organopolysiloxane according to the present application can be produced by addition reacting at least
(A') an organohydrogenpolysiloxane that contains silicon-bonded hydrogen and that has a degree of polymerization of more than 200 and
(K) a polyglycerol structure-containing hydrophilic compound that has one alkenyl group wherein the alkenyl group resides in terminal position on the molecular chain and that contains at least one type of hydrophilic unit selected from the hydrophilic units given by the previously described structural formulas (3-1) to (3-3)
in the presence of
(M) a hydrosilylation reaction catalyst.

Viewed from the perspective of the thickening effect and gelation performance for oil components exercised by the organopolysiloxane according to the present application, the organopolysiloxane according to the present application can be obtained in particular by reacting (A') an organohydrogensiloxane that contains silicon-bonded hydrogen and has a degree of polymerization of more than 200, in a system in which there are present at least both a chain organopolysiloxane that is given by general formula (2') below, that has one carbon-carbon double bond, which resides in terminal position on the molecular chain, and that preferably has the chain organosiloxane group given by the previously indicated structural formula (2-1), wherein this chain organopolysiloxane is used in a quantity that provides not more than 0.9 molar equivalents with respect to the silicon-bonded hydrogen in component (A'), and (K1) a polyglycerol structure-containing hydrophilic compound that has one alkenyl group wherein the alkenyl group resides in terminal position on the molecular chain and that contains within the molecule at least one type of hydrophilic unit selected from the hydrophilic units given by structural formulas (3-1-1) to (3-3-1)

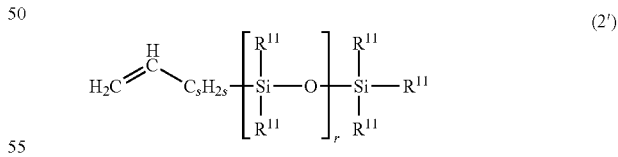

(2')

wherein $R^{11}$ is the same as described above, s is a number in the range from 0 to 8, and r is a number in the range from 1 to 100.

The thickener or gellant according to the present application can be particularly preferably obtained by addition reacting, in the presence of (M) a hydrosilylation reaction catalyst, the previously indicated component (A') organohydrogensiloxane in a system in which there are present at least both a chain organopolysiloxane that is given by general formula (2') above and that has one carbon-carbon double bond, which resides in terminal position on the molecular chain, wherein this chain organopolysiloxane is used in a quantity that provides not more than 0.9 molar equivalents with respect to the silicon-bonded hydrogen in component (A'), and (K2) a hydrophilic compound that has a tetraglycerol structure in the molecule and that has one alkenyl group wherein the alkenyl group resides in terminal position on the molecular chain.

The aforementioned chain organopolysiloxane having general formula (2') and having one carbon-carbon double bond, which resides in terminal position on the molecular chain, is used in a quantity that provides not more than 0.9 molar equivalents with reference to the silicon-bonded hydrogen in component (A'), and, viewed from the standpoint of the balance between the affinity and gelation characteristics with respect to oil materials, is used in a quantity that provides preferably 0.2 to 0.8 molar equivalents and particularly preferably 0.3 to 0.7 molar equivalents with reference to the silicon-bonded hydrogen in component (A'). On the other hand, when the quantity of use exceeds 0.9 molar equivalents, the obtained organopolysiloxane will have an overly high hydrophobicity and the performance as a thickener or gellant may be unsatisfactory.

The (K1) hydrophilic compound having a polyglycerol structure within the molecule and having one alkenyl group, which resides in molecular chain terminal position, is a hydrophilic compound that has a reactive functional group, e.g., an alkenyl group, at a molecular chain terminal, for example, an allylpolyglycerol, allyl polyglycidyl ether, and monoallyl ether of a polyether.polyglycerol copolymer, and can be synthesized by known methods. Viewed from the standpoint of the thickening effect and gelation performance exercised by the organopolysiloxane according to the present invention for oil components, polyglycerol monoallyl ethers and polyglyceryl eugenol are preferred examples and the presence in the hydrophilic moiety of a polyglycerol structure selected from triglycerol, tetraglycerol, and pentaglycerol is preferred. A hydrophilic compound having a tetraglycerol structure in the hydrophilic moiety is particularly preferred from the standpoint of the thickening effect and gelation performance.

Component (K1) is preferably used in a quantity that provides at least 0.1 molar equivalents with reference to the silicon-bonded hydrogen in component (A'), and, from the standpoint of the gelation properties for oil materials, is used in a quantity that provides preferably 0.2 to 0.8 molar equivalents and particularly preferably 0.3 to 0.7 molar equivalents with reference to the silicon-bonded hydrogen in component (A').

The component (A') organohydrogenpolysiloxane bearing silicon-bonded hydrogen and having a degree of polymerization of more than 200 is specifically an organohydrogensiloxane with the following structural formula (1') wherein n1, n2, n3, and q are the previously defined numbers.

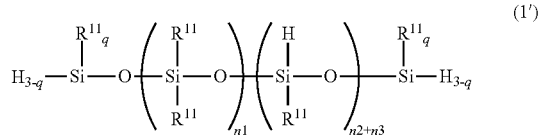

The component (A') organohydrogenpolysiloxane bearing silicon-bonded hydrogen and having a degree of polymerization of more than 200 is particularly preferably a methylhydrogenpolysiloxane given by the following structural formula.

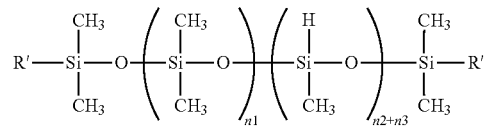

R' in the preceding formula is a group selected from the methyl group and hydrogen atom. n1, n2, and n3 are the previously defined numbers, wherein when (n2+n3)=0, at least one R' is the hydrogen atom.

The hydrosilylation reaction is preferably carried out in the presence of a catalyst, which can be exemplified by compounds of platinum, ruthenium, rhodium, palladium, osmium, iridium, and so forth, wherein platinum compounds are particularly effective because they have a high catalytic activity. The platinum compounds can be exemplified by chloroplatinic acid; platinum metal supported on a support such as alumina, silica, carbon black, and so forth; and platinum complexes such as platinum-vinylsiloxane complexes, platinum-phosphine complexes, platinum-phosphite complexes, and platinum-alcoholate catalysts. In the case of use of a platinum catalyst, the catalyst is used at about 0.5 to 100 ppm as platinum metal.

The crude organopolysiloxane product yielded by the addition reaction described above can be purified by deodorization by a hydrogenation reaction in the presence of a hydrogenation catalyst in a solvent or without using a solvent, and the resulting purified product is preferred for use in topical applications where low odor and compatibility with other cosmetic components are required. In addition, a stripping step, in which the light substances are distilled out at reduced pressure while in contact with nitrogen gas, is preferably carried out on the crude organopolysiloxane product or on the hydrogenate as a step preceding or following the deodorization step.

The solvents, reaction conditions, reduced pressure conditions, and so forth, used for the purification of known organopolysiloxane copolymers or polyether-modified silicones can be used and selected for the hydrogenation reaction and stripping step under consideration without any particular limitation.

The crude organopolysiloxane product obtained by the previously described addition reaction can also be conveniently deodorized by adding an acidic substance and carrying out hydrolysis of the unreacted unsaturated compound and thereafter performing a stripping step in which the light substances are distilled out under reduced pressure while in contact with nitrogen gas.

The organopolysiloxane according to the present invention yielded by the previously described production method can be conveniently produced and also facilitates and supports functionality-related molecular design because the type of modifying group and the degree of modification can be easily adjusted simply by altering the starting material charge. Furthermore, almost no post-production separation into two phases or precipitation of unreacted starting material occurs with the obtained organopolysiloxane, which thus offers the advantages of being chemically stable and having an excellent practicality.

The thickener or gellant comprising the organopolysiloxane according to the present invention, because it is a polymer that has a polyglycerol structure-containing hydrophilic group and a degree of polymerization of more than 200 for the organosiloxane unit constituting its main chain, characteristically has a very high thickening effect or gelation performance for oil materials. In addition, in a particularly preferred embodiment, the thickener or gellant according to the present invention has a chain organopolysiloxane group with structural formula (2-1) or (2-2) in the organopolysiloxane molecule and the hydrophilic group is a tetraglycerol structure-containing hydrophilic group, while the degree of polymerization of the organosiloxane unit constituting the main chain is most preferably more than 300.

These technical effects of "thickening" and "gelling" the (D) oil materials involve continuous phenomena and hence cannot always be clearly differentiated. As a general matter, "thickening" refers to an increase in viscosity by a flowable oil that is a liquid. As thickening proceeds, the oil passes through a viscous fluid state having the form of a thick sticky fluid, cream, or paste, and "gelation" refers to the phenomenon in which the oil subsequently undergoes an almost complete loss of fluidity to present a gel state or a semisolid to a soft solid state. The organopolysiloxane according to the present invention can effectively thicken an oil component when used in small amounts, while through selection of its quantity of use and its structure it can be optimized for use as a thickener or gellant for oil components. In particular, the organopolysiloxane according to the present invention offers the advantage of being able to provide, through suitable selection of its quantity of use, a cosmetic material or topical agent that has a desired viscosity or a desired degree of gelation.

In the field of topical agent and cosmetic product, the thickening or gelling of oil materials can have substantial effects on and induce substantial changes in the appearance, blend type, use sensation, and formulation type of the oil material, and the art of thickening/gelling an oil component is thus extremely important. In addition, the art of thickening/gelling an oil material is also extremely important because it provides the cosmetic manufacturer with the ability to freely adjust and control the state of a cosmetic material from that of a liquid to that of, for example, a thick syrup, cream, paste, gel, or solid.

This oil thickening technical effect requires that the organopolysiloxane according to the present invention be a polymer with an organosiloxane unit degree of polymerization of more than 200, and resides in the ensuing ability to effectively bring about the thickening of an oil at a small quantity of use. Moreover, the degree of thickening or gelation can be controlled through the quantity of use of this organopolysiloxane. Furthermore, among thickeners and gellants for oil materials comprising the organopolysiloxane according to the present application, a thickener or gellant comprising a high molecular weight hydrophilic organopolysiloxane that has a tetraglycerol structure-containing hydrophilic group, that additionally has a siloxane chain and a long-chain hydrocarbyl group in side chain position, and that has a degree of polymerization of more than 300 for its organopolysiloxane chain, has a superior compatibility with a variety of oil materials and thus accrues the advantage of avoiding phase separation problems even when blended in a silicone oil+organic oil mixed oil system.

The oil material (D) is the component that is thickened/gelled by the thickener or gellant comprising the organopolysiloxane according to the present invention. The oil material (D) may be any raw oil material used for topical agents or cosmetic materials and is not otherwise particularly limited. Oils are a particularly suitable as such oil material (D), and a suitable example is (D1) at least one oil selected from solid oils, paste oils, silicone oils, hydrocarbon oils, and ester oils.

The raw oil material thickened/gelled by the thickener or gellant according to the present invention is more preferably (D1-1) at least one oil selected from ester oils, hydrocarbon oils, and silicone oils that are liquids at 5 to 100° C. Thickening or gelation can also be carried out on the combination of this oil with one or two or more selections from the known plant oils and fats, animal oils and fats, higher alcohols, liquid fatty acids, triglycerides, and artificial sebum.

The silicone oils encompassed by component (D) are specifically exemplified by the straight-chain organopolysiloxanes given by the following general formula (1), the cyclic organopolysiloxanes given by general formula (2), and the branched organopolysiloxanes given by general formula (3).

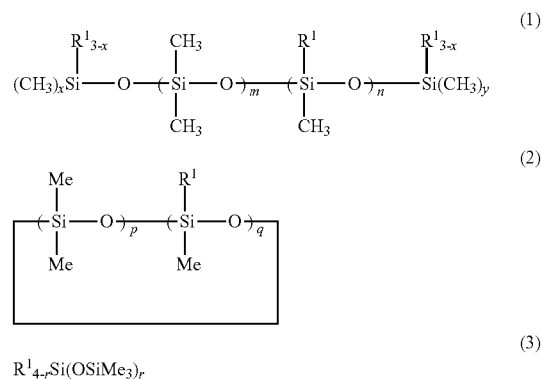

In the preceding formulas (1) to (3) for component (D), $R^1$ is a group selected from the hydrogen atom, the hydroxyl group, $C_{2-30}$ monovalent unsubstituted or fluorine-substituted alkyl groups, aryl groups, amino-substituted alkyl groups, alkoxy groups, and groups represented by $(CH_3)_3SiO\{(CH_3)_2SiO\}_uSi(CH_3)_2CH_2CH_2—$, and can be specifically exemplified by saturated aliphatic hydrocarbyl groups such as ethyl, propyl, butyl, pentyl, hexyl, heptyl, octyl, decyl, and dodecyl; unsaturated aliphatic hydrocarbyl groups such as vinyl, allyl, and hexenyl; saturated alicyclic hydrocarbyl groups such as cyclopentyl and cyclohexyl; aromatic hydrocarbyl groups such as phenyl, tolyl, and naphthyl; and groups provided by substituting a portion of the carbon-bonded hydrogen in the preceding groups with an organic group containing, e.g., a halogen atom, epoxy group, carboxyl group, amino group, methacryl group, mercapto group, and so forth, or provided by substituting a portion of the carbon-bonded hydrogen in the preceding groups with a trimethylsiloxy group bonded across a divalent hydrocarbyl group and/or a chain polydimethylsiloxane bond. m is an integer from 0 to 1000; n is an integer from 0 to 1000; (m+n) is an integer from 1 to 2000; x and y are 0, 1, 2, or 3; p and q are each integers from 0 to 8 wherein $3 \leq p+q \leq 8$; r is an integer from 1 to 4; and u is an integer from 0 to 500.

Silicone oils having the structures described above can be specifically exemplified by cyclic organopolysiloxanes such as hexamethylcyclotrisiloxane (D3), octamethylcyclotetrasiloxane (D4), decamethylcyclopentasiloxane (D5), dodecamethylcyclohexasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl)trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3, 5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, and 1,3,5,7-tetra(N,N-bis(lauroyl)-3-aminopropyl)tetramethylcyclotetrasiloxane, and by straight-chain organopolysiloxanes such as dimethylpolysiloxane endblocked at both molecular chain terminals by trimethylsiloxy, ranging from low viscosity dimethylsilicones at, for example, 2 cSt and 6 cSt, to high viscosity dimethylsilicones at, for example, 1,000,000 cSt, organohydrogenpolysiloxanes, methylphenylpolysiloxanes endblocked at both molecular chain terminals by trimethylsiloxy, dimethylsiloxane-methylphenylsiloxane copolymers endblocked at both molecular chain terminals by trimethylsiloxy, diphenylpolysiloxanes endblocked at both molecular chain terminals by trimethylsiloxy, dimethylsiloxane-diphenylsiloxane copolymers endblocked at both molecular chain terminals by trimethylsiloxy, trimethylpentaphenyltrisiloxane, phenyl(trimethylsiloxy)siloxane, methylalkylpolysiloxanes endblocked at both molecular chain terminals by trimethylsiloxy, dimethylpolysiloxane-methylalkylsiloxane copolymers endblocked at both molecular chain terminals by trimethylsiloxy, dimethylsiloxane-methyl(3,3,3-trifluoropropyl)siloxane copolymers endblocked at both molecular chain terminals by trimethylsiloxy, α,ω-dihydroxypolydimethylsiloxanes, α,ω-diethoxypolydimethylsiloxanes, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyltrisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane; hexamethyl-1,5-diethoxytrisiloxane, hexamethyldisiloxane, octamethyltrisiloxane, alkyl-modified silicones, higher alkoxy-modified silicones, and higher fatty acid-modified silicones.

The hydrocarbon oils encompassed by component (D) can be exemplified by liquid paraffin, light liquid isoparaffin, heavy liquid isoparaffin, vaseline, n-paraffins, isoparaffins, isododecane, isohexadecane, polyisobutylene, hydrogenated polyisobutylene, polybutene, ozokerite, ceresin, microcrystalline wax, paraffin wax, polyethylene wax, polyethylene.polypropylene wax, squalane, squalene, pristane, polyisoprene, and so forth.

The ester oils encompassed by component (D) can be exemplified by hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylolpropane tri-2-ethylhexanoate, ditrimethylol propane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, n-alkyl glycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentyl glycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, esters between dipentaerythritol and fatty acids, 2-hexyldecyl myristate, ethyl laurate, 2-octyldodecyl N-lauroyl-L-glutamate, di(cholesteryl/behenyl/octyldodecyl)N-lauroyl-L-glutamate, di(cholesteryl/octyldodecyl)N-lauroyl-L-glutamate, di(phytosteryl/behenyl/octyldodecyl)N-lauroyl-L-glutamate, di(phytosteryl/octyldodecyl)N-lauroyl-L-glutamate, isopropyl N-lauroylsarcosinate, diisostearyl malate, neopentyl glycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl(hydroxystearate/stearate/rosinate), polyglyceryl tetraisostearate, polyglyceryl-10 nonaisostearate, polyglyceryl-8 deca(erucate/isostearate/ricinoleate), diglyceryl(hexyldecanoate/sebacate) oligoester, glycol distearate (ethylene glycol distearate), diisopropyl dimer dilinoleate, diisostearyl dimer dilinoleate, di(isostearyl/phytosteryl) dimer dilinoleate, (phytosteryl/behenyl)dimer dilinoleate, (phytosteryl/isostearyl/cetyl/stearyl/behenyl)dimer dilinoleate, dimer dilinoleyl dimer dilinoleate, dimer dilinoleyl diisostearate, dimer dilinoleyl hydrogenated rosin condensate, hydrogenated castor oil dimer dilinoleate, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate eicosanedioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl esters of macadamia nut oil fatty acids, phytosteryl esters of macadamia nut oil fatty acids, phytosteryl isostearate, cholesteryl esters of soft lanolin fatty acids, cholesteryl esters of hard lanolin fatty acids, cholesteryl esters of long-chain branched fatty acids, cholesteryl esters of long-chain α-hydroxyfatty acids, octyldodecyl ricinoleate, octyldodecyl esters of lanolin fatty acids, octyldodecyl erucate, hydrogenated castor oil isostearate, ethyl esters of avocado oil fatty acids, and isopropyl esters of lanolin fatty acids.

Oils and fats, higher alcohols, and higher fatty acids are examples of other oil materials.

Plant and animal oils and fats of natural origin and semi-synthetic oils and fats can be exemplified by avocado oil, linseed oil, almond oil, *Ericerus pela* (Chavannes) wax, perilla oil, olive oil, cacao butter, Kapok tree wax, kaya oil, carnauba wax, cod liver oil, candelilla wax, beef tallow, hoof oil, cow bone fat, hardened beef tallow, apricot kernel oil, spermaceti wax, hardened oils, wheat germ oil, sesame oil, rice germ oil, rice bran oil, sugarcane wax, camellia Kissi seed oil, safflower oil, shea butter, Paulownia oil, cinnamon oil, jojoba wax, olive squalane, shellac wax, turtle oil, soybean oil, tea seed oil, camellia oil, evening primrose oil, corn oil, lard, rape-seed oil, Japanese tung oil, bran wax, germ oil, horse fat, persic oil, palm oil, palm kernel oil, castor oil, hardened castor oil, methyl esters of castor oil fatty acids, sunflower oil, grape seed oil, bayberry wax, jojoba oil, hydrogenated jojoba esters, macadamia nut oil, yellow beeswax, mink oil, cottonseed oil, cotton wax, Japan wax, sumac kernel oil, montan wax, coconut oil, hardened coconut oil, cocofatty acid triglycerides, mutton tallow, peanut oil, lanolin, liquid lanolin, reduced lanolin, lanolin alcohol, hardened lanolin, lanolin acetate, isopropyl esters of lanolin fatty acids, POE lanolin alcohol ethers, POE lanolin alcohol acetate, polyethylene glycol esters of lanolin fatty acids, POE hydrogenated lanolin alcohol ether, yolk oil, and so forth. Here, POE denotes polyoxyethylene.

The higher alcohols can be exemplified by lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol; cholesterol, sitosterol, phytosterol, lanosterol, POE cholesterol ether, monostearyl glycerol ether (batyl alcohol), monooleyl glyceryl ether (selachyl alcohol), isostearyl glyceryl ether, and so forth.

The higher fatty acids can be exemplified by lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, and so forth.

The inventive thickener or gellant for oil materials, when mixed with oil material as described above using a known means, thickens the oil material or gels the oil material with the formation of a gel composition. Other components may be additionally incorporated into this thickened or gelled raw oil material, and, as will be described below, this can be used as a gel composition that is a composition for cosmetic material production, i.e., a premix, for the production of a water-based composition.

Moreover, through its addition or uniform dispersion in an already prepared topical agent or cosmetic material, the inventive thickener or gellant for oil materials can thicken or gel the oil material present in this topical agent or cosmetic material. In particular, the thickening or gelation of a cosmetic product oil can provide a suitable cosmetic material viscosity or hardness, can improve the appearance, blending properties, and use sensation of the cosmetic material, and can realize a desired state or condition for a formulation or cosmetic product.

The using amount or blending ratio for the thickener or gellant of the present invention is not particularly limited, but is preferably in the range from 1 to 99 mass % with respect of the mass of the total mass including the oil material and particularly preferably is in the range from 5 to 40 mass %. The degree of thickening will vary as a function of the quantity of incorporation in the oil material, which as a consequence makes it possible to control the viscosity of the total mass including the oil material or the hardness of the resulting gel composition—which is the characteristic of a cosmetic material that can also be indicated by the viscoelasticity of the gel or the springy feel of the gel—into a desired range.

The thickener or gellant comprising the organopolysiloxane according to the present invention can be used by itself, but when used in combination with (B) a powder or a colorant, it exercises an oil thickening/gelling effect and in addition can bring about a stable and uniform dispersion of this particulate in the resulting thickened oil or oil-based gel, and in particular for a mixed oil system can provide a powder-in-oil dispersion that is very stable and free of powder aggregation and sedimentation. Furthermore, an excellent cosmetic effect and a discomfort-free natural skin sensation can be maintained for about 1 day after this powder-in-oil dispersion has been applied to the skin, and an excellent dispersion•immobilization performance can thus be manifested.

This component (B) is a powder or a colorant and will mainly be a powder or colorant as used in cosmetic materials. Any of these powders or colorants used in the usual cosmetics can be used regardless of shape, e.g., spherical, rod-shaped, needle-shaped, plate-shaped, irregular, spindle-shaped, and so forth; particle size, e.g., aerosol, microparticulate, pigment grade, and so forth; and particle structure, e.g., porous, non-porous, and so forth. However, when these powders and/or colorants are incorporated as pigments, the incorporation is preferred of one or two or more selections from inorganic pigment powders, organic pigment powders, and resin powders that have an average particle size in the range from 1 nm to 20 μm.

The powder or colorant can be exemplified by inorganic powders, organic powders, metal salt powder surfactants, i.e., metal soaps, colored pigments, pearlescent pigments, organomodified clay minerals, metal powder pigments, and so forth; composites of these pigments may also be used. In specific terms, the inorganic powder can be exemplified by titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, sodium silicate, sodium magnesium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powders, calcium secondary phosphate, alumina, aluminum hydroxide, boron nitride, and so forth; the organic powder can be exemplified by polyamide powder, polyester powder, polyethylene powder, polypropylene powder, polystyrene powder, polyurethane powder, benzoguanamine powder, polymethylbenzoguanamine powder, polytetrafluoroethylene powder, polymethyl methacrylate powder, cellulose, silk powder, nylon powder, nylon 12, nylon 6, silicone powder, spherical silicone rubber powder, spherical silicone rubber powder having a surface coated by a polymethylsilsesquioxane, spherical polymethylsilsesquioxane powder, styrene.acrylic acid copolymer, divinylbenzene.styrene copolymer, vinyl resin, urea resin, phenolic resin, fluororesin, silicon resin, acrylic resin, melamine resin, epoxy resin, polycarbonate resin, microcrystalline fiber powder, starch powder, and lauroyllysine; the metal salt powder surfactant can be exemplified by zinc stearate, aluminum stearate, calcium stearate, magnesium stearate, zinc myristate, magnesium myristate, zinc palmitate, zinc laurate, zinc cetyl phosphate, calcium cetyl phosphate, and sodium zinc cetyl phosphate; the colored pigment can be exemplified by inorganic red pigments such as iron oxide red, iron oxide, iron hydroxide, and iron titanate, inorganic brown pigments such as γ-iron oxide, inorganic yellow pigments such as iron oxide yellow and ocher, inorganic black pigments such as iron oxide black and carbon black, inorganic purple pigments such as Manganese Violet and Cobalt Violet, inorganic green pigments such as chromium hydroxide, chromium oxide, cobalt oxide, and cobalt titanate, inorganic blue pigments such as Prussian blue and ultramarine blue, the lakes of tar dyes such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207, and the lakes of natural dyes such as carminic acid, laccaic acid, carthamin, brazilin, and crocin; the pearlescent pigment can be exemplified by titanium oxide-coated mica, titanium mica, iron oxide-treated titanium mica, bismuth oxychloride, titanium oxide-coated bismuth oxychloride, titanium oxide-coated talc, fish scale foil, and titanium oxide-coated colored mica; and the metal powder pigment can be exemplified by powders of metals such as aluminum, gold, silver, copper, platinum, and stainless steel.

The inorganic powder can also be particularly exemplified by powders that absorb and scatter ultraviolet radiation, e.g., finely divided titanium oxide, finely divided iron-containing titanium oxide, finely divided zinc oxide, finely divided cerium oxide, and composites of the preceding. Considered in greater detail, with regard to an inorganic ultraviolet protective component, for example, the previously described inorganic powder pigment or metal powder pigment may be incorporated as an agent that scatters ultraviolet radiation, and the inorganic ultraviolet protective component can be exemplified by metal oxides such as titanium oxide, zinc oxide, cerium oxide, low-order titanium oxide, and iron-doped titanium oxide; metal hydroxides such as iron hydroxide; metal flake such as iron oxide plates and aluminum flake; and ceramics such as silicon carbide. Particularly preferred thereamong is at least one selection from finely divided metal oxides and finely divided metal hydroxides that have an average particle size in the range from 1 to 100 nm.

The organomodified clay mineral can be exemplified by dimethylbenzyldodecylammonium montmorillonite clay, dimethyldioctadecylammonium montmorillonite clay, dimethylalkylammonium hectorite, benzyldimethylstearylammonium hectorite, and distearyldimethylammonium chloride-treated aluminum magnesium silicate. Commercially available products here are Bentone 27, a benzyldimethylstearylammonium chloride-treated hectorite from the National Lead Co., and Bentone 38, a distearyldimethylammonium chloride-treated hectorite from the National Lead Co.

The spherical silicone rubber powder, also known as spherical silicone elastomer powder, preferably has a primary particle size in the range from 0.1 to 50 μm. Commercially available spherical silicone rubber powders can be exemplified by Torayfil E-506S, Torayfil E-508, 9701 Cosmetic Powder, and 9702 Powder, all from Dow Corning Toray Co., Ltd. A water-based dispersion of the spherical silicone rubber powder may also be used for the cosmetic material of the present invention. Such a water-based dispersion is commercially available as, for example, BY 29-129, PF-2001, and PIF Emulsion, all from Dow Corning Toray Co., Ltd.

In addition, these powders and colorants are particularly preferably subjected to a hydrophobing treatment. Composites may also be formed between these powders and/or colorants; a powder and/or colorant may be used that has been subjected to a surface treatment with, e.g., an ordinary oil, a silicone compound other than the organopolysiloxane according to the present invention, a fluorine compound, or a surfactant; and as necessary a single powder or colorant can be used or two or more powders and/or colorants can be used.

This hydrophobing treatment can be exemplified by treatment of the previously described powder and/or colorant with various hydrophobing surface-treatment agents, for example, treatment with an organosiloxane such as treatment with a methylhydrogenpolysiloxane, treatment with a silicone resin, treatment with a silicone gum, treatment with an acrylsilicone, and treatment with a fluorosilicone; treatment with a metal soap such as treatment with zinc stearate; treatment with a silane such as treatment with a silane coupling agent and treatment with an alkylsilane; treatment with a fluorine compound such as treatment with a perfluoroalkylsilane, a perfluoroalkyl phosphate ester salt, or a perfluoropolyether; treatment with an amino acid such as treatment with N-lauroyl-L-lysine; treatment with an oil such as treatment with squalane; and an acrylic treatment such as treatment with an alkyl acrylate. Combinations of more than one of these may also be used.

The powder or colorant is particularly preferably (B1) at least one powder or colorant selected from the group consisting of silicone resin powders, silicone rubber powders, organic resin powders excluding silicone resin powders, organomodified clay minerals, titanium oxide, zinc oxide, titanium mica, metal soaps, inorganic pigments, and inorganic colored pigments. The thickener or gellant comprising the organopolysiloxane according to the present invention provides an excellent dispersion stability on the part of the powder or colorant, which, in those instances in which an oil+pigment combination is used, makes possible adjustment of the color and covering power of the cosmetic material and facile adjustment of the tactile feel of the cosmetic material without producing the drawbacks of powder aggregation•sedimentation or a worsening of the tactile feel. When, in particular, the oil material is thickened/gelled using the combination with an organic resin powder such as silk powder, nylon powder, polymethyl methacrylate powder, or polyethylene powder or a silicone-type powder such as a silicone rubber powder or silicone resin powder, which exhibit an excellent oil adsorption capacity for oil components, this avoids the powdery feel possessed by these powders and alleviates the strong oily feel of the oil material and thereby accrues the advantage of bringing the post-application skin sensation•skin feel even closer to a natural impression.

The quantity of incorporation for component (B) can be selected in conformity to the state or condition of the formulation or cosmetic material, but is preferably in the range of 0.1 to 99 mass % of the total gel composition comprising the oil material and the organopolysiloxane according to the present invention.

The powder- or colorant-containing gel composition can also be used as such as a gel-form cosmetic material, and the quantity of incorporation in the case of a gel-form cosmetic material is preferably in the range from 10 to 50 mass % of the total cosmetic material. In the case of use as a low-fluidity solid gel-form cosmetic material, the powder or colorant can be incorporated in the range from 50 to 80 weight %.

The thickener or gellant comprising the organopolysiloxane according to the present invention may additionally incorporate (C) at least one selection from the group consisting of silicone-type surfactants excluding those that correspond to component (A), crosslinked organopolysiloxanes, silicone resins, acrylic silicone resins, acrylic silicone dendrimer copolymers, polyamide-modified silicones, alkyl-modified silicone resin waxes, and organic surfactants. This component (C) exhibits an excellent compatibility with the inventive organopolysiloxane+oil material mixture and thus can be stably incorporated in the gel-form composition.

The silicone-type surfactant is a silicone-type surfactant other than the organopolysiloxane according to the present invention. This silicone-type surfactant is a component that emulsifies the oil and/or is a cleansing component, and typical examples are polyoxyalkylene-modified silicones, polyglyceryl-modified silicones, glyceryl-modified silicones, sugar-modified silicones. Examples of preferred silicone-type surfactants are straight-chain polyoxyalkylene-modified organopolysiloxanes, i.e., polyether-modified silicones in which a polyoxyalkylene group is bonded in side chain position and/or terminal position, block copolymer-type polyoxyalkylene.dimethylpolysiloxane copolymers, and straight-chain polyoxyalkylene.alkyl-co-modified organopolysiloxanes, i.e., alkyl/polyether-modified silicones in which a polyoxyalkylene group and an alkyl group are bonded in side chain position and/or terminal position. Other preferred examples in addition to these are the specific elastomer silicone polyethers described in, inter alia, JP 4,080, 597 B (JP 11-049957 A) and JP 2001-011281 A and commercially available as DC 9011 Silicone Elastomer Blend from the Dow Corning Corporation (US).

The silicone resin is preferably, for example, a solid silicone network compound comprising any combination of the trialkylsiloxy unit (M unit), dialkylsiloxy unit (D unit), monoalkylsiloxy unit (T unit), and tetrafunctional siloxy unit (Q unit), i.e., is preferably an MQ resin, MDQ resin, MTQ resin, MDTQ resin, TD resin, TQ resin, or TDQ resin. The substituent on the silicon in these silicone resins is not limited to alkyl and encompasses, for example, substituted alkyl, the phenyl group, and aryl groups. Particularly preferred among the preceding for their excellent usability are fluorine-modified silicone resins, trimethylsiloxysilicic acid (MQ resin), and dimethylsiloxy-containing trimethylsiloxysilicic acid (MDQ resin).

The acrylic silicone resin is preferably an acrylic silicone resin in the form of an acrylic/silicone graft or block copolymer. Also usable are acrylic silicone resins that contain in the molecule at least one moiety selected from the pyrrolidone moiety, long-chain alkyl moieties, polyoxyalkylene moieties, fluoroalkyl moieties, and anionic moieties such as carboxylic acids.

The vinyl polymer having a carbosiloxane dendrimer structure in side chain position and described in JP 4,009,382 B (JP 2000-063225 A) is a particularly preferred specific example of the acrylic silicone dendrimer copolymer. Examples of commercially available products are FA 4001 CM Silicone Acrylate and FA 4002 ID Silicone Acrylate, both from Dow Corning Toray Co., Ltd.

The polyamide-modified silicone can be exemplified by the siloxane-based polyamide described in U.S. Pat. No. 5,981,680. Examples of commercially available products are 2-8178 Gellant and 2-8179 Gellant from the Dow Corning Corporation (US).

A preferred example of the alkyl-modified silicone resin wax is the silsesquioxane resin wax described in JP 2007-532754 A.

The co-used organic surfactant can be one or two or more surfactants selected from the group consisting of anionic surfactants, cationic surfactants, nonionic surfactants, amphoteric surfactants, and semi-polar surfactants. These surfactants may be used as a cleansing component or antiseptic component for the cosmetic material and topical agent and may be used as a dispersing agent or emulsifying agent for, inter alia, the oil. The co-use of a cationic surfactant with the thickener or gellant according to the present invention is useful in particular due to the strong suitability of this combination for application as a hair cosmetic.

More particularly, the anionic surfactant can be exemplified by saturated and unsaturated fatty acid salts, e.g., sodium laurate, sodium stearate, sodium oleate, sodium linolenate, and so forth; alkyl sulfate salts; alkylbenzenesulfonic acids, e.g., hexylbenzenesulfonic acid, octylbenzenesulfonic acid, dodecylbenzenesulfonic acid, and so forth, and their salts; polyoxyalkylene alkyl ether sulfate salts; polyoxyalkylene alkenyl ether sulfate salts; polyoxyethylene alkyl sulfate ester salts; the salts of alkyl sulfosuccinate esters; polyoxyalkylene sulfosuccinate alkyl ester salts; polyoxyalkylene alkylphenyl ether sulfate salts; alkanesulfonate salts; octyltrimethylammonium hydroxide; dodecyltrimethylammonium hydroxide; alkylsulfonate; polyoxyethylene alkylphenyl ether sulfate salts; polyoxyalkylene alkyl ether acetate salts; alkyl phosphate salts; polyoxyalkylene alkyl ether phosphate salts; acylglutamic acid salts; α-acylsulfonic acid salts; alkylsulfonate salts; alkylallylsulfonate salts; α-olefinsulfonate salts; alkylnaphthalenesulfonate salts; alkanesulfonate salts; alkyl or alkenyl sulfate salts; alkylamide sulfate salts; alkyl or alkenyl phosphate salts; alkylamide phosphate salts; alkyloylalkyltaurine salts; N-acylamino acid salts; sulfosuccinate salts; alkyl ether carboxylate salts; amide ether carboxylate salts; α-sulfofatty acid ester salts; alanine derivatives; glycine derivatives; and arginine derivatives. The salts can be exemplified by alkali metal salts, e.g., sodium and so forth; alkaline-earth metal salts, e.g., magnesium and so forth; alkanolamine salts such as the triethanolamine salt and so forth; and ammonium salts.

The cationic surfactant can be exemplified by quaternary ammonium salts such as alkyltrimethylammonium chloride, benzalkonium chloride, and so forth, and by amine salts such as the diethylaminoethylamide of stearic acid and so forth. The preferred structures among these cationic surfactants and the combination of these cationic surfactants with the gellant or thickener according to the present invention are specifically described below.

The nonionic surfactant can be exemplified by polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkylphenols, polyoxyalkylene alkylphenyl ethers, polyoxyalkylene phenylphenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycols, diethylene glycol, fluorosurfactants, polyoxyethylene.polyoxypropylene block polymers, and alkyl polyoxyethylene.polyoxypropylene block polymer ethers.

The amphoteric surfactant can be exemplified by imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specific examples are imidazoline-type amphoteric surfactants such as sodium 2-undecyl-N,N,N-(hydroxyethylcarboxymethyl)-2-imidazoline and 2-cocoyl-2-imidazolinium hydroxide-1-carboxyethyloxy disodium salt; alkylbetaine-type amphoteric surfactants such as lauryldimethylaminoacetic acid betaine and myristyl betaine; amidobetaine-type amphoteric surfactants such as cocofatty acid amidopropyldimethylaminoacetic acid betaine, palm kernel oil fatty acid amidopropyldimethylaminoacetic acid betaine, beef tallow fatty acid amidopropyldimethylaminoacetic acid betaine, hydrogenated beef tallow fatty acid amidopropyldimethylaminoacetic acid betaine, lauric acid amidopropyldimethylaminoacetic acid betaine, myristic acid amidopropyldimethylaminoacetic acid betaine, palmitic acid amidopropyldimethylaminoacetic acid betaine, stearic acid amidopropyldimethylaminoacetic acid betaine, and oleic acid amidopropyldimethylaminoacetic acid betaine; alkylsulfobetaine-type amphoteric surfactants such as cocofatty acid dimethylsulfopropylbetaine; alkylhydroxysulfobetaine-type amphoteric surfactants such as lauryldimethylaminohydroxysulfobetaine; phosphobetaine-type amphoteric surfactants such as laurylhydroxyphosphobetaine; and amidoamino acid-type amphoteric surfactants such as sodium N-lauroyl-N'-hydroxyethyl-N'-carboxymethylethylenediamine, sodium N-oleoyl-N'-hydroxyethyl-N'-carboxymethylethylenediamine, sodium N-cocoyl-N'-hydroxyethyl-N'-carboxymethylethylenediamine, potassium N-lauroyl-N'-hydroxyethyl-N'-carboxymethylethylenediamine, potassium N-oleoyl-N'-hydroxyethyl-N'-carboxymethylethylenediamine, sodium N-lauroyl-N-hydroxyethyl-N'-carboxymethylethylenediamine, sodium N-oleoyl-N-hydroxyethyl-N'-carboxymethylethylenediamine, sodium N-cocoyl-N-hydroxyethyl-N'-carboxymethylethylenediamine, monosodium N-lauroyl-N-hydroxyethyl-N',N'-dicarboxymethylethylenediamine, monosodium N-oleoyl-N-hydroxyethyl-N',N'-dicarboxymethylethylenediamine, monosodium N-cocoyl-N-hydroxyethyl-N',N'-dicarboxymethylethylenediamine, disodium N-lauroyl-N-hydroxyethyl-N',N'-dicarboxymethylethylenediamine, disodium N-oleoyl-N-hydroxyethyl-N',N'-dicarboxymethylethylenediamine, and disodium N-cocoyl-N-hydroxyethyl-N',N'-dicarboxymethylethylenediamine.

The semi-polar surfactant can be exemplified by alkylamine oxide-type surfactants, for example, alkylamine oxides, alkylamidoamine oxides, and alkylhydroxyamine oxides, wherein $C_{10-18}$ alkyldimethylamine oxides and $C_{8-18}$ alkoxyethyldihydroxyethylamine oxides are preferably used. Specific examples are dodecyldimethylamine oxide, dimethyloctylamine oxide, diethyldecylamine oxide, bis(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, cocofatty acid alkyldimethylamine oxide, caprylic acid amidopropyldimethylamine oxide, capric acid amidopropyldimethylamine oxide, lauric acid amidopropyldimethylamine oxide, myristic acid amidopropyldimethylamine oxide, palmitic acid amidopropyldimethylamine oxide, stearic acid amidopropyldimethylamine oxide, isostearic acid amidopropyldimethylamine oxide, oleic acid amidopropyldimethylamine oxide, ricinoleic acid amidopropyldimethylamine oxide, 12-hydroxystearic acid amidopropyldimethylamine oxide, cocofatty acid amidopropyldimethylamine oxide, palm kernel oil fatty acid amidopropyldimethylamine oxide, castor oil fatty acid amidopropyldimethylamine oxide, lauric acid amidoethyldimethylamine oxide, myristic acid amidoethyldimethylamine oxide, cocofatty acid amidoethyldimethylamine oxide, lauric acid amidoethyldiethylamine oxide, myristic acid amidoethyldiethylamine oxide, cocofatty acid amidoethyldiethylamine oxide, lauric acid amidoethyldihydroxyethylamine oxide, myristic acid amidoethyldihydroxyethylamine oxide, and cocofatty acid amidoethyldihydroxyethylamine oxide.

After a topical agent/cosmetic ingredient in the form of a gel composition has been prepared using (A) the thickener or gellant according to the present invention, optionally (B) a powder or a colorant, optionally (C) at least one selection from the group consisting of silicone-type surfactants excluding those that correspond to component (A), crosslinked organopolysiloxanes, silicone resins, acrylic silicone resins, acrylic silicone dendrimer copolymers, polyamide-modified silicones, alkyl-modified silicone resin waxes, and organic surfactants, and (D) a oil material, a lower viscosity cosmetic material with any form, e.g., a paste, cream, emulsified liquid, and so forth, and preferably a cosmetic material emulsion, can be readily prepared by a method in which this gel-form cosmetic material is diluted by admixture thereinto of freely selected quantities of water and (E) at least one compound selected from the group consisting of lower monohydric alcohols and organic polyhydric alcohol compounds.

In addition, (G) an ultraviolet absorber, (H) at least one compound selected from sucrose fatty acid esters and polyglycerol fatty acid esters, (I) an organic film-forming agent, and/or (J) at least one compound selected from the group consisting of amino acids and/or salts thereof, inorganic salts, organic acids and/or salts thereof, and water-soluble polymers, can be incorporated in the above-described gel composition, thereby making possible the stable and facile preparation of a gel-form cosmetic material containing these components.

Similarly, after a topical agent/cosmetic ingredient in the form of a gel composition has been prepared using (A) the thickener or gellant according to the present invention, optionally (B) a powder or a colorant, and (D) an oil material, a lower viscosity cosmetic material with any form, e.g., a paste, cream, emulsified liquid, and so forth, and preferably a cosmetic material emulsion, can be readily prepared by a method in which this gel-form cosmetic material is diluted by admixture thereinto of freely selected quantities of (E) at least one compound selected from the group consisting of lower monohydric alcohols and organic polyhydric alcohol compounds, (F) water, and (L) a physiologically active substance.

The gel composition according to the present invention is a composition for cosmetic material production, i.e., a premix, for the production of a water-containing cosmetic material and accrues the advantage of making possible the formation of a stable water-containing cosmetic material using a convenient stirring device or mixing device without requiring a special high-pressure emulsifying device and also accrues the advantage of rendering investigations for optimizing the emulsification•dispersion conditions almost entirely unnecessary. Furthermore, the cosmetic material produced using the gel composition according to the present invention is a water-containing cosmetic material—and particularly a water-in-oil cosmetic material emulsion—that exhibits an excellent timewise stability, tactile feel, moisture retention, and product appearance and is a water-containing cosmetic material that can stably and easily incorporate the previously indicated components.

The components incorporated in the gel composition according to the present invention are described in detail in the following.

Component (E) is at least one compound selected from the group consisting of lower monohydric alcohols and organic polyhydric alcohol compounds. The gel composition containing this component exhibits additional improvements in its auto-emulsifying characteristics and thus accrues the advantage of rendering almost unnecessary any detailed investigations of the emulsification conditions necessary for the production of a stable water-in-oil cosmetic material emulsion.

The lower alcohols can be exemplified by ethanol, isopropanol, n-propanol, t-butanol, s-butanol, and so forth. The polyhydric alcohols can be exemplified by dihydric alcohols such as 1,3-butylene glycol, 1,2-butylene glycol, propylene glycol, trimethylene glycol, tetramethylene glycol, 2,3-butylene glycol, pentamethylene glycol, 2-buten-1,4-diol, dibutylene glycol, pentyl glycol, hexylene glycol, octylene glycol, and so forth; trihydric alcohols such as glycerol, trimethylolpropane, 1,2,6-hexanetriol, and so forth; tetrahydric and higher hydric polyhydric alcohols such as pentaerythritol, xylitol, and so forth; and sugar alcohols such as sorbitol, mannitol, maltitol, maltotriose, sucrose, erythritol, glucose, fructose, degraded starch, maltose, xylitose, reducing sugar alcohols provided by starch degradation, and so forth. Polyhydric alcohol polymers are another example in addition to the previously cited low molecular weight polyhydric alcohols, and these polyhydric alcohol polymers can be exemplified by diethylene glycol, dipropylene glycol, triethylene glycol, polypropylene glycol, tetraethylene glycol, diglycerol, polyethylene glycol, triglycerol, tetraglycerol, polyglycerol, and so forth.

Ethanol, isopropanol, 1,3-butylene glycol, sorbitol, dipropylene glycol, glycerol, and polyethylene glycol are preferred for component (E) and are able to increase the emulsion stability. Among the preceding, 1,3-butylene glycol, sorbitol, dipropylene glycol, glycerol, and polyethylene glycol are more preferred because they also have a moisturizing effect. The co-use of ethanol and a non-ethanol component (E) as described above mixed at a mass ratio of 5/5 to 9.9/0.1 is also preferred from the perspective of the auto-emulsifying characteristics of the gel composition. Furthermore, a mass ratio between ethanol and a non-ethanol physiologically acceptable hydrophilic medium as described above of at least 6/4 is particularly preferred from the perspective of the auto-emulsifying characteristics of the gel composition.

The water should be clean and free of components toxic to humans and can be exemplified by tap water, purified water, and mineral water. A gel composition that contains a high concentration of a component (E) lower alcohol such as ethanol will be highly flammable; however, the presence of water reduces the flash point and improves the safety during production, storage, and transport. In addition, a water-soluble component, such as a water-soluble ionic surfactant, can be dispersed in the water in advance and then incorporated in the gel composition.

When the cosmetic material according to the present invention is a cosmetic material—and particularly a water-in-oil cosmetic material emulsion—prepared by mixing the previously described gel composition with additional water, the cosmetic material according to the present invention will then contain both this water added during preparation of the cosmetic material and the water present in the gel composition that is a composition for cosmetic material production. These water inputs cannot be distinguished in the cosmetic material.

The gel composition according to the present invention is preferably a gel composition comprising (A) 10 to 70 mass % of the thickener or gellant according to the present invention, (D) 30 to 80 mass % of an oil material, (E) 0 to 20 mass % of at least one compound selected from the group consisting of lower monohydric alcohols and organic polyhydric alcohol compounds, and (F) 0 to 20 mass % water.

The gel composition according to the present invention is more preferably a gel composition comprising (A) 20 to 50 mass % of the thickener or gellant according to the present invention, (D) 40 to 60 mass % of a oil material, (E) 5 to 15 mass % of at least one compound selected from the group consisting of lower monohydric alcohols and organic polyhydric alcohol compounds, and (F) 5 to 15 mass % water.

The optional components for the gel composition according to the present invention are described in detail herebelow. The ultraviolet protective component (G) encompasses inorganic ultraviolet protective components and organic ultraviolet protective components. The (G1) inorganic ultraviolet protective components are agents that disperse ultraviolet radiation and include the metal powder pigments and inorganic powder pigments provided above for component (B). The (G2) organic ultraviolet protective components can be exemplified by salicylic acid types such as homomethyl salicylate, octyl salicylate, triethanolamine salicylate, and so forth; PABA types such as para-aminobenzoic acid, ethyl dihydroxypropyl para-aminobenzoate, glyceryl para-aminobenzoate, octyl dimethyl-para-aminobenzoate, amyl para-dimethylaminobenzoate, 2-ethylhexyl para-dimethylaminobenzoate, and so forth; benzophenone types such as 4-(2-β-glucopyranosyloxy)propoxy-2-hydroxybenzophenone, dihydroxydimethoxybenzophenone, sodium dihydroxydimethoxybenzophenonedisulfonate, 2-hydroxy-4-methoxybenzophenone, hydroxymethoxybenzophenonesulfonic acid and its trihydrate, sodium hydroxymethoxybenzophenonesulfonate, 2-hydroxy-4-methoxybenzophenone-5-sulfuric acid, 2,2'-dihydroxy-4-methoxybenzophenone, 2,4-dihydroxybenzophenone, 2,2',4,4'-tetrahydroxybenzophenone, 2,2'-dihydroxy-4,4'-dimethoxybenzophenone, 2-hydroxy-4-n-octoxybenzophenone, and so forth; cinnamic acid types such as 2-ethylhexyl para-methoxycinnamate also known as octyl para-methoxycinnamate, mono-2-ethylhexanoylglyceryl di-para-methoxycinnamate, methyl 2,5-diisopropylcinnamate, 2,4,6-tris[4-(2-ethylhexyloxycarbonyl)anilino]-1,3,5-triazine, methylbis(trimethylsiloxy)silylisopentyl trimethoxycinnamate, isopropyl para-methoxycinnamate.diisopropylcinnamate ester mixture, the diethylethanolamine salt of p-methoxyhydrocinnamic acid, and so forth; 2-phenylbenzimidazole-5-sulfuric acid; benzoylmethane types such as 4-isopropyldibenzoylmethane, 4-tert-butyl-4'-methoxydibenzoylmethane, and so forth; as well as 2-ethylhexyl 2-cyano-3,3-diphenyl-2-propenoate also known as octocrylene, 2-ethylhexyl dimethoxybenzylidenedioxoimidazolidinepropionate, 1-(3,4-dimethoxyphenyl)-4,4-dimethyl-1,3-pentanedione, cinoxate, methyl o-aminobenzoate, 2-ethylhexyl 2-cyano-3,3-diphenylacrylate, 3-(4-methylbenzylidene)camphor, octyltriazone, 2-ethylhexyl 4-(3,4-dimethoxyphenylmethylene)-2,5-dioxo-1-imidazolidinepropionate, polymer derivatives of the preceding, and silane derivatives of the preceding.

An organic ultraviolet protective component as described above incorporated in a polymer powder can also be used. The polymer powder may or may not be hollow and desirably has an average primary particle diameter in the range from 0.1 to 50 μm, and the particle size distribution may be broad or sharp. The type of polymer can be exemplified by acrylic resins, methacrylic resins, styrene resins, polyurethane resins, polyethylene, polypropylene, polyethylene terephthalate, silicone resins, nylon, and acrylamide resins. A polymer powder incorporating from 0.1 to 30 mass % organic ultraviolet protective component is preferred, while a polymer powder incorporating the UV-A absorber 4-tert-butyl-4'-methoxydibenzoylmethane is particularly preferred. The use of an inorganic ultraviolet protective component in combination with an organic ultraviolet protective component is particularly preferred, and the use of an ultraviolet protective component for UV-A in combination with an ultraviolet protective component for UV-B is even more preferred.

The (H) sucrose fatty acid ester or polyglycerol fatty acid ester is a component that functions as a nonionic surfactant, and the number of carbons in the fatty acid is preferably at least 12 and more preferably is 12 to 20. The (H1) sucrose fatty acid ester can be exemplified by sucrose dioleate, sucrose distearate, sucrose dipalmitate, sucrose dimyristate, sucrose dilaurate, sucrose monooleate, sucrose monostearate, sucrose monopalmitate, sucrose monomyristate, sucrose monolaurate, and so forth. The (H2) polyglycerol fatty acid ester is an ester between a polyglycerol having an average degree of polymerization of 2 to 10 and a fatty acid, for example, a fatty acid selected from caprylic acid, capric acid, lauric acid, myristic acid, palmitic acid, stearic acid, oleic acid, and linoleic acid. Preferred examples of this polyglycerol fatty acid ester are hexaglycerol monooleate, hexaglycerol monostearate, hexaglycerol monopalmitate, hexaglycerol monomyristate, hexaglycerol monolaurate, decaglycerol monooleate, decaglycerol monostearate, decaglycerol monopalmitate, decaglycerol monomyristate, and decaglycerol monolaurate. A single such fatty acid ester can be used or a mixture of these fatty acid esters can be used.

The (I) organic film-forming agent is a component that forms a film on the skin and is a component that functions as a binder in order that the components incorporated in the cosmetic material may be stably maintained in the formulation or on the hair or skin. The thickener or gellant according to the present invention can be suitably used in combination with this organic film-forming agent component and is useful in particular for hair-setting agent compositions. This organic film-forming agent is particularly described below in the section on (P) organic film-forming polymers.

The (J) at least one compound selected from the group consisting of amino acids and/or their salts, inorganic salts, organic acids and/or their salts, and water-soluble polymers is an optional component for the topical agent or cosmetic material and is selected as appropriate in conformity with the function of the cosmetic material.

The amino acid can be exemplified by glycine, valine, leucine, isoleucine, serine, threonine, phenylalanine, arginine, lysine, aspartic acid, glutamic acid, cystine, cysteine, methionine, and tryptophan and/or their salts.

The inorganic salt can be exemplified by the alkali metal salts, alkaline-earth metal salts, aluminum salts, zinc salts, and ammonium salts of hydrochloric acid, sulfuric acid, nitric acid, carbonic acid, phosphoric acid, and so forth. Preferred inorganic salts can be exemplified by chlorides such as sodium chloride, potassium chloride, magnesium chloride, calcium chloride, aluminum chloride, zinc chloride, and ammonium chloride; sulfates such as sodium sulfate, potassium sulfate, magnesium sulfate, aluminum sulfate, zinc sulfate, and ammonium sulfate; nitrates such as sodium nitrate, potassium nitrate, magnesium nitrate, calcium nitrate, aluminum nitrate, zinc nitrate, and ammonium nitrate; carbonates such as sodium carbonate, potassium carbonate, magnesium carbonate, and calcium carbonate; and phosphates such as sodium phosphate and potassium phosphate, whereamong sodium chloride, potassium chloride, magnesium chloride, calcium chloride, sodium sulfate, potassium sulfate, magnesium sulfate, and aluminum sulfate are particularly preferred.

The organic acid is an acid such as acetic acid, lactic acid, citric acid, ascorbic acid, malic acid, tartaric acid, and so forth. The organic acid salt can be exemplified by sodium acetate, potassium acetate, and sodium ascorbate, and also by the salts of α-hydroxyacids such as sodium citrate, sodium lactate, sodium glycolate, sodium malate, and sodium tartrate; by amino acid salts such as sodium aspartate, potassium aspartate, magnesium aspartate, calcium aspartate, sodium glutamate, potassium glutamate, magnesium glutamate, calcium glutamate, the salt between arginine and glutamic acid, the salt between ornithine and glutamic acid, the salt between lysine and glutamic acid, the salt between lysine and aspartic acid, and the salt between ornithine and aspartic acid; and by sodium alginate.

The water-soluble polymer is incorporated for the purpose of improving the use sensation provided by the cosmetic material and may be a water-soluble polymer as used in the usual cosmetic products and may be amphoteric, cationic, anionic, or nonionic, or may be a water-swellable clay mineral. A single water-soluble polymer may be used or two or more may be used in combination. These water-soluble polymers have a thickening effect on water-containing components and therefore are useful in particular for obtaining a gel-form water-containing cosmetic material, a water-in-oil cosmetic material emulsion, and an oil-in-water cosmetic material emulsion.

The amphoteric water-soluble polymer can be exemplified by quaternized starch, by dimethyldiallylammonium chloride derivatives such as, for example, acrylamide.acrylic acid.dimethyldiallylammonium chloride copolymers and acrylic acid.dimethyldiallylammonium chloride copolymers, and by methacrylic acid derivatives such as, for example, polymethacryloylethyldimethylbetaine and N-methacryloyloxyethyl-N,N-dimethylammonium-α-methylcarboxybetaine.alkyl methacrylate copolymers.

The cationic water-soluble polymer can be exemplified by quaternary nitrogen-modified polysaccharides, for example, cation-modified cellulose, cation-modified hydroxyethyl cellulose, cation-modified guar gum, cation-modified locust bean gum, and cation-modified starch; dimethyldiallylammonium chloride derivatives, for example, dimethyldiallylammonium chloride.acrylamide copolymers and polydimethylmethylenepiperidinium chloride; vinylpyrrolidone derivatives, for example, vinylpyrrolidone.dimethylaminoethyl methacrylate copolymer salts, vinylpyrrolidone.methacrylamidopropyltrimethylammonium chloride copolymers, and vinylpyrrolidone.methylvinylimidazolium chloride copolymers; and methacrylic acid derivatives, for example, methacryloylethyldimethylbetaine.methacryloylethyltrimethylammonium chloride.2-hydroxyethyl methacrylate copolymers and methacryloylethyldimethylbetaine.methacryloylethyltrimethylammonium chloride methoxypolyethylene glycol methacrylate copolymers.

The anionic water-soluble polymer can be exemplified by the water-soluble polymers of aliphatic carboxylic acids and their metal salts, e.g., polyacrylic acid and its alkali metal salts, polymethacrylic acid and its alkali metal salts, hyaluronic acid and its alkali metal salts, acetylated hyaluronic acid and its alkali metal salts, and the hydrolyzates of methyl vinyl ether.maleic anhydride copolymers, as well as by carboxymethyl cellulose and its alkali metal salts, methyl vinyl ether-maleate hemiester copolymers, acrylic resin alkanolamine solutions, and carboxyvinyl polymers.

The nonionic water-soluble polymer can be exemplified by polyvinylpyrrolidone, highly polymerized polyethylene glycol, vinylpyrrolidone/vinyl acetate copolymers, vinylpyrrolidone/dimethylaminoethyl methacrylate copolymers, and vinylcaprolactam/vinylpyrrolidone/dimethylaminoethyl methacrylate copolymers and by natural polymer compounds such as cellulose and derivatives thereof, e.g., methyl cellulose, ethyl cellulose, hydroxyethyl cellulose, hydroxypropyl cellulose, carboxymethyl cellulose, and so forth, calcium alginate, pullulan, agar, gelatin, tamarind seed polysaccharides, xanthan gum, carrageenan, high methoxyl pectin, low methoxyl pectin, guar gum, pectin, gum arabic, crystalline cellulose, arabinogalactan, karaya gum, tragacanth gum, alginic acid, albumin, casein, curdlan, gellan gum, dextran, quince seed gum, traganth gum, chitin.chitosan derivatives, starch, e.g., rice, corn, potato, wheat, and so forth, and keratin and collagen and derivatives thereof.

The water-swellable clay mineral is an inorganic water-soluble polymer and is a type of colloid-containing aluminum silicate that has a trilayer structure, and can be generally exemplified by water-swellable clay minerals having the following formula (1)

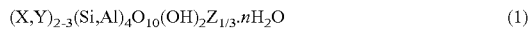

$$(X,Y)_{2-3}(Si,Al)_4O_{10}(OH)_2Z_{1/3} \cdot nH_2O \qquad (1)$$

wherein X is Al, Fe(III), Mn(III), or Cr(III); Y is Mg, Fe(II), Ni, Zn, or Li; and Z is K, Na, or Ca.

This inorganic water-soluble polymer can be specifically exemplified by bentonite, montmorillonite, beidellite, nontronite, saponite, hectorite, aluminum magnesium silicate, and silicic anhydride. These may be either the natural or synthetic material.

The gel composition comprising the components described above can be mixed with water through the application of mechanical force using, for example, a homomixer, paddle mixer, Henschel mixer, Homo Disper, colloid mill, propeller stirrer, homogenizer, inline continuous emulsifier, ultrasound emulsifier, or vacuum kneader.

Neither the quantity of water used nor its blending proportions are limited in the method of the present invention for producing a cosmetic material, but (F) 0.1 to 4000 mass parts water and preferably 5 to 2000 mass parts water can be mixed with 100 mass parts of the gel composition comprising the previously described components. The resulting gel composition can take the form of an oil-in-water emulsion, a water-in-oil emulsion, and so forth, but in particular the gel composition is very useful for its ability to form a stable water-in-oil emulsion state.

Carrying out dilution by intermixing the gel composition of the present invention, (F) water, and (L) a physiologically active substance is a method that readily yields a lower viscosity topical agent or cosmetic material with any form, e.g., a paste, cream, emulsified liquid, and so forth, and preferably a cosmetic material emulsion. In specific terms, a topical agent can be obtained by mixing 100 mass parts of the gel composition containing the previously described components, (F) 0.1 to 4000 mass parts water, and (L) 0.001 to 1.0 mass part of a physiologically active substance.

The physiologically active substance (L) can be exemplified by substances that, when applied to the skin, impart some physiological activity to the skin. Examples in this regard are antiinflammatories, ageing inhibitors, whiteners, pore-tightening agents, antioxidants, hair-restoring agents, hair-growth agents, circulation promoters, antibacterials, antiseptics, desiccants, algefacient agents, calorifacient agents, vitamins, amino acids, wound-healing promoters, anti-irritants, analgesics, cell activators, enzyme components, and so forth. Particularly preferred thereamong for the physiologically active substance is one or more physiologically active substance selected from the group consisting of antiinflammatories, ageing inhibitors, whiteners, hair-restoring agents, hair-growth agents, circulation promoters, antibacterials, antiseptics, vitamins, wound-healing promoters, anti-irritants, analgesics, cell activators, and enzymes.

These components can be exemplified by *Angelica keiskei* extract, avocado extract, *Hydrangea serrata* extract, althea extract, arnica extract, aloe extract, apricot extract, apricot kernel extract, *Gingko biloba* extract, fennel fruit extract, turmeric root extract, oolong tea extract, *Rosa multiflora* extract, *Echinacea angustifolia* leaf extract, *Scutellaria baicalensis* root extract, *Phellodendron amurense* extract, *coptis rhizome* extract, *Hordeum vulgare* seed extract, *Hypericum perforatum* extract, *Lamium album* extract, *Nasturtium officinale* extract, orange extract, dried sea water, seaweed extract, hydrolyzed elastin, hydrolyzed wheat flour, hydrolyzed silk, chamomile extract, carrot extract, *Artemisia capillaris* flower extract, licorice extract, karkade extract, *Pyracantha fortuneana* extract, kiwi extract, cinchona extract, cucumber extract, guanosine, *Gardenia florida* extract, *Sasa veitchii* extract, *Sophora angustifolia* extract, walnut extract, grapefruit extract, *Clematis vitalba* leaf extract, chlorella extract, *Morus alba* root extract, *Gentiana lutea* extract, black tea extract, yeast extract, burdock extract, fermented rice bran extract, rice germ oil, comfrey extract, collagen, *Vaccinum vitis idaea* extract, asiasarum root extract, *Bupleurum falcatum* extract, umbilical extract, Salvia extract, soapwort extract, sasa bamboo grass extract, *Crataegus cuneata* fruit extract, *Zanthoxylum piperitum* extract, shiitake extract, rehmannia root extract, *Lithospermum erythrorhizone* root extract, *Perilla ocymoides* extract, *Tilia cordata* flower extract, *Spiraea ulmaria* extract, *Paeonia albiflora* extract, *Acorus calamus* root extract, *Betula alba* extract, *Equisetum arvense* extract, *Hedera helix* extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, soybean extract, *Zizyphus jujuba* fruit extract, thyme extract, tea extract, *Eugenia caryophyllus* flower extract, *Imperata cylindrica* extract, *Citrus unshiu* Marc extract, angelica root extract, *Calendula officinalis* extract, *Prunus persica* stone extract, *Citrus aurantium* peel extract, *Houttuynia cordata* extract, tomato extract, natto extract, carrot extract, garlic extract, *Rosa canina* fruit extract, hibiscus extract, *Ophiopogon* extract, *Nelumbo nucifera* extract, parsley extract, honey, witch hazel extract, *Parietaria officinalis* extract, *Isodon trichocarpus* extract, bisabolol, *Eriobotrya japonica* extract, coltsfoot flower extract, *Petasites japonicus* extract, *Poria cocos* extract, butcher's broom extract, grape extract, propolis, *Luffa cylindrica* fruit extract, safflower flower extract, peppermint extract, *Tillia miquellana* extract, *Paeonia suffruticosa* root extract, hops extract, *Pinus sylvestris* cone extract, horse chestnut extract, Japanese skunk cabbage extract, *Sapindus mukurossi* peel extract, Melissa extract, peach extract, *Centaurea cyanus* flower extract, Eucalyptus extract, *Saxifraga sarmentosa* extract, *Citrus junos* extract, coix seed extract, *Artemisia princeps* extract, lavender extract, apple extract, lettuce extract, lemon extract, *Astragalus sinicus* extract, rose extract, rosemary extract, Roman chamomile extract, and royal jelly extract.

Other examples are biopolymers such as deoxyribonucleic acid, mucopolysaccharides, sodium hyaluronate, sodium chondroitin sulfate, collagen, elastin, chitin, chitosan, and hydrolyzed eggshell membrane; hormones such as estradiol and ethenylestradiol; oil components such as sphingolipids, ceramides, cholesterol derivatives, and phospholipids; antiinflammatories such as ε-aminocaproic acid, glycyrrhizic acid, β-glycyrrhetinic acid, lysozyme chloride, guaiazulene, hydrocortisone, allantoin, tranexamic acid, and azulene; vitamins such as vitamins A, B2, B6, C, D, and E, calcium pantothenate, biotin, nicotinamide, and vitamin C ester; active components such as allantoin, diisopropylamine dichloroacetate, and 4-aminomethylcyclohexanecarboxylic acid; antioxidants such as carotinoids, flavonoids, tannins, lignans, and saponins; cell activators such as α-hydroxy acids and β-hydroxy acids; circulation promoters such as γ-oryzanol and vitamin E derivatives; wound-healing agents such as retinol and retinol derivatives; algefacients such as cepharanthine, licorice extract, cayenne tincture, hinokitiol, iodized garlic extract, pyridoxine hydrochloride, dl-α-tocopherol, dl-α-tocopherol acetate, nicotinic acid, nicotinic acid derivatives, calcium pantothenate, D-pantothenyl alcohol, acetylpantothenyl ethyl ether, allantoin, isopropylmethylphenol, capronium chloride, benzalkonium chloride, diphenhydramine hydrochloride, Takanal, camphor, nonylic acid vanillylamide, nonanoic acid vanillylamide, piroctone olamine, glyceryl pentadecanoate, l-menthol, and camphor; and hair-growth agents such as mononitroguaiacol, resorcinol, γ-aminobutyric acid, benzethonium chloride, mexiletine hydrochloride, auxin, female hormones, cantharis tincture, cyclosporine, zinc pyrithione, hydrocortisone, minoxidil, polyoxyethylene sorbitan monostearate, peppermint oil, and sasanishiki extract.

The skin beautifying components can be exemplified by whiteners such as placental extract, arbutin, glutathione, Saxifraga sarmentosa extract, and so forth; cell activators such as royal jelly; agents for ameliorating skin roughness; circulation promoters such as nonylic acid valenylamide, benzyl nicotinate, β-butoxyethyl nicotinate, capsaicin, zingerone, Cantharides tincture, ichthammol, caffeine, tannic acid, α-borneol, tocopherol nicotinate, inositol hexanicotinate, cyclandelate, cinnarizine, tolazoline, acetylcholine, verapamil, cepharanthine, γ-oryzanol, and so forth; skin astringents such as zinc oxide, tannic acid, and so forth; and antiseborrheics such as sulfur, thianthrol, and so forth. The vitamins can be exemplified by vitamin A species such as vitamin A oil, retinol, retinol acetate, and retinol palmitate; vitamin B species such as vitamin B2 species such as riboflavin, riboflavin butyrate, and flavin adenine nucleotide, vitamin B6 species such as pyridoxine hydrochloride, pyridoxine dioctanoate, and pyridoxine tripalmitate, vitamin B12 and derivatives thereof, and vitamin B15 and derivatives thereof; vitamin C species such as L-ascorbic acid, L-ascorbic acid dipalmitic acid ester, sodium L-ascorbic acid-2-sulfate, and dipotassium L-ascorbic acid phosphoric acid diester; vitamin D species such as ergocalciferol and cholecalciferol; vitamin E species such as α-tocopherol, β-tocopherol, γ-tocopherol, dl-α-tocopherol acetate, dl-α-tocopherol nicotinate, and dl-α-tocopherol succinate; vitamin H; nicotinic acids such as vitamin P, nicotinic acid, and benzyl nicotinate; and pantothenic acids such as calcium pantothenate, D-pantothenyl alcohol, pantothenyl ethyl ether, and acetylpantothenyl ethyl ether.

The antibacterial preservatives can be exemplified by alkyl para-hydroxybenzoate esters, benzoic acid, sodium benzoate, sorbic acid, potassium sorbate, phenoxyethanol, and so forth, while the antibacterials can be exemplified by benzoic acid, salicylic acid, carbolic acid, sorbic acid, alkyl para-hydroxybenzoate esters, p-chloro-m-cresol, hexachlorophene, benzalkonium chloride, chlorhexidine chloride, trichlorocarbanilide, triclosan, photosensitive ingredients, and so forth. These are preferably not incorporated in lipsticks.

Moreover, a composition that characteristically comprises at least the thickener or gellant of the present invention and in particular (N) a cationic surfactant from among the previously described surfactants is useful as a hair cosmetic or cosmetic material. Cationic surfactants that may be used in combination with the thickener or gellant of the present invention are particularly described in the following.

The (N) cationic surfactants that may be used in combination with the thickener or gellant of the present invention are mainly compounds belonging to the quaternary ammonium salts and amine salts. For example, at least one cationic surfactant selected from the group of compounds given by general formulas (5-1) and (5-2) can be suitably used (5-1)

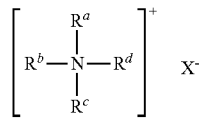

wherein at least one of $R^a$, $R^b$, $R^c$, and $R^d$ represents a straight-chain or branched-chain alkyl group, alkenyl group, alkylbenzyl group, or aliphatic acyloxy(polyethoxy)ethyl group that contains a total of 8 to 35 carbons and that may be substituted by —OH or have interposed therein a functional group given by —O—, —CONH—, —OCO—, or —COO—; the remainder is or are a $C_{1-5}$ alkyl group or hydroxyalkyl group or a polyoxyethylene group that has a total moles of addition of not more than 10; and X— is a halogen ion or an organic anion;

(5-2)

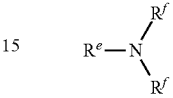

wherein $R^e$ represents a straight-chain or branched-chain alkyl group or alkenyl group that contains a total of 8 to 35 carbons and that may be substituted by —OH or have interposed therein a functional group given by —O—, —CONH—, —OCO—, or —COO—; $R^f$ is a $C_{1-22}$ alkyl group, alkenyl group, or hydroxyalkyl group; and the two groups $R^f$ may be the same as each other or may differ from one another.

Among compounds given by general formula (5-1), compounds in which one of $R^a$, $R^b$, $R^c$, and $R^d$ is a long-chain group are typically organotrimethylammonium salts that contain a halide ion (Cl⁻, Br⁻) or an alkyl sulfate ion ($C_tH_{2t+1}$—$SO_4^-$ where t is a number in the range from 1 to 4), for example, stearyltrimethylammonium chloride, hydroxystearyltrimethylammonium chloride, capryltrimethylammonium chloride, myristyltrimethylammonium chloride, cetyltrimethylammonium chloride, cetyltriethylammonium bromide, behenyltrimethylammonium chloride, lauryltrimethylammonium chloride, and N-stearyl-N,N,N-tri(polyoxyethylene)ammonium chloride (total addition of 3 moles).

Similarly, compounds in which two of $R^a$, $R^b$, $R^c$, and $R^d$ in general formula (5-1) are long-chain groups are typically diorganodimethylammonium salts that contain a halide ion (Cl⁻, Br⁻) or an alkyl sulfate ion ($C_tH_{2t}$—$SO_4^-$ where t is a number in the range from 1 to 4). These two long-chain functional groups may be the same as each other or may differ from one another. These compounds can be exemplified by distearyldimethylammonium chloride, di(hardened beef tallow alkyl)dimethylammonium chloride, di(beef tallow alkyl)dimethylammonium bromide, dioleyldimethylammonium chloride, dipalmitylmethylhydroxyethylammonium methosulfate, distearyldimethylammonium chloride, diisostearyldimethylammonium methosulfate, di[(2-dodecanoylamino)ethyl]dimethylammonium chloride, di[(2-stearoylamino)propyl]dimethylammonium ethosulfate, $C_{8-18}$-alkylbenzyldimethylammonium chloride, benzethonium chloride, dicocoyldimethylammonium chloride, dioctyldimethylammonium chloride, and so forth.

Similarly, compounds in which three of $R^a$, $R^b$, $R^c$, and $R^d$ in general formula (5-1) are long-chain groups are typically triorganomethylammonium salts that contain a halide ion (Cr⁻, Br⁻) or an alkyl sulfate ion ($C_tH_{2t}$—$SO_4^-$ where t is a number in the range from 1 to 4). These three long-chain functional groups may be the same as each other or may differ from one another. These compounds can be exemplified by dioleylmonostearylmethylammonium chloride, dioleylmonobehenylmethylammonium chloride, trioleylmethylammonium chloride, tristearylmethylammonium methosulfate, di(POE)oleylmethylammonium chloride, and so forth.

Besides the preceding, the branched-chain quaternary ammonium salts can be exemplified by those synthesized from a $C_{8-16}$ oxoalcohol starting material. Examples here dialkyldimethylammonium salts and dialkylmethylhydroxyethylammonium salts having alkyl derived from an oxoalcohol. A preferred specific example of this branched-chain quaternary ammonium salt is a dialkyldimethylammonium chloride that contains $C_{8-16}$ alkyl having a branched chain proportion of 10 to 50 mol %. Another type of branched-chain quaternary ammonium salt can be exemplified by alkyltrimethylammonium salts, dialkyldimethylammonium salts, and dialkylmethylhydroxyethylammonium salts that have alkyl derived from $C_{8-28}$ Guerbet alcohols. Particularly preferred thereamong are, for example, 2-decyltetradecyltrimethylammonium chloride, 2-dodecylhexadecyltrimethylammonium chloride, di-2-hexyldecyldimethylammonium chloride, and di-2-octyldodecyldimethylammonium chloride. Other preferred examples are the quaternary ammonium salts described in WO 93/10748, WO 94/06899, and WO 94/16677 and the quaternary ammonium salts described in JP 2000-128740 A and JP 2000-143458 A. Lanolin-derived quaternary ammonium salts are another example.

The compound given by general formula (2) can be exemplified by distearylmethylamine, dioleylmethylamine, dipalmitylmethylamine, stearyldimethylamine, stearyldiethylamine, behenyldimethylamine, behenyldiethylamine, oleyldimethylamine, and palmityldimethylamine. Compounds (5-2) in which $R^e$ is an alkyl or alkenyl group having a total of 8 to 35 carbons and possibly having —CONH— interposed therein are specifically exemplified by stearamidopropyldimethylamine, stearamidepropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures of the preceding, wherein stearamidopropyldimethylamine and stearamidoethyldiethylamine and their mixtures are preferred.

When the tertiary amine or amidoamine is to be used as a salt, an organic acid and/or inorganic acid is added, although this will vary with the pH. Examples are phosphoric acid, hydrochloric acid, acetic acid, succinic acid, and fumaric acid; acidic amino acids such as L-glutamic acid; α-hydroxyacids such as lactic acid, malic acid, and tartaric acid; and mixtures of the preceding, wherein L-glutamic acid, lactic acid, hydrochloric acid, and their mixtures are preferred.

A composition that characteristically comprises at least the thickener or gellant of the present invention and (P) an organic film-forming polymer is also useful as a hair-setting agent composition.

The (P) organic film-forming polymer used here is, like the polymer species described above in the section on the water-soluble polymer, selected from nonionic polymers, cationic polymers, anionic polymers, and amphoteric polymers, as illustrated herebelow. With regard to the selection method, for example, a single selection or two or more selections may be made from the nonionic polymers or two or more selections may be made from polymers in different categories. The organic film-forming polymer (P) has the effect of generating a good hair-setting behavior.

Suitable nonionic polymers can be exemplified by nonionic polymer compounds such as polyvinylpyrrolidone (Luviskol K from BASF), vinylpyrrolidone/vinyl acetate copolymers (Luviskol VA from BASF), vinylpyrrolidone/dimethylaminoethyl methacrylate copolymers (Copolymer 937 from the ISP Corporation), vinylcaprolactam/vinylpyrrolidone/dimethylaminoethyl methacrylate copolymers (Copolymer VC713 from the ISP Corporation), polyvinyl alcohol, and polyoxypropylene butyl ether.

Suitable cationic polymers can be exemplified by cationic polymer compounds such as quaternized vinylpyrrolidone/dimethylaminoethyl methacrylate (GAFQUAT from the ISP Corporation), methylvinylimidazolium chloride/vinylpyrrolidone copolymers (Rubicote from BASF), cationized cellulose, cationized starch, cationized guar gum, the diethyl sulfate salt of vinylpyrrolidone.N,N-dimethylaminoethyl methacrylate copolymers, and diallyl quaternary ammonium salt polymers.

Suitable anionic polymers can be exemplified by anionic polymer compounds such as acrylate ester/methacrylate ester copolymers (Plas Cize from Goo Chemical Co., Ltd.), vinyl acetate/crotonic acid copolymers (Resin 28-1310 from the National Starch Company), vinyl acetate/crotonic acid/vinyl neodecanoate copolymers (Resin 28-2930 from the National Starch Company), methyl vinyl ether/maleate hemiester (Gantrez ES from the ISP Corporation), t-butyl acrylate/ethyl acrylate/methacrylic acid copolymers (Luvimer from BASF); vinylpyrrolidone/vinyl acetate/vinyl propionate copolymers (Luviskol VAP from BASF), vinyl acetate/crotonic acid copolymers (Luviset CA from BASF), vinyl acetate/crotonic acid/vinylpyrrolidone copolymers (Luviset CAP from BASF), vinylpyrrolidone/acrylate copolymers (Luviflex from BASF), acrylate/acrylamide copolymers (Ultrahold from BASF), vinyl acetate/butyl maleate/isobornyl acrylate copolymers (Advantage from the ISP Corporation), alkanolamine acrylic resins, and the urethane-modified acrylic polymers given in WO 2005/054341 and WO 2008/004502.

Suitable amphoteric polymers can be exemplified by amphoteric polymer compounds such as acetic acid-amphoterized dialkylaminoethyl methacrylate copolymers (Yukaformer from Mitsubishi Chemical Corporation), acrylic acid/octylacrylamide/hydroxypropyl acrylate/butylaminoethyl methacrylate copolymers (AMPHOMER from the National Starch Company), and octylacrylamide-butylaminoethyl methacrylate-hydroxypropyl methacrylate-acrylate copolymers.

Various components—such as oil-soluble gellants, pH adjusters, antioxidants, chelating agents, humectants, fragrances, and so forth—other than the previously described components can be used in the topical agent, cosmetic material, hair cosmetic, and hair-setting agent composition of the present invention within a range in which the objects of the present invention are not impaired.

The oil-soluble gellant can be exemplified by a gellant selected from amino acid derivatives such as N-lauroyl-L-glutamic acid and α,γ-di-n-butylamine; dextrin fatty acid esters such as dextrin palmitate, dextrin stearate, and dextrin 2-ethylhexanoate palmitate; sucrose fatty acid esters such as sucrose palmitate and sucrose stearate; fructooligosaccharide fatty acid esters such as inulin stearate and fructooligosaccharide 2-ethylhexanoate; and the benzylidene derivatives of sorbitol such as monobenzylidene sorbitol and dibenzylidene sorbitol.

The pH adjuster can be exemplified by lactic acid, citric acid, glycolic acid, succinic acid, tartaric acid, dl-malic acid, potassium carbonate, sodium bicarbonate, and ammonium bicarbonate. This pH adjuster may be the same as or may differ from the acid/base groups used to prepare the previously described cationic surfactant comprising tertiary amine or amidoamine.

The chelating agent functions to insolubilize the mineral ions in the water and can be exemplified by EDTA, alanine, sodium edetate, sodium polyphosphate, sodium metaphosphate, and phosphoric acid.

The antioxidant can be exemplified by tocopherol, butylhydroxyanisole, dibutylhydroxytoluene, phytic acid, and so forth, and the chelating agent can be exemplified by alanine, sodium edetate, sodium polyphosphate, sodium metaphosphate, and phosphoric acid.

The humectant component can be exemplified by hyaluronic acid, chondroitin sulfate, salts of pyrrolidonecarboxylic acid, polyoxyethylene methyl glucoside, polyoxypropylene methyl glucoside, and so forth.

The fragrance is incorporated in order to impart fragrance or aroma to the cosmetic material or to mask an unpleasant odor. Any fragrance ordinarily incorporated in cosmetic materials can be used without particular limitation, and can be exemplified by fragrances extracted from, inter alia, the flower, seed, leaf, and root of plants; fragrances extracted from seaweed; fragrances extracted from various animal parts and secretions, e.g., musk and incense; and artificially synthesized fragrances, e.g., menthol, musk, acetate esters, and vanilla; and includes the various extracts provided above as examples of the physiologically active substance.

Specific products for the cosmetic material of the present invention can be exemplified by skin cosmetic products such as skin cleansing products, skin care products, make-up products, antiperspirant products, and UV protective products; by hair care cosmetic products such as hair cleansing products, hair styling products, hair dyeing products, hair maintenance products, hair rinse products, hair conditioner products, and hair treatment products; and by bath cosmetic products. Topical agents of the present invention can be exemplified by hair-restoring agents, hair-growth agents, analgesics, antiseptics, antiinflammatories, algefacients, and skin ageing inhibitors, but are not limited to the preceding.

The skin cosmetic products can be used at various locations such as on the scalp, the face including the lips, eyebrows, and cheeks, and on the fingers, nails, and the entire body. The skin cosmetic products can be specifically exemplified by skin cleansing products such as cleansing gels, cleansing creams, cleansing foams, facial cleansing creams, eye make-up removers, facial cleansing foams, liquid whole-body soaps, hand soaps, gel soaps, shaving creams, nail polish removers, anti-acne products, and so forth; skin care products such as skin creams, scalp treatments, skin milks, milky lotions, emulsions, facial compact powders, body powders, essences, shaving lotions, massage products, and so forth; make-up products such as foundations, liquid foundations, oil foundations, make-up bases, white powders, face powders, lip creams, lip colors, lip glosses, eye creams, eyebrow make up, eyelash cosmetic products, and so forth; antiperspirants such as deodorants and so forth; and ultraviolet protective products such as sunscreens, suntanning drugs such as suntanning agents, and so forth.

The hair care cosmetic products can be exemplified by hair cleansing agents such as shampoo, shampoo with rinse, and so forth; hair styling products such as hair waxes, curl retention agents, setting agents, hair creams, hair sprays, hair liquids, and so forth; hair coloring products such as hair color sprays, hair color rinses, hair color sticks, and so forth; hair maintenance products such as hair tonics, hair treatment essences, hair packs, and so forth; and hair rinses and hair conditioning products such as oil rinses, cream rinses, treatment rinses, hair conditioners, hair treatments, and so forth. The previously cited bath cosmetic products can be exemplified by foam bath products.

The form of the cosmetic material and cosmetic product according to the present invention is not particularly limited, and use as a liquid, W/O emulsion, O/W emulsion, W/O cream, O/W cream, solid, paste, gel, powder, multilayer configuration, mousse, mist, granule, flake, or crushed form is preferred. Particularly preferred forms are W/O creams, solids, pastes, gels, and powders, and cosmetic material formulations and cosmetic product formulations that exploit the thickened or gelled characteristics provided by the gellant and thickener of the present invention are useful.

The container for the cosmetic material and cosmetic product according to the present invention is also not particularly limited, and the cosmetic material and cosmetic product according to the present invention may be filled into any container, for example, jars, pumps, tubes, bottles, pressure spray containers, pressure-resistant aerosol containers, lightproof containers, compact containers, metal cans, lipstick containers, dispensing containers, spray bottles, and partitioned containers provided with a mixed fluid discharge outlet. Ordinary silicone-based formulations are prone to undergo separation in tubes, but the cosmetic material and cosmetic product according to the present invention exhibit an excellent stability and thus offer the advantage of making possible stable storage even when filled into tube containers.

EXAMPLES

The description continues below with examples of the present invention, but the present invention is not limited by these examples. In the compositional formulae provided below, Me denotes the methyl group; the Me$_3$SiO or Me$_3$Si group is indicated by "M"; the Me$_2$SiO group is indicated by "D"; the MeHSiO group is indicated by "$D^H$"; and units provided by replacing the methyl in M or D with a substituent are respectively indicated by $M^R$ and $D^R$.

Production Example 1 for Use in the Examples

Synthesis of Hydrophilic Organopolysiloxane No. 1

99.4 g of a methylhydrogenpolysiloxane with the average compositional formula $MD_{400}D^H{}_{10}M$, 43.1 g of a vinyl-monoterminated dimethylpolysiloxane with the structural formula $CH_2=CHSiMe_2(OSiMe_2)_{25}OSiMe_3$, 7.5 g of polyglycerol monoallyl ether, 150 g of isopropyl alcohol (IPA), and 0.20 g of a 2.3 weight % methanolic solution of sodium acetate were introduced into a reactor and were heated to 75° C. while stirring under a nitrogen current. 0.10 g of a 5 weight % IPA solution of chloroplatinic acid was added and a reaction was run for 7 hours at 80° C. 2 g of the reaction solution was then recovered and the completion of the reaction was confirmed through gas production method with alkali decomposition.

This reaction solution was diluted by the addition thereto of 150.0 g of dimethylpolysiloxane (2 cSt, 25° C.) with mixing. This was then heated under reduced pressure to distill out the low-boiling components other than the diluent and obtain a mixture comprising the dimethylpolysiloxane (2 cSt, 25° C.) and a composition containing a linear siloxane/polyglycerol-co-modified silicone with the average compositional formula $MD_{400}D^{R*41}{}_5D^{R*22}{}_5M$; this silicone is referred to below as hydrophilic organopolysiloxane No. 1. The hydrophilic organopolysiloxane:diluent in the obtained mixture=1:1.

In the formula, $R^{*22}$=—$C_3H_6O$—X where X is the tetraglycerol moiety and $R^{*41}$=—$C_2H_4SiMe_2(OSiMe_2)_{25}OSiMe_3$.

Considered as whole, this mixture was a stable milky white gum as a whole, but it was not uniform and partial phase separation had occurred.

Production Example 2 for Use in the Examples

Synthesis of Hydrophilic Organopolysiloxane No. 2

85.3 g of a methylhydrogenpolysiloxane with the average compositional formula $MD_{400}D^H{}_{10}M$, 22.2 g of a vinyl-monoterminated dimethylpolysiloxane with the structural formula $CH_2$=$CHSiMe_2$ $(OSiMe_2)_{25}OSiMe_3$, 6.5 g of polyglycerol monoallyl ether, 115 g of IPA, and 0.16 g of a 2.3 weight % methanolic solution of sodium acetate were introduced into a reactor and were heated to 75° C. while stirring under a nitrogen current. 0.06 g of a 5 weight % IPA solution of chloroplatinic acid was added and a reaction was run for 2 hours at 80° C. 2 g of the reaction solution was then recovered and it was confirmed by gas production method with alkali decomposition that the conversion had reached 85%. 1.0 g 1-decene and 0.06 g of a 5 weight % IPA solution of chloroplatinic acid were added and the reaction was continued for 2 hours at 80° C. When the reaction solution was then sampled again and rechecked, the reaction was found to be completed.

This reaction solution was diluted by the addition thereto of 115.0 g dimethylpolysiloxane (2 cSt, 25° C.) with mixing. This was then heated under reduced pressure to distill out the low-boiling component other than the diluent and obtain a mixture comprising the dimethylpolysiloxane (2 cSt, 25° C.) and a composition containing an alkyl/linear siloxane/polyglycerol-co-modified silicone with the average structural formula $MD_{400}D^{R*11}{}_2D^{R*41}{}_3D^{R*22}{}_5M$; this silicone is referred to below as hydrophilic organopolysiloxane No. 2. The hydrophilic organopolysiloxane:diluent in the obtained mixture=1:1.

In the formula, $R^{*11}$=—$C_{10}H_{21}$ and $R^{*22}$ and $R^{*41}$ are the same as above.

Considered as a whole, this mixture was a stable gray gum, but it was not uniform and partial phase separation had occurred.

Comparative Production Example 1

Comparative Silicone Compound RE1

89.9 g of a methylhydrogenpolysiloxane with the average structural formula $MD_{63}D^H{}_{22}M$, 36.4 g of allylpolyether with the average structural formula $CH_2$=$CH$—$CH_2$—O$(C_2H_4O)_{10}H$, 73.7 g of 1-hexadecene, and 60 g of toluene were introduced into a reactor and were heated to 40° C. while stirring under a nitrogen current. 0.06 g of an IPA solution of a platinum-1,3-divinyl-1,1,3,3-tetramethyldisiloxane complex, wherein the Pt concentration in the IPA solution was 4.5 weight %, was added and a reaction was run for 2.5 hours at 80-110° C. 2 g of the reaction solution was then recovered and the completion of the reaction was confirmed through gas production method with alkali decomposition. The low-boiling components were distilled out by heating the reaction solution under reduced pressure to obtain a composition containing an alkyl/polyether-co-modified silicone with the average structural formula $MD_{63}D^{R*12}{}_{18}D^{R*25}{}_4M$; this silicone is referred to below as silicone compound RE1.

In the formula, $R^{*12}$=—$C_{16}H_{33}$ and $R^{*25}$=—$C_3H_6O(C_2H_4O)_{10}H$.

This composition was a uniform and translucent liquid with a light brown color.

Comparative Production Example 2

Comparative Silicone Compound RE2

206.1 g of a methylhydrogenpolysiloxane with the average structural formula $MD_{400}D^H{}_{10}M$, 105.6 g of allylpolyether with the average structural formula $CH_2$=$CH$—$CH_2$—O$(C_2H_4O)_{19}(C_3H_6O)_{19}H$, 90 g of IPA, 0.12 g of natural vitamin E, and 0.46 g of a 2.0 weight % methanolic sodium acetate solution were introduced into a reactor and were heated to 50° C. while stirring under a nitrogen current. 0.04 g of a 5 weight % IPA solution of chloroplatinic acid was added and a reaction was run for 5 hours at 90° C. Sampling was performed and it was confirmed that the residual Si—H group concentration was within specifications and the reaction was thus completed.

This reaction solution was diluted by the addition thereto of 300.0 g of dimethylpolysiloxane (2 cSt, 25° C.) with mixing. This was then heated under reduced pressure to distill out the low-boiling component other than the diluent and obtain a mixture comprising the dimethylpolysiloxane diluent (2 cSt, 25° C.) and a composition containing a polyether-modified silicone with the average structural formula $MD_{400}D^{R*26}{}_{10}M$; this silicone is referred to below as silicone compound RE2. The silicone composition:diluent ratio here is 1:1.

$R^{*26}$=—$C_3H_{60}(C_2H_4O)_{19}(C_3H_6O)_{19}H$ in the formula.

This mixture was a transparent and almost colorless viscous liquid.

Comparative Production Example 3

Comparative Silicone Compound RE3

212.5 g of a methylhydrogenpolysiloxane with the average structural formula $MD_{406}D^H4M$, 4.9 g of glycerol monoallyl ether with the structural formula $CH_2$=$CH$—$CH_2$—$OCH_2CH(OH)CH_2OH$, and 90 g of IPA were introduced into a reactor and were heated to 70° C. while stirring under a nitrogen current. 0.053 g of an IPA solution of a platinum-1,3-divinyl-1,1,3,3-tetramethyldisiloxane complex, wherein the Pt concentration in the IPA solution was 4.5 weight %, was added and a reaction was run for 3 hours at 80° C. 2 g of the reaction solution was then recovered and the completion of the reaction was confirmed through gas production method with alkali decomposition. The low-boiling components were distilled out by heating the reaction solution under reduced pressure to obtain a composition containing a glycerol-modified silicone with the average structural formula $MD_{406}D^{R*21}{}_4M$; this silicone is referred to below as silicone compound RE3.

In the formula, $R^{*21}$=—$C_3H_6OCH_2CH(OH)CH_2OH$.

This composition was a viscous, translucent, and uniform liquid with a light yellowish brown color.

Comparative Production Example 4

Comparative Silicone Compound RE4

155.9 g of a methylhydrogenpolysiloxane with the average structural formula $MD_{72}D^H{}_{12}M$, 13.0 g of glycerol monoallyl ether with the structural formula $CH_2=CH-CH_2-OCH_2CH(OH)CH_2OH$, 41.1 g of 1-decene, and 63 g of IPA were introduced into a reactor and were heated to 45° C. while stirring under a nitrogen current. 0.055 g of an IPA solution of a platinum-1,3-divinyl-1,1,3,3-tetramethyldisiloxane complex, wherein the Pt concentration in the IPA solution was 4.5 weight %, was added and a reaction was run for 1 hour at 80° C. 2 g of the reaction solution was then recovered and the completion of the reaction was confirmed through gas production method with alkali decomposition. The low-boiling components were distilled out by heating the reaction solution under reduced pressure to obtain a composition containing an alkyl/glycerol-co-modified silicone with the average structural formula $MD_{72}D^{R*11}{}_9D^{R*21}{}_3M$; this silicone is referred to below as silicone compound RE4.

In the formula, $R^{*11}=-C_{10}H_{21}$ and $R^{*21}=-C_3H_6OCH_2CH(OH)CH_2OH$.

This composition was a translucent liquid with a light brown color.

Comparative Production Example 5

Comparative Silicone Compound RE5

134.6 g of a methylhydrogenpolysiloxane with the average structural formula $MD_{72}D^{H}{}_{12}M$, 36.2 g of 1-decene, 29.9 g of polyglycerol monoallyl ether, 200 g of IPA, and 0.25 g of a 2.3 weight % methanolic solution of sodium acetate were introduced into a reactor and were heated to 55° C. while stirring under a nitrogen current. 0.160 g of a 5 weight % IPA solution of chloroplatinic acid was added and a reaction was run for 7 hours at 80° C. 2 g of the reaction solution was then recovered and the completion of the reaction was confirmed through gas production method with alkali decomposition. The low-boiling components were distilled out by heating the reaction solution under reduced pressure to obtain a composition containing an alkyl/polyglycerol-co-modified silicone with the average structural formula $MD_{72}D^{R*11}{}_9D^{R*22}{}_3M$; this silicone is referred to below as silicone compound RE5.

In the formula, $R^{*11}$ is defined as above and $R^{*22}$ is also defined as above as $-C_3H_6O-X$ where X is a tetraglycerol moiety.

Considered as a whole, this composition was a gray gum, but it was not uniform and some degree of phase separation occurred into a light brown gum phase.

Comparative Production Example 6

Comparative Silicone Compound RE6

111.6 g of a methylhydrogenpolysiloxane with the average structural formula $MD_{61}D^{H}{}_{15}M$ was introduced into a reactor. To this was added dropwise with stirring at room temperature a mixture of 30.9 g of a dimethylpolysiloxane modified by vinyl at one terminal and having the structural formula $CH_2=CHSiMe_2(OSiMe_2)_6OSiMe_3$ and 0.10 g of a toluene solution of a platinum-1,3-divinyl-, 1,3,3-tetramethyldisiloxane complex wherein this toluene solution had a Pt concentration of 0.5 weight %, thereby yielding a branched linear siloxane-type polysiloxane intermediate.

Into a separate reactor were introduced 7.0 g of triglycerol monoallyl ether, 50.4 g of 1-dodecene, 100 g of IPA, and 0.40 g of an IPA solution of a platinum-1,3-divinyl-1,1,3,3-tetramethyldisiloxane complex wherein this IPA solution had a Pt concentration of 0.5 weight %, and the previously synthesized branched linear siloxane-type polysiloxane was then added dropwise under a nitrogen current while stirring under solvent reflux. Heating and stirring were continued for 3 hours after the completion of addition, and 2 g of the reaction solution was then recovered and the completion of the reaction was confirmed by gas production method with alkali decomposition. The lower boilers were distilled out by heating the reaction solution under reduced pressure. Filtration then yielded a composition containing an alkyl/linear siloxane/polyglycerol-co-modified silicone with the average-structural formula $MD_{61}D^{R*13}{}_{12}D^{R*41}{}_2D^{R*27}{}_1M$; this silicone is referred to below as silicone compound RE6.

In the formula, $R^{*13}=-C_{12}H_{25}$,
$R^{*41}=-C_2H_4SiMe_2(OSiMe_2)_6OSiMe_3$, and
$R^{*27}=-C_3H_6O-X$ where X is a triglycerol moiety.

This composition was a uniform, translucent, and almost colorless liquid.

Comparative Production Example 7

Comparative Silicone Compound RE7

187.0 g flakes of an α-olefin having on average at least 30 carbons were introduced into a reactor and melted by heating to 80° C. while stirring under a nitrogen current. 0.8 mg of a ligand solution of a platinum-1,3-divinyl-1,1,3,3-tetramethyldisiloxane complex, wherein this ligand solution had a Pt concentration of 22 weight %, was added and 13.0 g of a methylhydrogenpolysiloxane with the average structural formula $MD^{H}{}_{15}M$ was added dropwise over 30 minutes while stirring. The reaction was continued for 3 hours while controlling the reaction temperature to 120° C. Sampling was performed and it was confirmed that the residual Si—H group concentration was within specifications and the reaction was thus completed. This yielded a composition containing an alkyl-modified silicone wax with the average structural formula $MD^{R*14}{}_{15}M$; this silicone wax is referred to below as silicone compound RE7.

In the formula, $R^{*14}$=long-chain alkyl that is at least $-C_{30}H_{61}$.

Comparative Production Example 8

Comparative Silicone Compound RE8 (Amino Acid Derivative-Modified Silicone)

This synthesis was carried out based on the method described in Production Example 1 of Patent Document 8.

(1) 20.1 g of N-ε-lauroyl-L-lysine was suspended in 205 mL of ethanol. After submitting the reaction solution to ice cooling, dry hydrogen chloride gas was introduced to saturation and stirring was performed for 6 hours. After the ethanol had been distilled out, 250 mL of diisobutyl ether was then added; suction filtration was performed; and 300 mL of purified water was added. To the resulting solution was slowly added with stirring 55 g of morpholine dissolved in 70 mL of purified water, and the precipitated white powder was separated by filtration. The obtained white powder was recrystallized from n-hexane to obtain 20.1 g of the isobutyl ester of N-ε-lauroyl-L-lysine.

(2) 150 g of purified water was added to 45.5 g of sodium azide and a completely homogeneous solution was prepared by stirring while cooling with ice water. To this was added dropwise in small portions a solution prepared by mixing 101.4 g of 10-undecenoyl chloride with 150 mL of acetone; this addition was carried out so as to keep the solution temperature in the range from 10 to 15° C. Stirring at around 12° C. was continued for 1 hour after the completion of addition. The solution was then transferred to a separatory funnel and the aqueous and organic layers were separated. The organic layer was slowly added to 500 mL of toluene held at 60° C., followed by stirring for 3 hours in the temperature range from 50 to 60° C. The toluene was distilled off and distillation in vacuo was thereafter carried out to obtain 73.2 g of 10-undecenoyl isocyanate.

(3) 92.6 g of a methylhydrogenpolysiloxane with the average structural formula $M^H D_{100} M^H$ and 7.4 g of 10-undecenoyl isocyanate were added to 100 g of toluene; heating to 85° C. was performed; this was followed by the addition of 0.33 g of a toluene solution of platinum-1,3-divinyl-1,1,3,3-tetramethyldisiloxane wherein the toluene solution had a Pt concentration of 0.3 weight %; and stirring was carried out for 3 hours. The toluene and excess isocyanate compound were distilled off under reduced pressure and a fresh 1000 g toluene and 10.5 g of the isobutyl ester of N-ε-lauroyl-L-lysine were added and stirring was performed for 6 hours at 90° C. The toluene was distilled off, and the resulting transparent gummy solid was dissolved with heating in 1000 g hexane followed by hot filtration. The hexane was distilled from the filtrate to obtain a solid. This solid was then finely ground and subjected to suction filtration while thoroughly washing with 25° C. hexane, after which drying at reduced pressure yielded 20.3 g of a powder of a lysine derivative-modified silicone with the formula given below, i.e., a silicone modified by the N-ε-lauroyl-L-lysine isobutyl ester derivative.

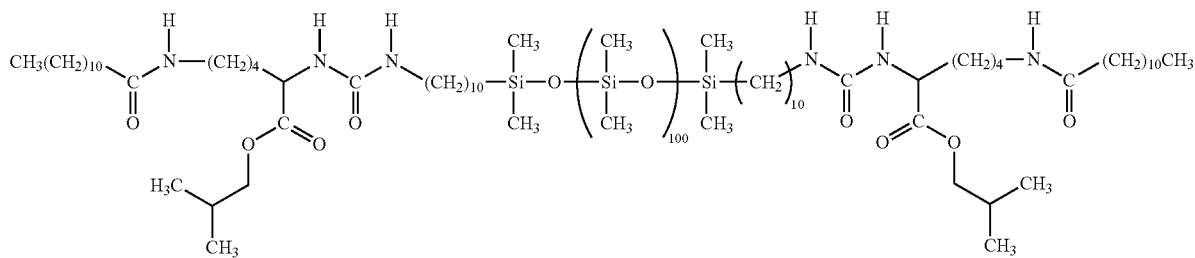

The average compositional formulas are represented as below for the "hydrophilic organopolysiloxane No. 1" and "hydrophilic organopolysiloxane No. 2" according to the present invention and synthesized by the methods described above and for "comparative silicone compound RE1" to "comparative silicone compound RE7" according to the comparative examples and synthesized by the methods described above. The structure of "comparative silicone compound RE8" is described in the preceding paragraph.

TABLE 1

| silicone compound | average compositional formula | state |
|---|---|---|
| composition containing hydrophilic organopolysiloxane No. 1 | $MD_{400}D^{R*41}{}_{5}D^{R*22}{}_{5}M$<br>*diluted to a 50% concentration with dimethylpolysiloxane | milky white gum (not uniform, some degree of phase separation) |
| composition containing hydrophilic organopolysiloxane No. 2 | $MD_{400}D^{R*11}{}_{2}D^{R*41}{}_{3}D^{R*22}{}_{5}M$<br>*diluted to a 50% concentration with dimethylpolysiloxane | gray gum (not uniform, some degree of phase separation) |
| comparative silicone compound RE1 | $MD_{63}D^{R*12}{}_{18}D^{R*25}{}_{4}M$ | uniform and transparent liquid with a light yellow color |
| mixture containing comparative silicone compound RE2 | $MD_{400}D^{R*26}{}_{10}M$<br>*diluted to a 50% concentration with dimethylpolysiloxane | transparent and almost colorless viscous liquid |
| comparative silicone compound RE3 | $MD_{406}D^{R*21}{}_{4}M$ | viscous, translucent, and uniform liquid with a light yellowish brown color |
| comparative silicone compound RE4 | $MD_{72}D^{R*11}{}_{9}D^{R*21}{}_{3}M$ | translucent liquid with a light brown color |
| comparative silicone compound RE5 | $MD_{72}D^{R*11}{}_{9}D^{R*22}{}_{3}M$ | gray gum (not uniform, some degree of phase separation) |
| comparative silicone compound RE6 | $MD_{61}D^{R*13}{}_{12}D^{R*41}{}_{2}D^{R*27}{}_{1}M$ | uniform, translucent, and almost colorless liquid |

TABLE 1-continued

| silicone compound | average compositional formula | state |
|---|---|---|
| comparative silicone compound RE7 | $MD^{R*14}{}_{15}M$ | silicone wax |
| comparative silicone compound RE8 | [structural formula] | |

The classification and structure of the functional groups referenced in the table are as follows.

<Long-Chain Alkyl Group: $R^{*1}$>
$R^{*11}$=—$C_{10}H_{21}$
$R^{*12}$=—$C_{16}H_{33}$
$R^{*13}$=—$C_{12}H_{25}$
$R^{*14}$=long-chain alkyl that is at least —$C_{30}H_{61}$ <Hydrophilic Group: $R^{*2}$>
$R^{*21}$=—$C_3H_6OCH_2CH(OH)CH_2OH$
$R^{*22}$=hydrophilic group represented by —$C_3H_6O$—X where X is a tetraglycerol moiety
$R^{*25}$=—$C_3H_6O(C_2H_4O)_{10}H$
$R^{*26}$=—$C_3H_6O(C_2H_4O)_{19}(C_3H_6O)_{19}H$
$R^{*27}$=hydrophilic group represented by —$C_3H_6O$—X where X is a triglycerol moiety <Group Containing a Linear Polysiloxane Structure: $R^{*4}$>
$R^{*41}$=—$C_2H_4SiMe_2(OSiMe_2)_{25}OSiMe_3$ Examples 1 and 2 and Comparative Examples 1 to 5

Confirmation of Viscosification Effects in Oil Systems

Using the formulations provided in Tables 2 to 8, mixtures between the oils and the modified silicone compounds described above were prepared using the following procedure; these modified silicone compounds included those that were obtained as compositions and also the dilutions prepared depending on the particular production example.

Production and Test Procedure

1. The oil and a modified silicone compound as indicated in the preceding production examples were introduced into a container and mixing and dispersing to uniformity were carried out with heating to 80° C. A combination of comparative silicone compounds RE1 and RE4 in a 1:1 blending ratio was used in Comparative Example 3.

2. The mixture was returned to room temperature and allowed to stand at quiescence for 1 week, after which the appearance and state were recorded.

Evaluation

1. Appearance (compatibility):
   +: a uniform appearance was maintained
   Δ: almost uniform; slight precipitation was seen
   x: nonuniform; separation occurred 2. State (viscosification effect): scored and recorded using the ratings, in sequence starting with the lowest viscosity, of "low viscosity", "viscous", "starch syrup", "gum", and "rubbery". This gum denotes a state like that of a high degree of polymerization silicone gum. When the mixture was converted to a complete solidification (such as conversion to a wax), an x symbol was entered in the table.

Formulations and Evaluation Results

Tables 2 to 8 report the formulations and the results of the viscosification/gelation evaluation.

The "concentration" in the tables indicates the weight % of the modified silicone compound. To economize on space in each table, the following abbreviations are used in the tables to indicate the oils. When a mixed oil prepared by mixing two or more oils at a prescribed ratio was employed, the individual oils are separated by a "/" and the ratio is provided in parentheses. For example, "A/B (70:30)" refers to an oil system in which an oil A and an oil B are blended at 70:30.

2 cSt: dimethylpolysiloxane (2 cSt)
20 cSt: dimethylpolysiloxane (20 cSt)
SH 556: phenyltrimethicone
SS-3408: caprylylmethicone
CEH: cetyl 2-ethylhexanoate
IOTG: glycerol tri-2-ethylhexanoate
IP: isoparaffin
K-230: liquid paraffin Example 1

Viscosification Effects of Hydrophilic Organopolysiloxane No. 1

TABLE 2

| | 10 wt % concentration | | 20 wt % concentration | | 30 wt % concentration | |
|---|---|---|---|---|---|---|
| oil system | compatibility | state | compatibility | state | compatibility | state |
| 2 cSt | + | viscous | + | gum | + | gum |
| 20 cSt | + | starch syrup | + | gum | + | rubbery |

TABLE 2-continued

| oil system | 10 wt % concentration compatibility | state | 20 wt % concentration compatibility | state | 30 wt % concentration compatibility | state |
|---|---|---|---|---|---|---|
| SH 556 | + | viscous | + | gum | + | gum |
| SS-3408 | + | viscous | + | gum | + | gum |
| 2 cSt/CEH (50/50) | + | viscous | + | starch syrup | + | gum |
| 2 cSt/IOTG (50/50) | + | viscous | + | starch syrup | + | gum |
| 2 cSt/IP (50/50) | + | viscous | + | gum | + | gum |
| 2 cSt/K-230 (50/50) | x | — | + | gum | + | rubbery |

Example 2

Viscosification Effects of Hydrophilic Organopolysiloxane No. 2

TABLE 3

| oil system | 10 wt % concentration compatibility | state | 20 wt % concentration compatibility | state | 30 wt % concentration compatibility | state |
|---|---|---|---|---|---|---|
| 2 cSt | + | viscous | + | gum | + | gum |
| 20 cSt | + | starch syrup | + | gum | + | rubbery |
| SH 556 | + | viscous | + | gum | + | gum |
| SS-3408 | + | viscous | + | gum | + | gum |
| 2 cSt/CEH (50/50) | + | viscous | + | starch syrup | + | gum |
| 2 cSt/IOTG (50/50) | + | viscous | + | starch syrup | + | gum |
| 2 cSt/IP (50/50) | + | viscous | + | gum | + | gum |
| 2 cSt/K-230 (50/50) | x | — | + | gum | + | rubbery |

Comparative Example 1

Viscosification Effects of Comparative Silicone Compound RE2

TABLE 4

| oil system | 10 wt % concentration compatibility | state | 20 wt % concentration compatibility | state | 30 wt % concentration compatibility | state |
|---|---|---|---|---|---|---|
| 2 cSt | + | low viscosity | + | viscous | + | viscous |
| 20 cSt | x | — | + | starch syrup | + | starch syrup |
| SH 556 | + | low viscosity | Δ | low viscosity | Δ | low viscosity |
| SS-3408 | + | low viscosity | + | viscous | + | viscous |
| 2 cSt/CEH (50/50) | + | low viscosity | + | low viscosity | + | low viscosity |
| 2 cSt/IOTG (50/50) | Δ | low viscosity | Δ | low viscosity | Δ | low viscosity |
| 2 cSt/IP (50/50) | + | low viscosity | + | viscous | + | viscous |
| 2 cSt/K-230 (50/50) | x | — | + | viscous | + | viscous |

Comparative Example 2

Viscosification Effects of Comparative Silicone Compound RE6

TABLE 5

| oil system | 10 wt % concentration | | 20 wt % concentration | | 30 wt % concentration | |
|---|---|---|---|---|---|---|
| | compatibility | state | compatibility | state | compatibility | state |
| 2 cSt | + | low viscosity | + | low viscosity | + | low viscosity |
| 20 cSt | + | low viscosity | + | low viscosity | + | low viscosity |
| SH 556 | + | low viscosity | + | low viscosity | + | low viscosity |
| SS-3408 | + | low viscosity | + | low viscosity | + | low viscosity |
| 2 cSt/CEH (50/50) | + | low viscosity | + | low viscosity | + | low viscosity |
| 2 cSt/IOTG (50/50) | + | low viscosity | + | low viscosity | + | low viscosity |
| 2 cSt/IP (50/50) | + | low viscosity | + | low viscosity | + | low viscosity |
| 2 cSt/K-230 (50/50) | + | low viscosity | + | low viscosity | + | low viscosity |

Comparative Example 3

Viscosification Effects of Comparative Silicone Compounds RE1/RE4 (Example of Combined Use in a 1:1 Blending Ratio)

TABLE 6

| oil system | 10 wt % concentration | | 20 wt % concentration | | 30 wt % concentration | |
|---|---|---|---|---|---|---|
| | compatibility | state | compatibility | state | compatibility | state |
| 2 cSt | + | low viscosity | + | low viscosity | + | low viscosity |
| 20 cSt | + | low viscosity | + | low viscosity | + | low viscosity |
| SH 556 | + | low viscosity | + | low viscosity | + | low viscosity |
| SS-3408 | + | low viscosity | + | low viscosity | + | low viscosity |
| 2 cSt/CEH (50/50) | + | low viscosity | + | low viscosity | + | low viscosity |
| 2 cSt/IOTG (50/50) | + | low viscosity | + | low viscosity | + | low viscosity |
| 2 cSt/IP (50/50) | + | low viscosity | + | low viscosity | + | low viscosity |
| 2 cSt/K-230 (50/50) | + | low viscosity | + | low viscosity | + | low viscosity |

Comparative Example 4

Viscosification Effects of Comparative Silicone Compound RE7

TABLE 7

| oil system | 10 wt % concentration | | 20 wt % concentration | | 30 wt % concentration | |
|---|---|---|---|---|---|---|
| | compatibility | state | compatibility | state | compatibility | state |
| 2 cSt | x | — | x | — | x | — |
| 20 cSt | x | — | x | — | x | — |
| SH 556 | + | x (solidification) | + | x (solidification) | + | x (solidification) |

TABLE 7-continued

| oil system | 10 wt % concentration | | 20 wt % concentration | | 30 wt % concentration | |
|---|---|---|---|---|---|---|
| | compatibility | state | compatibility | state | compatibility | state |
| SS-3408 | + | x (solidification) | + | x (solidification) | + | x (solidification) |
| 2 cSt/CEH (50/50) | x | — | x | — | x | — |
| 2 cSt/IOTG (50/50) | x | — | x | — | x | — |
| 2 cSt/IP (50/50) | + | x (solidification) | + | x (solidification) | + | x (solidification) |
| 2 cSt/K-230 (50/50) | + | x (solidification) | + | x (solidification) | + | x (solidification) |

Comparative Example 5

Viscosification Effects of Comparative Silicone Compound RE8

TABLE 8

| oil system | 10 wt % concentration | | 20 wt % concentration | | 30 wt % concentration | |
|---|---|---|---|---|---|---|
| | compatibility | state | compatibility | state | compatibility | state |
| 2 cSt | + | x (solidification) | + | x (solidification) | + | x (solidification) |
| 20 cSt | x | — | x | — | x | — |
| SH 556 | Δ | x (solidification) | Δ | x (solidification) | Δ | x (solidification) |
| SS-3408 | + | x (solidification) | + | x (solidification) | + | x (solidification) |
| 2 cSt/CEH (50/50) | + | x (solidification) | Δ | x (solidification) | Δ | x (solidification) |
| 2 cSt/IOTG (50/50) | + | x (solidification) | Δ | x (solidification) | Δ | x (solidification) |
| 2 cSt/IP (50/50) | + | x (solidification) | + | x (solidification) | + | x (solidification) |
| 2 cSt/K-230 (50/50) | Δ | x (solidification) | Δ | x (solidification) | Δ | x (solidification) |

Examples 1 and 2 and Comparative Examples 4 and 5

Recovery from Scratching on the Mixture Surface

Using the 20 weight % concentration mixture with the particular oil, the ability of the surface to recover from scratching was tested for the modified silicone compounds which, according to the results provided in Tables 2 to 8 above, provided a remarkable ability to control the state of a liquid oil.

Test Procedure

1. The surface of the already prepared mixture was scratched with a spatula; the scratch was 1 cm in length and had a depth of 5 mm. The time required for this scratch to spontaneously disappear with the recovery of a smooth surface was observed and recorded.

Evaluation

1. Surface scratch recovery performance
+++: the scratch disappeared immediately and the surface became smooth
++: the scratch disappeared within 1 hour and a smooth surface was recovered
+: the scratch disappeared within 12 hours and a smooth surface was recovered
x: complete disappearance of the scratch did not occur even after at least 24 hours The results of the evaluations for the examples and comparative examples are reported in Table 9.

Examples 1 and 2 and Comparative Examples 4 and 5

Scratch Recovery Performance by an Oil/Modified Silicone Surface

TABLE 9

| | example/comparative example: | | | |
|---|---|---|---|---|
| | Example 1 | Example 2 | Comparative Example 4 | Comparative Example 5 |
| Oil system | Compound | | | |
| | hydrophilic organo-polysiloxane No. 1 | hydrophilic organo-polysiloxane No. 2 | silicone compound RE7 | silicone compound RE8 |
| 2 cSt | ++ | ++ | — (separation) | x |
| 20 cSt | ++ | ++ | — (separation) | — (separation) |
| SH 556 | ++ | ++ | x | x |
| SS-3408 | ++ | ++ | x | x |

TABLE 9-continued

| | example/comparative example: | | | |
|---|---|---|---|---|
| | Example 1 | Example 2 | Comparative Example 4 | Comparative Example 5 |
| | Compound | | | |
| Oil system | hydrophilic organo-polysiloxane No. 1 | hydrophilic organo-polysiloxane No. 2 | silicone compound RE7 | silicone compound RE8 |
| 2 cSt/CEH (50/50) | +++ | +++ | — (separation) | x |
| 2 cSt/IOTG (50/50) | +++ | +++ | — (separation) | x |
| 2 cSt/IP (50/50) | ++ | ++ | x | x |
| 2 cSt/K-230 (50/50) | ++ | ++ | x | x |

Examples 3 and 4 and Comparative Examples 6 to 10

Lipsticks

Lipsticks were produced by subjecting the compositions (formulations) shown in Tables 10 and 11 to heating/mixing•cooling/molding using the procedure described below. The obtained lipsticks were evaluated according to the test procedure described below using the standards described below.

Production Procedure

A. Components 1 to 12 were heated to 50° C. and were mixed and dissolved to uniformity.
B. Component 13 was added to A and mixing and dispersion to uniformity were carried out.
C. The mixture was poured into a mold and cooling and solidification were carried out to yield a lipstick.

Test Procedure 1. 0.05 g of the resulting lipstick was uniformly coated on clean skin (the back of the hand) over a 1 cm×3 cm area.
   Note: Due to the propensity for lipstick to bleed out from the creases when lipstick is applied to the creases of the lip, the back of the hand, which similarly bears numerous creases, was used as the test surface; tactile nerves are also concentrated in the back of the hand and the back of the hand is easily subjected to visual observation.
2. The following five items were evaluated at 10 minutes after application (abbreviated as "initial"), 4 hours after application, 7 hours after application, and 9 hours after application.
   The "resistance to color transfer", "resistance to fading", and "bleed resistance" were visually determined according to below standards.
   The "discomfort-free, natural skin sensation" was determined from the skin feel at the application site according to below standards.
   The "finish" was determined as the overall performance with regard to the visual appearance and cosmetic effect according to below standards.
   Evaluations
1. Resistance to color transfer: the coated surface was lightly pressed against a white ceramic cup and released from the cup and color transfer to the cup was then determined.
   ++: color transfer was entirely absent
   +: very weakly tinted, but not conspicuous
   Δ: slight color transfer
   x: conspicuous color transfer
2. Resistance to fading: changes in the applied color, for example, color fading and/or dullness, were visually evaluated. At 4, 7, and 9 hours, the lipstick was applied, in the same manner as the initial application, to a location on the back of the hand that was separate from but near the coated surface, and the color change was determined by comparison with the freshly applied surface.
   ++: no color change occurred
   +: a slight, but not conspicuous, color change occurred
   Δ: slight color fading was observed
   x: problematically dull color
3. Bleed resistance: the initial 1 cm×3 cm film was visually evaluated for the degree of expansion and widening out into the surroundings with elapsed time.
   ++: no color or oil bleed occurred
   +: a slight, but not conspicuous, color and/or oil bleed occurred
   Δ: slight color and/or oil bleed was observed
   x: problematic color and oil bleed
4. Discomfort-free, natural skin sensation: this was globally determined based on the skin feel in the coated area and the tactile feel when the coated area was touched with a finger.
   ++: the skin feel was natural with no discomfort; the tactile feel was also smooth and free of tackiness
   +: the skin feel included a very slight sense of discomfort, or a very slight tackiness was perceived
   Δ: the skin feel was somewhat unnatural, or the smoothness of the tactile feel was unsatisfactorily low
   x: skin tightness or irritation was perceived, or the tactile feel was not smooth and tackiness was present
5. Finish: the overall performance for the visual appearance and cosmetic effect was rated.
   ++: highly satisfactory
   +: satisfactory
   Δ: acceptable
   x: unsatisfactory Lipstick Formulations and Evaluation Results The lipstick formulations and the results of the evaluations are provided in Tables and 11 below, in which the unit for the numerical values is weight % in all instances. In the tables, FA 4002 ID is a 40 weight % isododecane solution of an (acrylate/methacrylic acid polytrimethylsiloxane) copolymer and DC 593 is a 33 weight % dimethylpolysiloxane (100 cSt) solution of a trimethylsiloxysilicate.

Lipstick Formulations and Evaluation Results (1)

Examples and Comparative Examples

TABLE 10

| No. | component | Example 3 | Example 4 | Comparative Example 6 | Comparative Example 7 |
|---|---|---|---|---|---|
| 1 | polyethylene wax | 15.0 | 15.0 | 15.0 | 15.0 |
| 2 | hydrogenated polyisobutene | 25.0 | 25.0 | 25.0 | 25.0 |
| 3 | FA 4002 ID | 15.0 | 15.0 | 15.0 | 15.0 |
| 4 | DC 593 | 5.0 | 5.0 | 5.0 | 5.0 |
| 5 | isododecane | 20.0 | 20.0 | 20.0 | 20.0 |
| 6 | composition of Production Example 1 | 10.0 | — | — | — |
| 7 | composition of Production Example 2 | — | 10.0 | — | — |

TABLE 10-continued

| No. | component | Example 3 | Example 4 | Comparative Example 6 | Comparative Example 7 |
|---|---|---|---|---|---|
| 8 | composition of Comparative Production Example 4 | — | — | 10.0 | — |
| 9 | composition of Comparative Production Example 5 | — | — | — | 10.0 |
| 13 | colored pigment | 10.0 | 10.0 | 10.0 | 10.0 |
| | total | 100.0 | 100.0 | 100.0 | 100.0 |
| evaluation | resistance to color transfer initial/4 hr/7 hr/9 hr | ++/++/++/++ | ++/++/++/++ | x/x/x/x | +/Δ/Δ/Δ |
| | resistance to fading initial/4 hr/7 hr/9 hr | —/++/++/++ | —/++/++/++ | —/Δ/x/x | —/+/Δ/Δ-x |
| | bleed resistance initial/4 hr/7 hr/9 hr | ++/++/++/++ | ++/++/++/++ | +/+/Δ/Δ | +/+/+/Δ |
| | discomfort-free, natural skin sensation initial/4 hr/7 hr/9 hr | ++/++/++/++ | ++/++/++/++ | x/x/x/x | Δ/Δ/x/x |
| | finish initial/4 hr/7 hr/9 hr | ++/++/++/++ | ++/++/++/++ | x/x/x/x | +-Δ/Δ/Δ/x |

Lipstick Formulations and Evaluation Results (2)

Comparative Examples

TABLE 11

| No. | component | Comparative Example 8 | Comparative Example 9 | Comparative Example 10 |
|---|---|---|---|---|
| 1 | polyethylene wax | 15.0 | 15.0 | 15.0 |
| 2 | hydrogenated polyisobutene | 25.0 | 25.0 | 25.0 |
| 3 | FA 4002 ID | 15.0 | 15.0 | 15.0 |
| 4 | DC 593 | 5.0 | 5.0 | 5.0 |
| 5 | isododecane | 20.0 | 20.0 | 20.0 |
| 10 | composition of Comparative Production Example 6 | 10.0 | — | — |
| 11 | composition of Comparative Production Example 7 | — | 10.0 | — |
| 12 | composition of Comparative Production Example 8 | — | — | 10.0 |
| 13 | colored pigment | 10.0 | 10.0 | 10.0 |
| | total | 100.0 | 100.0 | 100.0 |
| e-valuation | resistance to color transfer initial/4 hr/7 hr/9 hr | Δ/Δ/x/x | Δ/x/x/x | +/+/+/+ |
| | resistance to fading initial/4 hr/7 hr/9 hr | —/+/+/Δ | —/+/+/+ | —/+/+/+ |
| | bleed resistance initial/4 hr/7 hr/9 hr | +/+/Δ/Δ | +/+/Δ/Δ | x/x/x/x |
| | discomfort-free, natural skin sensation initial/4 hr/7 hr/9 hr | Δ/Δ/x/x | Δ/Δ/x/x | Δ/Δ/Δ/Δ |
| | finish initial/4 hr/7 hr/9 hr | +-Δ/Δ/Δ/x | Δ/Δ/x/x | Δ/Δ/Δ/Δ |

Examples 5 and 6 and Comparative Example 11

Gel Compositions

Gel compositions were prepared by mixing the compositions shown in Table 12 according to the following procedure using a Homo Disper mixer. The numerical values in the table indicate the number of parts of addition in mass parts. The obtained gel compositions were evaluated using the following scales and the test procedure described below.

Production Procedure

A. Components 1 to 5 were introduced into a container and heated to 60° C. and were mixed and dissolved to homogeneity.

B. The mixture was returned to room temperature; component 6 was added to A; and mixing and dispersion to homogeneity was carried out.

C. While B was being stirred at 1200 rpm with a Homo Disper mixer, component 7 was added dropwise in small portions; the introduction of water was stopped when the mixture underwent a viscosification⇒ gel conversion.

D. Preparation was completed by continuing the same stirring for 1 minute. The quantity of water addition in weight % up to gelation was recorded.

Note: The quantity of water required for gelation varied as a function of, for example, the structure of the silicone compound used, and as a consequence the results for the total quantity of the gel composition varied somewhat from formulation to formulation.

Test Procedure

1. The state of the obtained composition, that is, whether or not gelation had occurred, was determined based on the appearance and tactile feel.

2. 0.10 g of the gel composition was spread on the back of the hand, and the tactile feel and skin feel were judged after 5 minutes. The quality of the appearance of the coated area was also evaluated.

Evaluation

1. Occurrence of gelation, i.e., the state of the gel
   ++: complete gelation occurred
   +: starch syrupy to soft gel 2. Tactile feel and skin feel
   +: natural skin feel, light to the touch, unpleasant tackiness was completely absent
   x: persistent slimy and uncomfortable sensation or tacky feel 3. Appearance of the coated area
   ++: natural matte appearance
   +: a moderate sheen could be seen
   x: conspicuous oily sheen Gel Composition Formulations and Evaluation Results Examples and Comparative Example

TABLE 12

| No. | component | Example 5 | Example 6 | Comparative Example 11 |
|---|---|---|---|---|
| 1 | D5 | 43.2 | 43.2 | 43.2 |
| 2 | 6 cSt | 3.4 | 3.4 | 3.4 |
| 3 | composition of Production Example 1 | 40.7 | — | — |
| 4 | composition of Production Example 2 | — | 40.7 | — |
| 5 | composition of Comparative Production Example 2 | — | — | 40.7 |
| 6 | ethanol | 12.7 | 12.7 | 12.7 |
| | subtotal | 100.0 | 100.0 | 100.0 |
| 7 | ion-exchanged water | 8.5 | 8.5 | 2.5 |
| | total | 108.5 | 108.5 | 102.5 |
| | occurrence of gelation | ++ | ++ | ++ |

TABLE 12-continued

| No. | component | Example 5 | Example 6 | Comparative Example 11 |
|---|---|---|---|---|
| | tactile feel and skin feel | + | + | x |
| | appearance of the coated area | ++ | + | x |

Examples 7 to 14

Gel Compositions

Gel compositions were prepared by mixing the compositions shown in Tables 13 and 14 according to the following procedure using a Homo Disper mixer. The numerical values in the tables indicate the number of parts of addition in mass parts. The obtained gel compositions were evaluated using the following scales and the test procedure described below.

Production Procedure

A. Components 1 to 4 were introduced into a container and heated to 60° C. and were mixed and dissolved to homogeneity.
B. The mixture was returned to room temperature; component 5 was added to A; and mixing and dispersion to homogeneity was carried out.
C. While B was being stirred at 2500 rpm with a Homo Disper mixer, component 6 was added dropwise in small portions; the introduction of water was halted when the mixture underwent a viscosification⇒ gel conversion.
D. The same stirring was continued for 1 minute.
E. While stirring at 500 rpm, components 7 to 10 were added in small portions to D. Once the entire quantity of components 7 to 10 had been added, stirring and mixing was carried out for 5 minutes at 2500 rpm to bring the entire mass to uniformity.

Test Procedure 1. 0.15 g of the obtained gel composition was spread on the back of the hand, and the tactile feel and use sensation were evaluated during the period of application to immediately after application. The appearance of the coated area, i.e., the impression given by the skin, was also evaluated.
2. The following were evaluated 20 minutes after application: "appearance of the coated area, i.e., impression given by the skin", "moisturizing sensation", "powderiness at the coated area", "wrinkle concealing effect", "cosmetic performance, i.e., overall evaluation".

Evaluations

1. Tactile feel and use sensation:
   ++: excellent smooth tactile feel in depth, very comfortable use sensation
   +: smooth tactile feel in depth, the use sensation is also unproblematic
   Δ: the smoothness and use sensation are both somewhat unsatisfactory
2. Appearance and skin feel for the coated area:
   ++: matte, non-shiny, both the appearance and skin feel provide a natural impression
   +: matte and non-shiny appearance, but the skin experiences a somewhat unnatural sense of discomfort
3. Moisturizing sensation:
   ++: a suitable and agreeable moistness is felt at the skin surface
   +: a moist skin surface can be maintained
   Δ: perception of dryness by the skin
4. Powderiness at the coated area:
   ++: a gritty feel from the powder and a dry feel are entirely absent
   +: a slight gritty feel from the powder is perceived
   x: a gritty feel from the powder and a dry feel are both strongly perceived
5. Wrinkle concealing effect:
   ++: no coating unevenness, good adherence, wrinkles in the skin surface are completely invisible
   +: no coating unevenness, wrinkles in skin surface are almost invisible
   Δ: powder enters into the wrinkle grooves on the skin surface, wrinkles are conspicuous in some places
6. Overall cosmetic performance
   ++: very satisfactory
   +: satisfactory
   Δ: acceptable In the tables, EP-9215 refers to a spherical organopolysiloxane elastomer powder; Bentone 38 refers to a distearyldimethylammonium chloride-treated hectorite; and Aerosil 200 refers to silica, i.e., silicic anhydride.

Gel Composition Formulations and Evaluation Results

Examples

TABLE 13

| No. | component | Example 7 | Example 8 | Example 9 | Example 10 |
|---|---|---|---|---|---|
| 1 | D5 | 43.2 | 43.2 | 43.2 | 43.2 |
| 2 | 6 cSt | 3.4 | 3.4 | 3.4 | 3.4 |
| 3 | composition of Production Example 1 | 40.7 | 40.7 | 40.7 | 40.7 |
| 5 | ethanol | 12.7 | 12.7 | 12.7 | 12.7 |
| | subtotal | 100.0 | 100.0 | 100.0 | 100.0 |
| 6 | ion-exchanged water | 8.5 | 8.5 | 8.5 | 8.5 |
| 7 | EP-9215 | 42.8 | — | — | — |
| 8 | Bentone 38 | — | 42.8 | — | — |
| 9 | Aerosil 200 | — | — | 42.8 | — |
| 10 | nylon powder | — | — | — | 20.0 |
| | total | 151.3 | 151.3 | 151.3 | 128.5 |
| | appearance of the coated area | ++ | ++ | ++ | ++ |
| | tactile feel and use sensation | ++ | + | + | + |
| | moisturizing sensation | ++ | ++ | ++ | ++ |
| | absence of powdery feel | ++ | ++ | + | ++ |
| | wrinkle concealing effect | ++ | + | ++ | ++ |
| | cosmetic performance | ++ | ++−+ | ++−+ | ++ |

Gel Composition Formulations and Evaluation Results (2)

Examples

TABLE 14

| No. | component | Example 11 | Example 12 | Example 13 | Example 14 |
|---|---|---|---|---|---|
| 1 | D5 | 43.2 | 43.2 | 43.2 | 43.2 |
| 2 | 6 cSt | 3.4 | 3.4 | 3.4 | 3.4 |
| 4 | composition of Production Example 2 | 40.7 | 40.7 | 40.7 | 40.7 |

TABLE 14-continued

| No. | component | Example 11 | Example 12 | Example 13 | Example 14 |
|---|---|---|---|---|---|
| 5 | ethanol | 12.7 | 12.7 | 12.7 | 12.7 |
|  | subtotal | 100.0 | 100.0 | 100.0 | 100.0 |
| 6 | ion-exchanged water | 8.5 | 8.5 | 8.5 | 8.5 |
| 7 | EP-9215 | 42.8 | — | — | — |
| 8 | Bentone 38 | — | 42.8 | — | — |
| 9 | Aerosil 200 | — | — | 42.8 | — |
| 10 | nylon powder | — | — | — | 20.0 |
|  | total | 151.3 | 151.3 | 151.3 | 128.5 |
|  | appearance of the coated area | ++ | ++ | ++ | ++ |
|  | tactile feel and use sensation | ++ | + | + | + |
|  | moisturizing sensation | ++ | ++ | ++ | ++ |
|  | absence of powdery feel | ++ | ++ | + | ++ |
|  | wrinkle concealing effect | ++ | + | ++ | ++ |
|  | cosmetic performance | ++ | ++−+ | ++−+ | ++ |

The results reported above demonstrate that the gel compositions of Examples 7 to 14 have excellent properties and an excellent cosmetic performance and also have high value as gel-form cosmetic materials.

Examples 15 to 18

Gel Compositions

Gel compositions were prepared by mixing the compositions shown in Table 15 according to the following procedure using a Homo Disper mixer. The numerical values in the table indicate the number of parts of addition in mass parts.

Production Procedure

A. Components 1 to 7 were introduced into a container and heated to 60° C. and were mixed and dissolved to homogeneity.
B. The mixture was returned to room temperature; component 8 was added to A; and mixing and dispersion to homogeneity was carried out.
C. Components 9 to 12 were introduced into a separate container and were mixed and dissolved by stirring.
D. While B was being stirred at 2500 rpm with a Homo Disper mixer, C was added in small portions, and its introduction was halted when the mixture underwent a viscosification⇒ gel conversion.
E. The same stirring was continued for 2 minutes.
F. While stirring at 500 rpm, component 13 was added in small portions to E. Once the entire quantity had been introduced, stirring and mixing was carried out for 5 minutes at 2500 rpm to bring the entire mass to uniformity.

In the table, D5 refers to decamethylcyclopentasiloxane; SS-3408 refers to caprylylmethicone; and PEG refers to polyethylene glycol.

Gel Composition Formulations

Examples

TABLE 15

| No. | component | Example 15 | Example 16 | Example 17 | Example 18 |
|---|---|---|---|---|---|
| 1 | D5 | 18.0 | 18.0 | 18.0 | 18.0 |
| 2 | SS-3408 | 20.0 | 20.0 | 20.0 | 20.0 |
| 3 | octyl methoxycinnamate | 4.0 | 4.0 | 4.0 | — |
| 4 | sucrose oleate | — | — | — | 2.0 |
| 5 | decaglycerol oleate | — | — | — | 2.0 |
| 6 | composition of Production Example 1 | — | — | — | 48.0 |
| 7 | composition of Production Example 2 | 48.0 | 48.0 | 48.0 | — |
| 8 | ethanol | 10.0 | 10.0 | 10.0 | 10.0 |
|  | subtotal | 100.0 | 100.0 | 100.0 | 100.0 |
| 9 | ion-exchanged water | 9.4 | 9.4 | 8.5 | 8.9 |
| 10 | sodium L-glutamate | 0.1 | — | — | 0.1 |
| 11 | sodium citrate | — | 0.1 | — | — |
| 12 | PEG (Mw 6000) | — | — | 1.0 | — |
| 13 | EP-9215 | 42.8 | 42.8 | 42.8 | 42.8 |
|  | total | 152.3 | 152.3 | 152.3 | 151.8 |

Evaluation Results

The gel compositions obtained in Examples 15 to 18 exhibited a uniform gel state and were also stable—without a change in appearance or state—when stored for 1 month at room temperature. These gel compositions were thus shown to also have a high utility as gel-form cosmetic materials.

Examples 19 to 23

Emulsified Cosmetic Materials

Emulsified cosmetic materials were prepared by mixing the compositions shown in Table 16 according to the following procedure using a Homo Disper mixer.

Preparation Procedure

A. Components 5 to 8 were mixed with each other and dissolved.
B. Components 9 to 11 were mixed with each other and dissolved.
C. Components 1 to 4 were introduced into a container and stirring at room temperature was started at 2500 rpm using a Homo Disper mixer.
D. While stirring C, mixture obtained in step A was added over about 10 seconds and mixing to uniformity was carried out.
E. While further stirring D, mixture obtained in step B was added over 10 minutes.
F. The material adhering to the inner wall of the container was removed with a spatula and the entire composition was again stirred and mixed for 5 minutes to uniformity.

Emulsified Cosmetic Material Formulations

Examples

TABLE 16

| No. | component | Example 19 | Example 20 | Example 21 | Example 22 | Example 23 |
|---|---|---|---|---|---|---|
| 1 | gel composition of Example 15 | 34.95 | — | — | — | — |
| 2 | gel composition of Example 16 | — | 34.95 | — | — | — |
| 3 | gel composition of Example 17 | — | — | 34.95 | — | 34.95 |
| 4 | gel composition of Example 18 | — | — | — | 34.95 | — |
| 5 | ethanol | 2.0 | 2.0 | — | — | — |
| 6 | l-menthol | 0.05 | — | — | — | — |
| 7 | γ-oryzanol | — | 0.10 | — | — | — |
| 8 | fragrance | suitable quantity | suitable quantity | suitable quantity | suitable quantity | suitable quantity |
| 9 | β-arbutin | — | — | 0.05 | 0.05 | — |
| 10 | panthenol | — | — | — | — | 0.10 |
| 11 | ion-exchanged water | 63.0 | 62.95 | 65.0 | 65.0 | 64.95 |
|  | total (excluding the fragrance) | 100.0 | 100.0 | 100.0 | 100.0 | 100.0 |

Evaluation Results

The emulsified cosmetic materials obtained in Examples 19 to 23 ranged in appearance from a uniform cream to a uniform liquid emulsion and also did not undergo changes when stored for 1 month at room temperature and were thus stable.

Formulation Examples

Cosmetic materials and topical agents according to the present invention are described below using formulation examples, but the cosmetic materials and topical gel compositions according to the present invention are certainly not limited to the types or compositions indicated in these formulation examples. In the formulation examples, the cosmetic material ingredients provided with product numbers are in all cases the names of products commercially available from Dow Corning Toray Co., Ltd.

Formulation Example 1

Lipstick

| (component) | (wt %) |
|---|---|
| 1. polyethylene wax (melting point = 88° C.) | 2.0 |
| 2. polyethylene wax (melting point = 107° C.) | 2.0 |
| 3. polyethylene-polypropylene copolymer | 2.0 |
| 4. microcrystalline wax | 2.0 |
| 5. candelilla wax | 3.0 |
| 6. carnauba wax | 3.0 |
| 7. ceresin | 3.0 |
| 8. isotridecyl isononanoate | 9.0 |
| 9. 2-octyldodecanol | 10.0 |
| 10. neopentyl glycol dicaprate | 10.0 |
| 11. diisostearyl malate | 10.0 |
| 12. polyglycerol diisostearate | 10.0 |
| 13. castor oil | 10.0 |
| 14. SH 556 *1) | 2.0 |
| 15. DC 5200 Formulation Aid *2) | 5.0 |
| 16. composition of Production Example 2 | 5.0 |
| 17. Red No. 104 (1) aluminum lake | 1.0 |
| 18. Red No. 201 | 1.0 |
| 19. Red No. 202 | 1.0 |
| 20. Yellow No. 4 aluminum lake | 1.0 |

-continued

| (component) | (wt %) |
|---|---|
| 21. Blue No. 1 aluminum lake | 1.0 |
| 22. titanium mica | 1.0 |
| 23. titanium oxide encapsulated by silica | 2.0 |
| 24. titanium oxide encapsulated by nylon | 2.0 |
| 25. silica containing zirconium oxide | 2.0 |

Note
*1) phenyltrimethicone
Note
*2) alkyl/polyether-co-modified silicone

Production Method

A: Heat and dissolve components 1 to 16; add components 17 to 25; mix to uniformity.

B: Fill into a container to obtain the lipstick.

Formulation Example 2

Lipstick

| (component) | (wt %) |
|---|---|
| 1. polyethylene-polypropylene copolymer | 5.0 |
| 2. candelilla wax | 5.0 |
| 3. carnauba wax | 5.0 |
| 4. vaseline | 10.0 |
| 5. cetyl 2-ethylhexanoate | 10.0 |
| 6. diglycerol diisostearate | 14.5 |
| 7. macadamia nut oil | 7.0 |
| 8. inulin stearate (Rheopearl ISK2 from Chiba Flour Milling Co., Ltd.) | 23.0 |
| 9. composition of Production Example 2 | 2.0 |
| 10. Red No. 201 | 1.0 |
| 11. Red No. 202 | 3.0 |
| 12. Yellow No. 4 aluminum lake | 3.0 |
| 13. titanium oxide | 1.0 |
| 14. iron oxide black | 0.5 |
| 15. iron oxide titanium mica | 10.0 |
| 16. preservative | suitable quantity |
| 17. fragrance | suitable quantity |

Production Method

A: Heat and dissolve components 1 to 9; add components 10 to 16; mix to uniformity.

B: Add component 17 to A and fill into a container to obtain the lipstick.

Formulation Example 3

Lipstick

| (component) | (wt %) |
|---|---|
| 1. ceresin | 6.0 |
| 2. paraffin wax | 6.0 |
| 3. candelilla wax | 4.0 |
| 4. 1-isostearoyl-3-myristoylglycerol | 22.5 |
| 5. 2-ethylhexanoyl triglyceride | 11.0 |
| 6. isopropyl palmitate | 22.5 |
| 7. jojoba oil | 10.0 |
| 8. SH 3775 M *3) | 4.0 |
| 9. isododecane | 3.0 |
| 10. composition of Production Example 2 | 1.0 |
| 11. titanium oxide | 3.0 |
| 12. Red No. 201 | 3.0 |
| 13. Red No. 202 | 2.0 |
| 14. Yellow No. 4 aluminum lake | 2.0 |
| 15. antioxidant | suitable quantity |
| 16. fragrance | suitable quantity |

Note
*3) polyether-modified silicone

Production Method
A: Heat and dissolve components 1 to 10; add components 11 to 15; mix to uniformity.
B: Add component 16 to A and fill into a container to obtain the lipstick.

Formulation Example 4

Lipstick

| (component) | (wt %) |
|---|---|
| 1. microcrystalline wax | 10.0 |
| 2. paraffin wax | 15.0 |
| 3. carnauba wax | 5.0 |
| 4. vaseline | 5.0 |
| 5. diisostearyl malate | 7.0 |
| 6. glyceryl triisostearate | 11.5 |
| 7. propylene glycol dicaprate | 7.0 |
| 8. inulin stearate (Rheopearl ISK2 from Chiba Flour Milling Co., Ltd.) | 2.0 |
| 9. composition of Production Example 2 | 3.0 |
| 10. decamethylcyclopentasiloxane | 10.0 |
| 11. FA 4001 CM *4) | 3.0 |
| 12. DC 593 *5) | 2.0 |
| 13. Red No. 201 | 1.0 |
| 14. Red No. 202 | 1.0 |
| 15. Yellow No. 4 | 2.0 |
| 16. titanium oxide | 4.0 |
| 17. iron oxide black | 0.5 |
| 18. iron oxide titanium mica | 3.0 |
| 19. titanium mica | 2.0 |
| 20. purified water | 5.0 |
| 21. 1,3-butylene glycol | 1.0 |
| 22. preservative | suitable quantity |
| 23. fragrance | suitable quantity |

Note
*4) a decamethylcyclopentasiloxane solution of an (acrylate/methacrylic acid polytrimethylsiloxy) copolymer, containing 30 weight % effective component
Note
*5) a 33 weight % dimethylpolysiloxane (100 cSt) solution of a trimethylsiloxysilicate Production Method
A: Heat and dissolve components 1 to 12; add components 13 to 19; mix to uniformity.
B: Mix components 20 to 22 to uniformity and then add to A and mix.
C: Add component 23 to B and fill into a container to obtain the lipstick.

Formulation Example 5

Oil-Based Solid Eye Shadow

| (component) | (wt %) |
|---|---|
| 1. diisostearyl malate | 6.0 |
| 2. isotridecyl isononanoate | 10.0 |
| 3. liquid paraffin | 10.0 |
| 4. dimethylpolysiloxane (6 cSt) | 8.0 |
| 5. SS-3408 *6) | 10.0 |
| 6. silicic anhydride (Aerosil 200) | 1.2 |
| 7. composition of Production Example 2 | 10.0 |
| 8. ceresin | 6.0 |
| 9. polyethylene wax | 6.0 |
| 10. Blue No. 1 | 0.8 |
| 11. titanium oxide | 1.0 |
| 12. silicone-treated titanium oxide-coated mica | 1.0 |
| 13. titanium oxide•silica•titanium oxide-coated mica | 3.0 |
| 14. silicone-treated mica | 10.0 |
| 15. polymethyl methacrylate | 5.0 |
| 16. silicone-treated sericite | 12.0 |

Note
*6) caprylylmethicone

Production Method
A: Mix components 1 to 5; heat to 90° C.; then add component 6; mix and disperse to uniformity.
B: Add components 7 to 9 to A and dissolve.
C: Add components 10 to 16 to B and mix to uniformity.
D: Fill into a mold and then cool to obtain an oil-based solid eye shadow.

Formulation Example 6

Eye Liner

| (component) | (wt %) |
|---|---|
| 1. decamethylcyclopentasiloxane | 17.0 |
| 2. isoparaffin | 10.0 |
| 3. dimethylpolysiloxane (2 cSt) | 5.0 |
| 4. SH 556 *7) | 5.0 |
| 5. glycerol tri-2-ethylhexanoate | 2.0 |
| 6. composition of Production Example 1 | 3.5 |
| 7. FA 4001 CM *8) | 7.5 |
| 8. DC 593 *9) | 7.5 |
| 9. ethanol | 1.0 |
| 10. dioctadecyldimethylammonium salt-modified montmorillonite | 2.0 |
| 11. silicone-treated iron oxide black | 10.0 |
| 12. 1,3-butylene glycol | 5.0 |
| 13. sodium dehydroacetate | suitable quantity |

-continued

| (component) | (wt %) |
|---|---|
| 14. preservative | suitable quantity |
| 15. purified water | 24.5 |

Note
*7) phenyltrimethicone
Note
*8) a decamethylcyclopentasiloxane solution of an (acrylate/methacrylic acid polytrimethylsiloxy) copolymer, containing 30 weight % effective component
Note
*9) a 33 weight % dimethylpolysiloxane (100 cSt) solution of a trimethylsiloxysilicate Production Method
A: Mix components 1 to 10; add component 11; mix and disperse to uniformity (gel-form cosmetic material)
B: Separately mix components 12 to 15.
C: Slowly add B to A and emulsify to obtain the eye liner.
Alternative Production Method
A: Heat components 1 to 8 to 60° C. and mix and dissolve to uniformity.
B: Return to room temperature; add component 9 to A; mix and disperse to uniformity.
C: While stirring B, add the amount of component 15 corresponding to 1.5 weight % dropwise in small portions and convert the mixture to a gel (gel composition).
D: Add component 10 to C and mix and disperse to uniformity (gel-form cosmetic material).
E: Add component 11 and mix and disperse to uniformity.
F: Separately prepare a liquid mixture of components 12 to 14 and the remainder of component 15 (corresponds to 23.0 weight %).
G: While stirring E, add F in small portions and stir and mix to bring the entire mass to uniformity to obtain the eye liner.

Formulation Example 7

Foundation

| (component) | (wt %) |
|---|---|
| 1. decamethylcyclopentasiloxane | 27.0 |
| 2. SH 556 *10) | 3.0 |
| 3. glycerol tri-2-octanoate | 10.0 |
| 4. composition of Production Example 1 | 4.0 |
| 5. Bentone 27 *11) | 0.5 |
| 6. hydrophobed mixed powder *12) | 18.0 |
| 7. iron oxide red | 1.2 |
| 8. iron oxide yellow | 2.6 |
| 9. ultramarine | 0.1 |
| 10. iron oxide black | 0.1 |
| 11. 1,3-butylene glycol | 7.0 |
| 12. sodium chloride | 0.5 |
| 13. preservative | suitable quantity |
| 14. fragrance | suitable quantity |
| 15. purified water | 26.0 |

Note
*10) phenyltrimethicone
Note
*11) benzyldimethylstearylammonium chloride-treated hectorite (from the National Lead Co.)
Note
*12) Obtained by subjecting a mixed powder with the composition given below to treatment with 1 weight % dimethylmethylhydrogenpolysiloxane with heating.

| a. | finely divided titanium oxide | 8.0 |
| b. | finely divided zinc oxide | 4.0 |
| c. | talc | 3.0 |
| d. | mica | 3.0 |

Production Method
A: Mix components 1 to 6 and uniformly disperse components 7 to 10 (gel-form cosmetic material).
B: Mix components 11 to 13 and 15 and then add to A and emulsify.
C: Add component 14 to C to obtain the foundation.

Formulation Example 8

Foundation

| (component) | (wt %) |
|---|---|
| 1. dimethylpolysiloxane (2 cSt) | 10.0 |
| 2. isododecane | 21.6 |
| 3. isostearyl diglyceryl succinate | 0.6 |
| 4. SS-2910 *13) | 1.2 |
| 5. composition of Production Example 1 | 0.6 |
| 6. BY 25-320 *14) | 1.5 |
| 7. FZ-2250 *15) | 1.5 |
| 8. FA 4002 ID *16) | 2.0 |
| 9. DC 593 *17) | 2.0 |
| 10. coated iron oxide | 3.5 |
| 11. coated titanium dioxide | 6.8 |
| 12. nylon 12 | 8.0 |
| 13. ion-exchanged water | 40.0 |
| 14. magnesium sulfate | 0.7 |
| 15. preservative | suitable quantity |

Note
*13) polyether-modified silicone
Note
*14) 20 weight % isoparaffin solution of a dimethylpolysiloxane gum
Note
*15) 35 weight % isoparaffin solution of a polyether-silicone block copolymer
Note
*16) an isodecane solution of an (acrylate/methacrylic acid polytrimethylsiloxy) copolymer, containing 40 weight % effective component
Note
*17) a 33 weight % dimethylpolysiloxane (100 cSt) solution of a trimethylsiloxysilicate Production Method
A: Mix components 1 to 9 and disperse components 10 to 12 to uniformity.
B: Mix components 13 to 15 and then add to A and emulsify to obtain the foundation.

Formulation Example 9

Gel-Form Cosmetic Material

| (component) | (wt %) |
|---|---|
| 1. decamethylcyclopentasiloxane | 12.0 |
| 2. SS-3408 *18) | 13.0 |
| 3. sucrose oleate | 1.3 |
| 4. decaglycerol oleate | 1.3 |
| 5. composition of Production Example 1 | 28.0 |
| 6. SS-2910 *19) | 4.0 |
| 7. ethanol | 8.0 |
| 8. purified water | 5.9 |
| 9. sodium L-glutamate | 0.1 |
| 10. EP-9215 *20) | 26.4 |

Note
*18) caprylylmethicone
Note
*19) polyether-modified silicone
Note
*20) spherical silicone elastomer powder Production Method A: Heat components 1 to 6 to 60° C. and mix and dissolve to uniformity.

B: Return to room temperature; add component 7 to A; and mix and disperse to uniformity.

C: While stirring B, add a solution of component 9 in component 8 in small portions dropwise to convert the mixture to a gel (gel composition).

D: Add component 10 in small portions to C and mix and disperse to homogeneity to obtain a gel-form cosmetic material.

Formulation Example 10

Emulsified Cosmetic Cream

| (component) | (wt %) |
|---|---|
| 1. dimethylpolysiloxane (6 cSt) | 10.0 |
| 2. SS-3408 *21) | 10.0 |
| 3. cetyl 2-ethylhexanoate | 10.0 |
| 4. composition of Production Example 1 | 4.0 |
| 5. dipropylene glycol | 6.0 |
| 6. purified water | 58.0 |
| 7. sodium L-glutamate | 2.0 |

Note
*21) caprylylmethicone

Production Method

A: Heat components 5 to 7 to 70° C. and mix and dissolve to uniformity.

B: Heat components 1 to 4 to 60° C. and mix and dissolve to uniformity.

C: Return both A and B to room temperature and, while stirring B with a Homo Disper mixer, gradually add A and emulsify to obtain the emulsified cosmetic material cream.

Formulation Example 11

Emulsified Cosmetic Material (Paste-Form)

| (component) | (wt %) |
|---|---|
| 1. dimethylpolysiloxane (6 cSt) | 20.0 |
| 2. SS-3408 *22) | 20.0 |
| 3. glycerol tri-2-ethylhexanoate | 20.0 |
| 4. octyl methoxycinnamate | 8.0 |
| 5. composition of Production Example 1 | 4.0 |
| 6. trimethylsiloxysilicate | 1.0 |
| 7. low-density polyethylene powder | 1.0 |
| 8. spherical polyethylene | 1.0 |
| 9. polystyrene powder | 1.0 |
| 10. polymethylsilsesquioxane powder | 3.0 |
| 11. ethanol | 2.0 |
| 12. dipropylene glycol | 6.0 |
| 13. purified water | 12.0 |
| 14. sodium L-glutamate | 1.0 |
| 15. paraben | suitable quantity |

Note
*22) caprylylmethicone

Production Method

A: Mix components 1 to 6, 11, and 15 and dissolve to uniformity.

B: While stirring A with a Homo Disper mixer, add components 7 to 10 and disperse to uniformity.

C: Heat components 0.12 to 14 to 60° C. and mix and dissolve to uniformity.

D: Return both B and C to room temperature. While stirring B with a Homo Disper mixer, gradually add C and emulsify to obtain the emulsified cosmetic material (paste-form).

Formulation Example 12

Emulsified Foundation

| (component) | (wt %) |
|---|---|
| 1. decamethylcyclopentasiloxane | 27.0 |
| 2. dimethylpolysiloxane (6 cSt) | 2.0 |
| 3. methyltrimethicone (M3T) | 2.0 |
| 4. composition of Production Example 1 | 3.0 |
| 5. propylene glycol | 10.0 |
| 6. ion-exchanged water | 30.0 |
| 7. sodium L-aspartate | 1.0 |
| 8. dextrin palmitate-treated titanium dioxide | 10.0 |
| 9. dextrin palmitate-treated mica | 12.0 |
| 10. dextrin palmitate-treated talc | 2.0 |
| 11. dextrin palmitate-treated iron oxide | 1.0 |
| 12. paraben | suitable quantity |
| 13. antioxidant | suitable quantity |
| 14. fragrance | suitable quantity |

Production Method

A: Heat and dissolve components 1 to 4, 12, and 13 at 50° C.; add components 8 to 11; stir and disperse.

B: Separately, stir, mix, and dissolve components 5 to 7 and 14 at 70° C.

C: Return both A and B to room temperature; add B while stirring the previously prepared A with a homomixer; stir thoroughly. Then degas and fill to obtain the emulsified foundation.

Formulation Example 13

Water-in-Oil Cream

| (component) | (wt %) |
|---|---|
| 1. dimethyldistearylammonium hectorite | 1.0 |
| 2. dioctadecylmethylammonium salt-modified montmorillonite | 1.0 |
| 3. dimethylpolysiloxane (6 cSt) | 5.0 |
| 4. 2-ethylhexyl para-methoxycinnamate | 2.0 |
| 5. diethylpentanediol dineopentanoate | 3.0 |
| 6. DC 9011 Silicone Elastomer Blend *23) | 6.0 |
| 7. composition of Production Example 2 | 1.0 |
| 8. dipropylene glycol | 10.0 |
| 9. sodium citrate | 0.2 |
| 10. ethanol | 3.0 |
| 11. preservative | suitable quantity |
| 12. fragrance | suitable quantity |
| 13. purified water | 67.8 |

Note
*23) dilution of crosslinked polyether-modified silicone with decamethylcyclopentasiloxane wherein the elastomer component is 15%

Production Method
A: Mix components 1 to 7.
B: Mix and dissolve components 8 to 13; add to A and stir and emulsify to obtain the water-in-oil cream.

Formulation Example 14

Water-in-Oil Emulsified Composition

| (component) | (wt %) |
|---|---|
| 1. decamethylcyclopentasiloxane | 6.2 |
| 2. dimethylpolysiloxane (6 cSt) | 3.0 |
| 3. dimethylpolysiloxane (2 cSt) | 2.0 |
| 4. methyltrimethicone (M3T) | 2.0 |
| 5. SH 556 *24) | 3.0 |
| 6. methylpentanediol dineopentanoate | 3.0 |
| 7. 9040 Silicone Elastomer Blend *25 | 5.0 |
| 8. squalane | 5.8 |
| 9. paraffin wax | 0.3 |
| 10. palmitic acid | 0.2 |
| 11. composition of Production Example 1 | 2.0 |
| 12. pseudo-sphingosine | 0.2 |
| 13. pseudo-ceramide | 5.0 |
| 14. magnesium stearate | 1.0 |
| 15. magnesium sulfate | 1.0 |
| 16. methyl para-hydroxybenzoate | 0.2 |
| 17. glycerol | 16.0 |
| 18. dipropylene glycol | 0.5 |
| 19. purified water | 43.6 |

Note
*24) phenyltrimethicone
Note
*25 dilution of crosslinked organopolysiloxane (dimethicone crosspolymer) with decamethylcyclopentasiloxane wherein the elastomer component is 12%

Production Method
A: Heat and stir components 1 to 13 and component 16 at 80 to 90° C. to effect dissolution.
B: Add component 14 to A and stir and mix to effect uniform dispersion.
C: Separately, mix components 15, 17, 18, and 19 to prepare a solution.
D: While stirring B to uniformity and holding at 80° C., gradually add C; cool to room temperature with further stirring to obtain the water-in-oil emulsified composition.

Formulation Example 15

Liquid Lipcolor

| (component) | (wt %) |
|---|---|
| 1. composition of Production Example 2 | 10.0 |
| 2. silicic anhydride (average primary particle size = 10 nm) | 1.5 |
| 3. diisostearyl malate | 15.0 |
| 4. octyldodecanol | 4.0 |
| 5. methyltrimethicone (M3T) | 1.0 |
| 6. heavy liquid isoparaffin | 35.0 |
| 7. squalane | 9.0 |
| 8. sunflower oil | 5.0 |
| 9. trioctanoin | 5.0 |
| 10. vaseline | 5.0 |
| 11. microcrystalline wax | 2.0 |
| 12. Red No. 202 | 0.8 |
| 13. titanium oxide | 0.7 |
| 14. titanium oxide-coated glass powder | 2.0 |
| 15. titanium oxide-coated silica powder | 2.0 |
| 16. N-ε-lauroyl-L-lysine | 2.0 |

Production Method
Mix components 3 to 9 and heat to 90° C.; then add component 2; disperse to uniformity using a homomixer; and add component 1. While continuing to hold the temperature at 90° C., add components 10 to 16; place in the homomixer; and fill into a container and then cool to obtain the liquid lipcolor.

Formulation Example 16

Liquid Cosmetic Emulsion

| (component) | (wt %) |
|---|---|
| 1. decamethylcyclopentasiloxane | 15.0 |
| 2. methylphenylpolysiloxane | 5.0 |
| 3. squalene | 5.0 |
| 4. pentaerythritol tetra-2-ethylhexanoate | 5.0 |
| 5. composition of Production Example 1 | 1.0 |
| 6. BY 22-008M *26) | 2.0 |
| 7. 9701 Cosmetic Powder *27) | 2.0 |
| 8. hydrophobed silica | 0.5 |
| 9. magnesium ascorbate phosphate | 1.0 |
| 10. sodium chloride | 1.0 |
| 11. polyethylene glycol 11000 | 1.0 |
| 12. propylene glycol | 8.0 |
| 13. preservative | suitable quantity |
| 14. fragrance | suitable quantity |
| 15. purified water | balance |

Note
*26) decamethylcyclopentasiloxane solution of polyether-modified silicone, with an effective component content of 12%
Note
*27) spherical organopolysiloxane elastomer powder (silica-coated type)

Production Method
A: Mix components 1 to 6 to uniformity; add components 7 and 8 and disperse to uniformity.
B: Add components 9 to 11 to component 15 and dissolve; mix components 12 and 13 to uniformity and add.
C: Gradually add B to A and emulsify; then cool; add component 14 to obtain the liquid cosmetic emulsion.

Formulation Example 17

O/W Cream (O/W Hand Cream)

| (component) | (wt %) |
|---|---|
| 1. 2503 Cosmetic Wax *28) | 5.0 |
| 2. cetanol | 1.0 |
| 3. liquid paraffin | 10.0 |
| 4. SH 556 *29) | 13.0 |
| 5. vaseline | 2.0 |
| 6. candelilla wax | 2.0 |
| 7. glyceryl triisostearate | 5.0 |
| 8. stearic acid | 3.0 |
| 9. glyceryl monostearate | 1.5 |
| 10. composition of Production Example 2 | 2.0 |
| 11. sorbitan sesquioleate | 0.5 |
| 12. polyoxyethylene sorbitan monooleate | 1.0 |
| 13. sodium hydroxide (1% aqueous solution) | 10.0 |
| 14. 1,3-butylene glycol | 5.0 |
| 15. glycerol | 5.0 |
| 16. preservative | suitable quantity |
| 17. fragrance | suitable quantity |

-continued

| (component) | (wt %) |
|---|---|
| 18. BY 29-129 *30) | 5.0 |
| 19. purified water | 51.0 |

Note
*28) stearyldimethicone
Note
*29) phenyltrimethicone
Note
*30) aqueous dispersion of spherical organopolysiloxane elastomer powder, with an effective component content of 63%

Production Method
A: Mix, heat, and dissolve components 1 to 12.
B: Mix, heat, and dissolve components 13 to 16 and 19.
C: Add B to A and emulsify; cool to 40° C.; and add components 18 and 17 and mix to uniformity.
D: Cool further to room temperature to obtain the O/W hand cream.

Formulation Example 18

Eye Shadow

| (component) | (wt %) |
|---|---|
| 1. decamethylcyclopentasiloxane | 13.0 |
| 2. dimethylpolysiloxane (6 cSt) | 10.0 |
| 3. methyltrimethicone (M3T) | 2.0 |
| 4. composition of Production Example 1 | 2.0 |
| 5. PEG(10) lauryl ether | 0.5 |
| 6. silicone-treated chromium oxide *31) | 6.2 |
| 7. silicone-treated ultramarine *31) | 4.0 |
| 8. silicone-treated titanium-coated mica *31) | 6.0 |
| 9. sodium chloride | 2.0 |
| 10. propylene glycol | 8.0 |
| 11. preservative | suitable quantity |
| 12. fragrance | suitable quantity |
| 13. purified water | 46.3 |

Note
*31) The silicone treatment is carried out by adding a methylhydrogenpolysiloxane at 3% with respect to the powder and then heating.

Production Method
A: Mix components 1 to 5; add components 6 to 8; disperse to uniformity.
B: Dissolve components 9 to 11 and component 13 to uniformity.
C: While stirring, gradually add B to A and emulsify; add component to obtain the eye shadow.

Formulation Example 19

Mascara

| (component) | (wt %) |
|---|---|
| 1. isododecane | 24.0 |
| 2. methyltrimethicone (M3T) | 1.0 |
| 3. dimethylpalmitylpolysiloxane | 1.0 |
| 4. dimethylpolysiloxane (100,000 cSt) | 1.0 |
| 5. microcrystalline wax | 5.0 |
| 6. beeswax | 3.0 |
| 7. composition of Production Example 1 | 2.0 |
| 8. silicone-coated iron oxide black | 14.0 |
| 9. bentonite | 2.0 |

-continued

| (component) | (wt %) |
|---|---|
| 10. nylon fiber (average length = 2 μm) | 2.0 |
| 11. para-hydroxybenzoate ester | 0.5 |
| 12. anhydrous ethanol | 2.5 |
| 13. polyvinyl alcohol | 0.5 |
| 14. alkyl acrylate copolymer emulsion (50% dispersion) | 19.5 |
| 15. alkyl acrylate•styrene copolymer emulsion (50% dispersion) | 8.0 |
| 16. purified water | 14.0 |

Production Method
A: Mix and dissolve components 1 to 7; then add components 8 to 10 while stirring with a Homo Disper mixer and disperse to uniformity.
B: Dissolve component 11 in component 12; add this to component 16 and mix to make uniform.
C: Mix B with components 14 and 15 and bring to uniformity; then add component 13 and mix to make uniform.
D: While stirring A with the Homo Disper mixer, gradually add C to obtain the mascara.

Formulation Example 20

Solid Powdered Eye Shadow

| (component) | (wt %) |
|---|---|
| 1. talc (hydrophobed) | 16.0 |
| 2. sericite (hydrophobed) | 30.0 |
| 3. titanium mica (hydrophobed) | 35.0 |
| 4. ultramarine (hydrophobed) | 4.0 |
| 5. iron oxide (hydrophobed) | 2.0 |
| 6. SS-2910 *32) | 5.0 |
| 7. composition of Production Example 2 | 0.5 |
| 8. decamethylcyclopentasiloxane | 4.5 |
| 9. tetrakistrimethylsiloxysilane (M4Q) | 2.0 |
| 10. liquid paraffin | 0.5 |
| 11. paraffin | 0.5 |

Note
*32) polyether-modified silicone

Production Method
A: Stir and mix components 1 to 5 with a blender.
B: Heat and dissolve components 6 to 10.
C: Spray B into A and stir further; then grind and compression mold with a molder to obtain the solid powdered eye shadow.

Formulation Example 21

Pressed Powder Cosmetic Material

| (component) | (wt %) |
|---|---|
| 1. silicone-treated titanium oxide | 10.0 |
| 2. silicone-treated mica | 50.8 |
| 3. silicone-treated talc | 10.0 |
| 4. silicone-treated iron oxide yellow | 1.5 |
| 5. silicone-treated iron oxide red | 0.5 |
| 6. silicone-treated iron oxide black | 0.2 |
| 7. paraffin wax | 2.0 |
| 8. squalane | 1.4 |
| 9. 2-ethylhexyl palmitate | 2.0 |
| 10. composition of Production Example 2 | 1.5 |
| 11. SS-3408 *33) | 16.1 |

-continued

| (component) | (wt %) |
|---|---|
| 12. methyltrimethicone (M3T) | 1.0 |
| 13. dimethylpolysiloxane | 3.0 |
| 14. fragrance | suitable quantity |

Note
*33) caprylylmethicone

Production Method
A: Mix components 1 to 6.
B: Mix components 7 to 13 and add A.
C: Add component 14 to B and press-mold into a metal tray.

Formulation Example 22

Pressed Foundation

| (component) | (wt %) |
|---|---|
| 1. perfluoropolyether-treated titanium oxide | 9.0 |
| 2. perfluoropolyether-treated zinc oxide | 3.0 |
| 3. perfluoropolyether-treated iron oxide red | 0.4 |
| 4. perfluoropolyether-treated iron oxide yellow | 4.0 |
| 5. perfluoropolyether-treated iron oxide black | 0.2 |
| 6. perfluoropolyether-treated talc | 15.0 |
| 7. perfluoropolyether-treated mica | 48.2 |
| 8. perfluoropolyether-treated titanium mica | 2.0 |
| 9. 9701 Cosmetic Powder *34) | 2.0 |
| 10. squalane | 4.0 |
| 11. dimethylpolysiloxane (2 cSt) | 7.0 |
| 12. vaseline | 2.0 |
| 13. glyceryl triisooctanoate | 2.0 |
| 14. composition of Production Example 2 | 1.0 |
| 15. preservative | 0.1 |
| 16. fragrance | 0.1 |

Note
*34) spherical organopolysiloxane elastomer powder (silica-coated type)

Production Method
A: Mix and disperse components 1 to 9.
B: Heat components 10 to 14 and mix to uniformity.
C: Add B to A; mix and grind; then compression mold into a metal tray to give the pressed foundation.

Formulation Example 23

Cream

| (component) | (wt %) |
|---|---|
| 1. hydrogenated soy phospholipid | 1.0 |
| 2. cholesterol | 0.5 |
| 3. dipropylene glycol | 10.0 |
| 4. glycerol | 10.0 |
| 5. purified water | 56.5 |
| 6. sodium lactate | 1.0 |
| 7. composition of Production Example 1 | 2.0 |
| 8. decamethylcyclopentasiloxane | 9.5 |
| 9. methyltrimethicone (M3T) | 1.5 |
| 10. glyceryl tri-2-ethylhexanoate | 5.0 |
| 11. meadowfoam oil | 3.0 |

Production Method
A: Heat components 1 to 4 to 75° C.
B: Heat components 5 and 6 to 75° C.
C: Add B to A and mix and then cool to room temperature.
D: While stirring, gradually add C to components 7 to 11 and mix to obtain the cream.

Formulation Example 24

Foundation

| (component) | (wt %) |
|---|---|
| 1. hydrogenated soy phospholipid | 0.5 |
| 2. phytosterol | 0.1 |
| 3. squalane | 1.0 |
| 4. glycerol | 2.0 |
| 5. 1,3-butylene glycol | 2.0 |
| 6. purified water | balance |
| 7. sodium chloride | 1.0 |
| 8. methyl para-hydroxybenzoate | 0.3 |
| 9. ethanol | 3.0 |
| 10. composition of Production Example 1 | 0.5 |
| 11. SS-2910 *35) | 2.5 |
| 12. diglyceryl diisostearate | 1.0 |
| 13. 2-ethylhexyl para-methoxycinnamate | 3.0 |
| 14. glyceryl tri-2-ethylhexanoate | 5.0 |
| 15. pentaerythritol rosinate | 0.1 |
| 16. dextrin palmitate | 0.5 |
| 17. inulin stearate | 0.5 |
| 18. dimethyldistearylammonium hectorite | 1.0 |
| 19. silicone-treated titanium oxide | 10.0 |
| 20. silicone-treated iron oxide red | 0.3 |
| 21. silicone-treated iron oxide yellow | 1.5 |
| 22. silicone-treated iron oxide black | 0.05 |
| 23. silicone-treated finely divided titanium oxide | 2.0 |
| 24. nylon powder | 2.0 |
| 25. decamethylcyclopentasiloxane | 18.0 |

Note
*35) polyether-modified silicone

Production Method
A: Heat components 1 to 5 to 75° C.
B: Heat component 6 to 75° C.
C: Add B to A with mixing and then cool to room temperature.
D: Add components 7 to 9 to C with mixing.
E: Mix components 10 to 25 with a roll mill.
F: While stirring, add E to D and mix to obtain the foundation.

Formulation Example 25

Hair Treatment

| (component) | (wt %) |
|---|---|
| 1. behenyltrimethylammonium chloride | 8.0% |
| 2. behenyl alcohol | 7.0% |
| 3. dimethylpolysiloxane (2 cSt) | 4.0% |
| 4. composition of Production Example 2 | 0.5% |
| 5. aminopropyldimethicone (molecular weight = 500,000) | 0.4% |
| 6. dimethylpolysiloxane (10 cSt) | 0.6% |
| 7. dimethylpolysiloxane (100,000 cSt) | 0.2% |
| 8. behenic acid | 1.0% |
| 9. polyoxyethylene(20) sorbitan monostearate | 0.5% |
| 10. dipropylene glycol | 6.0% |
| 11. glycerol | 10.0% |
| 12. 50% aqueous citric acid solution | suitable quantity |
| 13. methylparaben | suitable quantity |
| 14. fragrance | suitable quantity |
| 15. purified water | balance |

Production Method
A: Mix component 1 and components 9 to 15 and heat to 80° C. and dissolve.

B: Heat components 2 to 8 to 80° C. and dissolve.
C: Add B to A at 80° C.; emulsify and mix to uniformity; cool.
D: Fill C into a container to obtain the hair conditioner.

Formulation Example 26

Styling Mousse

| (component) | (wt %) |
|---|---|
| 1. cationized vinylpyrrolidone•dimethylaminoethyl methacrylate copolymer compound | 5.0% |
| 2. BY 22-050A *36) | 0.1% |
| 3. composition of Production Example 2 | 0.5% |
| 4. ethanol | 10.0% |
| 5. preservative | suitable quantity |
| 6. fragrance | suitable quantity |
| 7. purified water | balance |
| 8. liquefied petroleum gas | 7.0% |

Note
*36) 50% water-based emulsion of a highly polymerized dimethylsiloxane (1,000,000 cSt)

Production Method
A: Mix components 1 to 7 to uniformity.
B: Fill A and component 8 into an aerosol container to obtain the styling mousse.

The invention claimed is:

1. A gel composition comprising:
   10 to 70 mass % of thickener or gellant for oil materials,
   30 to 80 mass % of (D) oil material,
   0 to 20 mass % of (E) at least one compound selected from the group consisting of lower monohydric alcohols and organic polyhydric alcohol compounds, and
   0 to 20 mass % (F) water,
   wherein the thickener or gellant comprises (A) an organopolysiloxane that has a polyglycerol structure-containing hydrophilic group Q and that is represented by the following structural formula (1):

$$R_{3-q}-\underset{R^{11}}{\underset{|}{Si}}-O-\left(\underset{R^{11}}{\underset{|}{Si}}-O\right)_{n1}-\left(\underset{R^{11}}{\underset{|}{Si}}-O\right)_{n2}-\left(\underset{R^{11}}{\underset{|}{Si}}-O\right)_{n3}-\underset{R^{11}}{\underset{|}{Si}}-R_{3-q} \quad (1)$$

wherein $R^{11}$ is a substituted or unsubstituted $C_{1-30}$ monovalent hydrocarbyl group or is the hydrogen atom; L is a chain organosiloxane group represented by the following structural formula (2-1) or (2-2):

$$-C_tH_{2t}-\left[\underset{R^{11}}{\underset{|}{Si}}-O\right]_r-\underset{R^{11}}{\underset{|}{Si}}-R^{11} \quad (2-1)$$

wherein $R^{11}$ is a group as defined above, t is a number in the range from 2 to 10, and r is a number in the range from 1 to 100

$$-O-\left[\underset{R^{11}}{\underset{|}{Si}}-O\right]_r-\underset{R^{11}}{\underset{|}{Si}}-R^{11} \quad (2-2)$$

wherein $R^{11}$ is a group as defined above and r is a number in the range from 1 to 100;

Q is a polyglycerol structure-containing hydrophilic group that is bonded to the silicon atom across an at least divalent linker group and that contains at least one type of hydrophilic unit selected from hydrophilic units represented by the following structural formulas (3-1) to (3-3);

$$-\underset{|}{\overset{H_2}{C}}-\underset{|}{\overset{H}{C}}-O- \quad (3-1)$$
$$\phantom{--}CH_2$$
$$\phantom{--}|$$
$$\phantom{--}O$$
$$\phantom{--}|$$
$$\phantom{--}W$$

wherein W is the hydrogen atom or a $C_{1-20}$ alkyl group $$-\underset{|}{\overset{H}{C}}-\underset{|}{\overset{H_2}{C}}-O- \quad (3-2)$$
$$CH_2$$
$$|$$
$$O$$
$$|$$
$$W$$

wherein W is the same group as defined above $$-\overset{H_2}{C}-\underset{|}{\overset{H}{C}}-\overset{H_2}{C}-O- \quad (3-3)$$
$$\phantom{-----}OH$$

R is a group selected from L and Q; n1, n2, and n3 are numbers in the ranges $300 \leq n1 \leq 1000$, $3 \leq n2 \leq 20$, and $3 \leq n3 \leq 20$; and q is an integer in the range from 0 to 3.

2. The gel composition according to claim 1, wherein each Q in structural formula (1) is independently a polyglycerol structure-containing hydrophilic group that is bonded to the silicon atom across an at least divalent linker group and in which at least one type of hydrophilic unit selected from the hydrophilic units represented by the preceding structural formulas (3-1) to (3-3) is connected in straight-chain form,
or a polyglycerol structure-containing hydrophilic group that is bonded to the silicon atom across an at least divalent linker group, that contains at least two of the at least one type of hydrophilic unit selected from the hydrophilic units represented by the preceding structural formulas (3-1) to (3-3), and that has a branching unit selected from groups represented by the following structural formulas (3-5) to (3-7)

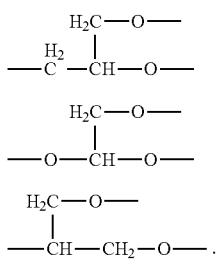

(3-5)

(3-6)

(3-7)

3. The gel composition according to claim 1, characterized in that the hydrophilic group Q is a polyglycerol structure-containing hydrophilic group represented by the following structural formula (4-1), (4-2), (4-3), or (4-4)

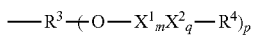 (4-1)

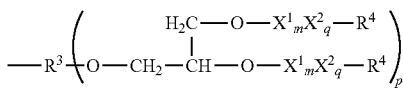 (4-2)

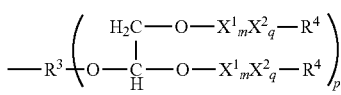 (4-3)

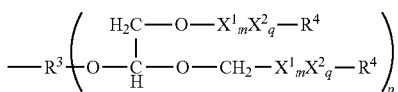 (4-4)

wherein $R^3$ is an organic group with a valence of (p+1); p is a number from 1 to 3;
each $X^1$ is independently at least one type of hydrophilic unit selected from hydrophilic units with the following general formulas (3-1-1) to (3-3-1);
m is a number in the range from 3 to 5;

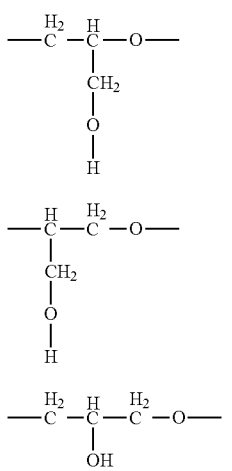

(3-1-1)

(3-2-1)

(3-3-1)

$X^2$ is a hydrophilic unit represented by the following structural formula (3-4-1);
q is a number in the range from 0 to 50; the bonding configuration for each of $X^1$ and $X^2$ is independently a block configuration or a random configuration;

$$—C_rH_{2r}—O—\qquad(3\text{-}4\text{-}1)$$

wherein r is a number in the range from 1 to 6
and $R^4$ is a group selected from the group consisting of the hydrogen atom, $C_{1-20}$ alkyl, acyl groups, and the glycidyl group.

4. The gel composition according to claim 1, wherein each hydrophilic group Q is independently a hydrophilic group derived from a polyglycerol and given by the following structural formula (4-1-1)

$$—R^{3'}—O—X^1_m—R^4\qquad(4\text{-}1\text{-}1)$$

wherein $R^{3'}$ is a divalent organic group; each $X^1$ is independently at least one type of hydrophilic unit selected from hydrophilic units with the previously described general formulas (3-1-1) to (3-3-1); m is a number in the range from 3 to 5; and $R^4$ is a group selected from the group consisting of the hydrogen atom, $C_{1-20}$ alkyl, acyl groups, and the glycidyl group.

5. The gel composition according to claim 1, wherein the hydrophilic group Q is a hydrophilic group derived from tetraglycerol.

6. The gel composition according to claim 1, wherein the thickener or gellant has the following structural formula (1-1):

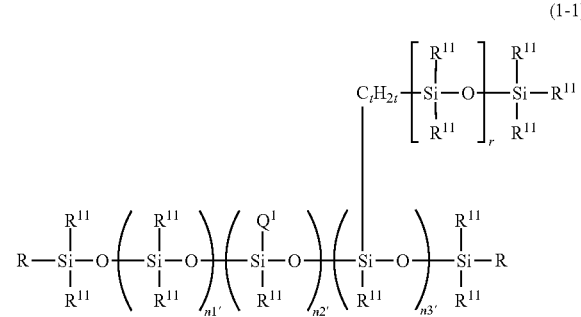

(1-1)

wherein $R^{11}$ is a group as defined above; t and r are the same numbers as defined above; $Q^1$ is a hydrophilic group derived from a polyglycerol and given by the preceding structural formula (4-1-1); n1', n2', and n3' are numbers in the ranges 300≤n1'≤1000, 3≤n2'≤20, and 3≤n3'≤20; and R is $R^{11}$ or $Q^1$.

7. The gel composition according to claim 6, wherein the hydrophilic group $Q^1$ in structural formula (1-1) is a hydrophilic group derived from tetraglycerol.

8. The gel composition according to claim 1, wherein the thickener or gellant further comprises (B) a powder or a colorant.

9. The gel composition according to claim 1, wherein the thickener or gellant further comprises (C) at least one selected from the group consisting of silicone-type surfactants excluding those that correspond to component (A), crosslinked organopolysiloxanes, silicone resins, acrylic silicone resins, acrylic silicone dendrimer copolymers, polyamide-modified silicones, alkyl-modified silicone resin waxes, and organic surfactants.

10. The gel composition according to claim 1, wherein the oil material is (D1) at least one oil selected from solid oils, paste oils, silicone oils, hydrocarbon oils, and ester oils.

11. The gel composition according to claim 8, wherein component (B) is (B1) at least one powder or colorant selected from the group consisting of silicone resin powders, silicone rubber powders, organic resin powders excluding silicone resin powders, organomodified clay minerals, titanium oxide, zinc oxide, titanium mica, metal soaps, inorganic pigments, and inorganic colored pigments.

12. The gel composition according to claim 1, further comprising (G) an ultraviolet absorber.

13. The gel composition according to claim 1, further comprising (H) at least one compound selected from sucrose fatty acid esters and polyglycerol fatty acid esters.

14. The gel composition according to claim 1, further comprising (I) an organic film-forming agent.

15. The gel composition according to claim 1, further comprising (J) at least one compound selected from the group consisting of amino acids and/or salts thereof, inorganic salts, organic acids and/or salts thereof, and water-soluble polymers.

16. A method of producing a cosmetic material, the method comprising:
    mixing 100 mass parts of the gel composition according to claim 1 with 0.1 to 4,000 mass parts of (F) water.

17. A cosmetic material obtained by mixing 100 mass parts of the gel composition according to claim 1 with 0.1 to 4,000 mass parts of (F) water.

18. The gel composition according to claim 1, further comprising from
    20 to 60 mass % of the thickener or gellant, and,
        wherein the gel composition is further defined as a gel-form cosmetic material, and
        wherein the thickener or gellant further comprises (B) a powder or a colorant.

19. A method of producing a topical agent, the method comprising: mixing 100 mass parts of the gel composition according to claim 1, 0.1 to 4,000 mass parts of (F) water, and 0.001 to 1.0 mass part of (L) a physiologically active substance.

20. A topical agent obtained by mixing 100 mass parts of the gel composition according to claim 1, 0.1 to 4,000 mass parts of (F) water, and 0.001 to 1.0 mass part of (L) a physiologically active substance.

21. The gel composition according to claim 1, further comprising from
    20 to 60 mass % of the thickener or gellant,
    and
    0.001 to 1.0 mass % of (L) a physiologically active substance,
        wherein the gel composition is further defined as a gel-form topical agent, and
        wherein the thickener or gellant further comprises (B) a powder or a colorant.

22. The topical agent according to claim 20, wherein (L) the physiologically active substance is at least one physiologically active substance selected from the group consisting of antiinflammatories, ageing inhibitors, whiteners, hair-restoring agents, hair-growth agents, circulation promoters, antibacterials, antiseptics, vitamins, wound-healing promoters, anti-irritants, analgesics, cell activators, and enzymes.

23. A hair cosmetic that characteristically comprises the gel composition according to claim 1 and (N) a cationic surfactant.

24. A hair-setting agent composition that characteristically comprises the gel composition according to claim 1 and (P) an organic film-forming polymer.

25. A method of producing the gel composition of claim 1, the method comprising addition reacting at least
    (A') an organohydrogenpolysiloxane that contains silicon-bonded hydrogen and that has a degree of polymerization of more than 200, and
    (K) a polyglycerol structure-containing hydrophilic compound that has one alkenyl group wherein the alkenyl group resides in terminal position on the molecular chain and that contains at least one type of hydrophilic unit selected from the hydrophilic units given by the previously described structural formulas (3-1) to (3-3) in the presence of
    (M) a hydrosilylation reaction catalyst to form the thickener or gellant; and combining: 10 to 70 mass % of the thickener or gellant, 30 to 80 mass % of (D) oil material, 0 to 20 mass % of (E) at least one compound selected from the group consisting of lower monohydric alcohols and organic polyhydric alcohol compounds, and 0 to 20 mass % (F) water to form the gel composition of claim 1.

26. A method of producing the gel composition of claim 6, the method comprising addition reacting at least
    (A') an organohydrogenpolysiloxane that contains silicon-bonded hydrogen and that has a degree of polymerization of more than 300,
    a chain organopolysiloxane given by general formula (2') below, that has one carbon-carbon double bond wherein the carbon-carbon double bond resides in terminal position on the molecular chain, and
    (K1) a polyglycerol structure-containing hydrophilic compound that has one alkenyl group wherein the alkenyl group resides in terminal position on the molecular chain and that contains within the molecule at least one type of hydrophilic unit selected from the hydrophilic units given by structural formulas (3-1-1) to (3-3-1)
    in the presence of
    (M) a hydrosilylation reaction catalyst to form the thickener or gellant;

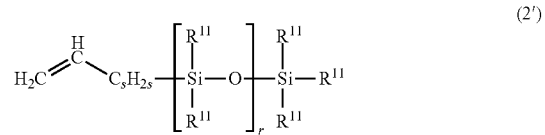

wherein $R^{11}$ is the same as described above, s is a number in the range from 0 to 8, and r is a number in the range from 1 to 100, and
combining: 10 to 70 mass % of the thickener or gellant, 30 to 80 mass % of (D) oil material, 0 to 20 mass % of (E) at least one compound selected from the group consisting of lower monohydric alcohols and organic polyhydric alcohol compounds, and 0 to 20 mass % (F) water to form the gel composition of claim 6.

* * * * *